US012679849B2

(12) United States Patent
Karche et al.

(10) Patent No.: US 12,679,849 B2
(45) Date of Patent: Jul. 14, 2026

(54) MACROCYCLIC COMPOUNDS AS STING AGONISTS

(71) Applicant: LUPIN LIMITED, Maharashtra (IN)

(72) Inventors: Navnath Popat Karche, Taluka Mulshi (IN); Moloy Banerjee, Taluka Mulshi (IN); Pradeep Rangrao Patil, Taluka Mulshi (IN); Vinod Popatrao Vyavahare, Taluka Mulshi (IN); Deepak Sahebrao Walke, Taluka Mulshi (IN); Vaibhav Madhukar Kalhapure, Taluka Mulshi (IN); Vidya Ramdas, Taluka Mulshi (IN); Venkata P. Palle, Taluka Mulshi (IN); Rajender Kumar Kamboj, Taluka Mulshi (IN)

(73) Assignee: LUPIN LIMITED, Maharashtra (IN)

( * ) Notice: Subject to any disclaimer, the term of this patent is extended or adjusted under 35 U.S.C. 154(b) by 1325 days.

(21) Appl. No.: 17/598,524

(22) PCT Filed: Mar. 21, 2020

(86) PCT No.: PCT/IB2020/052654
§ 371 (c)(1),
(2) Date: Sep. 27, 2021

(87) PCT Pub. No.: WO2020/194160
PCT Pub. Date: Oct. 1, 2020

(65) Prior Publication Data

US 2022/0144852 A1 May 12, 2022

(30) Foreign Application Priority Data

Mar. 28, 2019 (IN) ............................. 201921012258
Nov. 13, 2019 (IN) ............................. 201921046194

(51) Int. Cl.
*C07D 498/16* (2006.01)

(52) U.S. Cl.
CPC .................................. *C07D 498/16* (2013.01)

(58) Field of Classification Search
CPC .................................................... C07D 498/16
See application file for complete search history.

(56) References Cited

U.S. PATENT DOCUMENTS 10,981,901 B1 * 4/2021 Romano ................. A61P 37/00

FOREIGN PATENT DOCUMENTS

| | | | | |
|---|---|---|---|---|
| WO | 2017/011920 A1 | 1/2017 | | |
| WO | 2017/175156 A1 | 10/2017 | | |
| WO | WO-2017175147 A1 * | 10/2017 | ............. | A61P 43/00 |
| WO | 2018/234808 A1 | 12/2017 | | |
| WO | 2018/234805 A1 | 12/2018 | | |
| WO | 2018/234807 A1 | 12/2018 | | |
| WO | 2019/023635 A1 | 1/2019 | | |
| WO | 2019/027857 A1 | 2/2019 | | |
| WO | 2019/027858 A1 | 2/2019 | | |

OTHER PUBLICATIONS

PCT International Search Report and Written Opinion for PCT Application No. PCT/IB2020/052654 mailed May 26, 2020 (10 pages).
Barber, "Sting: Infection, Inflammation and Cancer," Nature, 2015, 15:760-770.
Conlon et al., "Mouse, but not Human STING, Binds and Signals in Response to the Vascular Disrupting Agent 5,6-Dimethylxanthenone-4-Acetic Acid," The Journal of Immunology, 2013, 190:5216-5225.
Corrales et al., "Direct Activation of STING in the Tumor Microenvironment Leads to Potent and Systemic Tumor Regression and Immunity," Cell Reports, 2015, 11:1018-1030.
Deng et al., "STING-Dependent Cystolic DNA Sensing Promotes Radiation-Induced Type I Interferon-Dependent Antitumor Immunity in Immunogenic Tumors," Immunity, 2014, 41:843-853.

(Continued)

*Primary Examiner* — Clinton A Brooks
*Assistant Examiner* — Josmalen M. Ramos-Lewis
(74) *Attorney, Agent, or Firm* — Volpe Koenig

(57) ABSTRACT

Disclosed are the macrocyclic compounds having the general Formula (I) and their tautomeric forms, stereoisomers, pharmaceutically acceptable salts, and their combination with suitable medicament, corresponding processes for the synthesis and pharmaceutical compositions and uses of compounds disclosed herein.

(I)

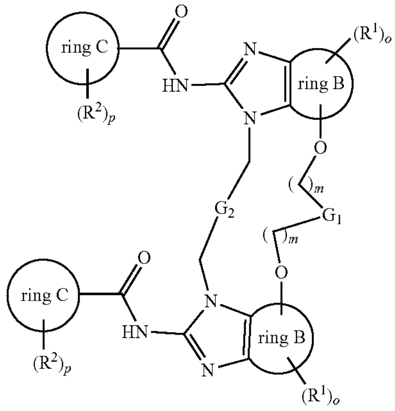

10 Claims, No Drawings

(56) References Cited

OTHER PUBLICATIONS

Diamond et al., "Type I Interferon is Selectively Required by Dendritic Cells for Immune Rejection of Tumors," J. Exp. Med., 2011, 208(10):1989-2003.

Galon et al., "Cancere Classification Using the Immunoscore: A Worldwide Task Force," Journal of Translational Medicine, 2012, 10:205 (10 pages).

Guo et al., "STING Agonists Induce an Innate Antiviral Immune Response Against Hepatitis B Virus," Antimicrobial Agents and Chemotherapy, 2015, 59(2):1273-1281.

Harlin et al., "Chemokine Expression in Melanoma Metastases Associated with CD8+ T-Cell Recruitment," Cancer Res., 2009, 69(7):3077-3085.

Ishikawa et al., "STING an Endoplasmic Recticulum Adaptor that Facilitates Innate Immune Signaling," Nature, 2008, 455(7213):674-678.

Postow et al., "Targeting Immune Checkpoints: Releasing the Restraints on Anti-Tumor Immunity for Patients with Melanoma," Cancer J., 2012, 18(2):153-159.

Ramanjulu et al., "Design of Amidobenzimidazole STING Receptor Agonists with Systemic Activity," Nature, 2018, 564:439-443.

Sali et al., "Characterization of a Novel Human-Specific STING Agonist that Elicits Antiviral Activity Against Emerging Alphaviruses," PLOS Pathogens, 2015 (30 pages).

Shirey et al., "The Anti-Tumor Agent, 5,6-Dimethylxanthenone-4-Acetic Acid (DMXAA), Induces IFN-B-Mediated Antiviral Activity in vitro and in vivo," Journal of Leukocyte Biology, 2011, 89:351-357.

Woo et al., "STING-Dependent Cytosolic DNA Sensing Mediaes Innate Immune Recognition of Immunogenic Tumors," Immunity, 2014, 41:830-842.

* cited by examiner

MACROCYCLIC COMPOUNDS AS STING AGONISTS

This application is a National Stage Application of PCT/IB2020/052654, filed 21 Mar. 2020, which claims benefit of Ser. No. 201921012258, filed 28 Mar. 2019 in India, and Ser. No. 201921046194, filed 13 Nov. 2019 in India, and which applications are incorporated herein by reference. To the extent appropriate, a claim of priority is made to each of the above disclosed applications.

FIELD OF THE INVENTION

The present invention relates to macrocyclic compounds having the general Formula (I) and their tautomeric forms, stereoisomers, pharmaceutically acceptable salts, and their combination with suitable medicament, corresponding processes for the synthesis and pharmaceutical compositions and uses of compounds containing the present invention.

CROSS REFERENCE TO THE RELATED APPLICATIONS

The present application claims the benefit of Indian Provisional Patent Application Nos. 201921012258, filed on 28 Mar. 2019 and 201921046194 filed on 13 Nov. 2019, the disclosure of which are incorporated herein by reference in their entirety for all purposes.

BACKGROUND OF THE INVENTION

Stimulator of interferon genes (STING, also known as transmembrane protein 173/TMEM173/MPYS/MITA/ERIS) is a signalling molecule that in humans is encoded by TMEM173 gene. STING is protein with 379 amino acids, consisting of several transmembrane regions. STING protein is expressed in several endothelial and epithelial cell types, as well as in haematopoietic lineage, such as T cells, dendritic cells (DCs) including plasmacytoid dendritic cells (pDCs) and macrophages. STING is associated with endoplasmic reticulum (ER) in the cell and has a major role in controlling the transcription of numerous host defence genes, including type I interferons (IFNs) and pro-inflammatory cytokines.

Recognition of aberrant DNA species or cyclic dinucleotides (CDNs) in the cytosol of the cell leads to the activation of STING. Cytosolic DNA species can activate STING signalling following binding to cyclic GMP-AMP synthase (cGAS). Binding of cytosolic DNA to cGAS catalyses the production of a type of CDN known as cGAMP (cyclic GMP-AMP), which contains one 2',5'-phosphodiester linkage and a canonical 3',5' linkage (c[G(2',5')pA(3',5')p]). The binding of cGAMP and other bacterial CDNs induce changes in the conformation of STING protein and facilitates the binding of TANK-binding kinase 1 (TBK1). STING-TBK1 complex, further transposes to perinuclear regions of the cell to transport TBK1 to endolysosomal compartments where it phosphorylates the transcription factors like, interferon regulatory factor 3 (IRF3). Similarly, STAT6 and nuclear factor-κB (NF-κB) also get activated downstream to STING activation. These transcription factors then translocate into the nucleus to initiate innate immune gene transcription and production of type I IFN and other cytokines. STING is then rapidly degraded, an event that may avoid problems associated with sustained cytokine production. (Nature Reviews Immunol, 2015, 15, 760-770; Cell Reports, 2015, 11, 1018-1030)

Studies in mice have shown that type I IFN signalling plays an important role in tumour-initiated T cell priming and tumour control (J. Exp. Med. 2011, 208, 1989-2003). Mice lacking the IFN-α/β receptor in DCs failed to reject immunogenic tumours, and CD8α+ DCs from these mice are defective in antigen cross-presentation to CD8+ T cells. Additionally, transcriptional profiling analyses of melanoma patients has publicised that tumours containing infiltrating activated T cells are characterized by a type I IFN transcriptional signature (Cancer Res. 2009, 69, 3077-3085). Numerous studies have demonstrated that activation of the STING pathway in tumour-resident host APCs is required for induction of a spontaneous CD8+ T cell response against tumour-derived antigens in vivo (Immunity, 2014, 41, 830-842). Extensive evidence directs that the tumour-infiltrating lymphocytes (TILs) are correlated with favourable prediction in diverse malignancies (J. Transl. Med. 2012, 10, 205) and predicts a positive clinical outcome in response to several immunotherapy strategies (Cancer J. 2012, 18, 153-159). STING activation partially contributing to the antitumor activity of chemotherapeutic agents as well as radiotherapy (Immunity, 2014, 41, 843-852). Further, STING activation and signalling has been discovered to be essential for protection against the development of cancer by promoting antitumor immune responses. Thus, activation of STING represents a potential immunotherapy approach for cancer treatment.

Studies have shown that direct intra-tumoral injection (I.Tu.) of modified CDNs into established B16F10 melanoma, CT26 colon, and 4T1 breast carcinomas resulted in rapid and significant tumour regression and long lasting systemic anti-tumour immunity. So, activation of the STING pathway in the TME by specific agonists might be an effective therapeutic strategy to promote broad tumour-initiated T cell priming and thereby treatment of cancer. (J. Immunol. 2013, 190, 5216-5225; Cell Rep. 2015, 19, 11(7), 1018-30). Besides CDNs, other class of compounds can activate STING.

Parallel to the anticancer mechanism of STING, STING activation to its downstream also leads to induction of several antiviral genes which include IFN-0 and several interferons stimulated genes (ISGs). Ablation of STING in murine embryonic fibroblasts made them susceptible to negative-stranded virus infection, including vesicular stomatitis virus. The first-generation mouse STING agonist DMXAA shown to be effective in multiple in-vivo viral models like HBV (hepatitis B virus) DNA Hydrodynamic Mouse Model, Chikungunya virus, H1N1 PR8 influenza strain indicating the utility of STING agonist as antiviral agent against multiple viral infections. (Nature, 2008, 455, 674-678; PLoS Pathog. 2015, 11, 12; Antimicrob. Agents Chemother. 2015, 59, 2 1273-1281; J Leukocyte Bio. 2011, 89, 3 351-357).

International publications WO2017/011920, WO2017/175147, WO2017/175156, WO2018,234805, WO2018,234807, WO2018,234808, WO2019/023635, WO2019/027857, WO2019/027858, and Nature (2018), 564 (7736), 439-443 discloses STING modulators. The compounds of present invention having STING modulator activity are described herein.

SUMMARY OF THE INVENTION

The present invention relates to compounds of general Formula (I), and their tautomeric forms, stereoisomers, pharmaceutically acceptable salts, hydrates, solvates or its prodrug thereof.

(I)

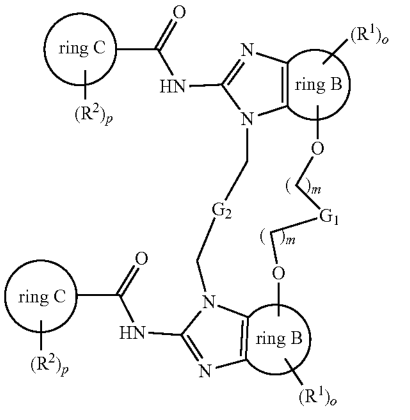

wherein, $G_1$ is independently selected from ring A or

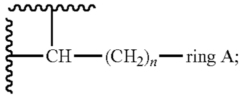

$G_2$ is —CH═CH—;

ring A is independently selected from optionally substituted heterocyclyl, and optionally substituted heteroaryl;

ring B is aromatic carbocyclic ring;

ring C is optionally substituted five membered heteroaryl;

$R^1$ is —CON($R^3$)$_2$;

$R^2$ is independently selected from hydrogen, optionally substituted $C_1$-$C_6$ alkyl, and optionally substituted $C_3$-$C_5$ monocyclic cycloalkyl;

$R^3$ is independently selected from hydrogen, and optionally substituted $C_1$-$C_6$ alkyl;

m is selected from 0, or 1;

n is selected from 0, 1, or 2;

is 1;

p is selected from 0, 1, or 2;

when 'alkyl' is substituted, it is substituted with 1 to 4 substituents independently selected from halogen, alkyl, perhaloalkyl, cycloalkyl, heterocyclyl, —N($R^4$)$_2$, and —O$R^4$;

when 'carbocycle' or 'cycloalkyl' is substituted, it is substituted with 1 to 4 substituents independently selected from halogen, alkyl, perhaloalkyl, —N($R^4$)$_2$, and —O$R^4$;

when 'heterocycle' or 'heterocyclyl' is substituted, it is substituted with 1 to 4 substituents independently selected from oxo (═O), halogen, cyano, alkyl, perhaloalkyl, —O$R^4$, —C(═O)OH, —OP(O)(O$R^4$)$_2$, —P(O)(O$R^4$)$_2$, —P(O)(O$R^4$)$R^{4a}$, —SO$_2R^{4a}$, —SO$_2$NH$_2$, —C(═O)N(H)$R^4$, —C(═O)N(alkyl)$R^4$, —N(H)C(═O)$R^{4a}$, —N(H)$R^4$, and —N(alkyl)$R^4$;

when the 'heteroaryl' group is substituted, it is substituted with 1 to 4 substituents selected from halogen, cyano, alkyl, perhaloalkyl, —O-alkyl, —O-perhaloalkyl, —N(alkyl)alkyl, —N(H)$R^4$, —SO$_2$-alkyl, —N(alkyl)C(═O)alkyl, —N(H)C(═O)alkyl, —C(═O)N(alkyl)alkyl, —C(═O)N(H)alkyl, —C(═O)NH$_2$, —SO$_2$N(alkyl)alkyl, —SO$_2$N(H)alkyl, —SO$_2$NH$_2$, —C(═O)OH, —OP(O)(O$R^4$)$_2$, —P(O)(O$R^4$)$_2$, and —P(O)(O$R^4$)$R^{4a}$;

each $R^4$ is independently selected from hydrogen, alkyl, and cycloalkyl; and each $R^{4a}$ is independently selected from alkyl, and cycloalkyl.

In another embodiment, the invention provides a compound of general Formula (Ia), and their tautomeric forms, stereoisomers, its pharmaceutically acceptable salt, hydrate, solvate, or its prodrug thereof, (Ia)

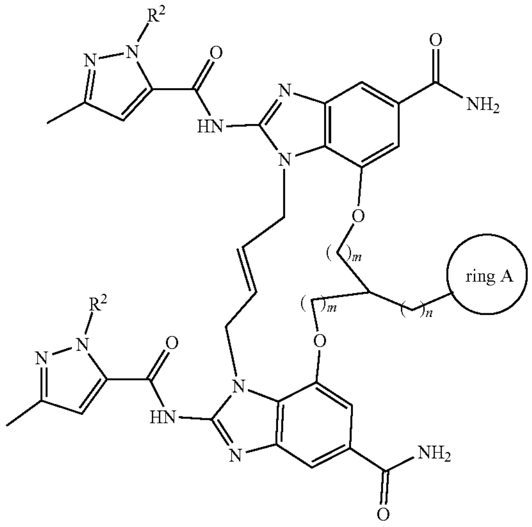

wherein, $R^2$, ring A, m and n are as defined earlier.

In another embodiment, the invention provides a compound of Formula (Ib), and their tautomeric forms, stereoisomers, its pharmaceutically acceptable salt, hydrate, solvate, or its prodrug thereof, (Ib)

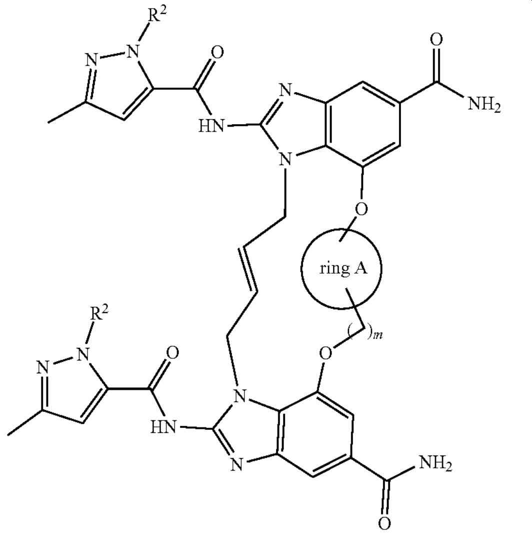

wherein, $R^2$, ring A, and m are as defined earlier.

According to another embodiment, the invention relates the compound of Formula (I), Formula (Ia) or Formula (Ib), its tautomeric form, its stereoisomer, its pharmaceutically acceptable salt, hydrate, solvate, or its prodrug, wherein ring A is optionally substituted heterocyclyl or optionally substituted heteroaryl.

According to another embodiment, the invention relates the compound of Formula (I), and Formula (Ia) its tautomeric form, its stereoisomer, its pharmaceutically acceptable salt, hydrate, solvate, or its prodrug, wherein ring A is

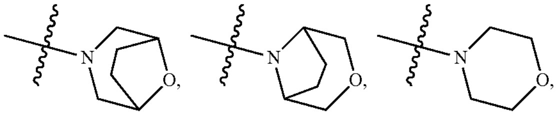

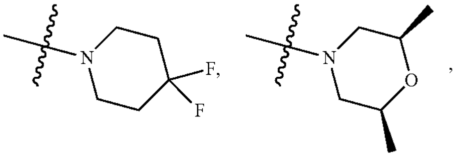

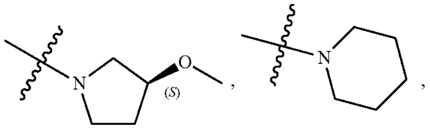

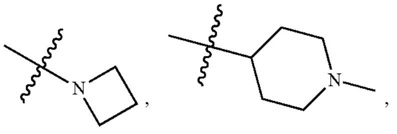

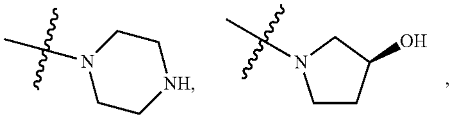

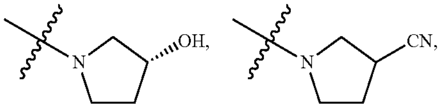

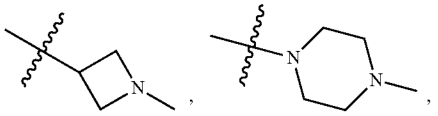

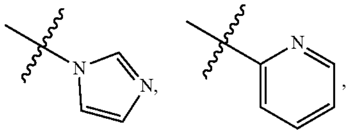

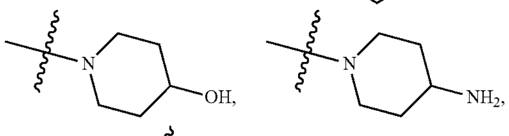

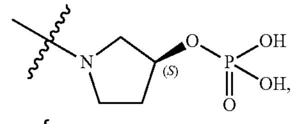

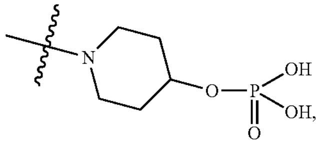

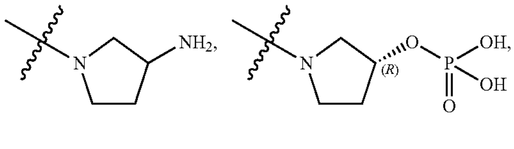

-continued

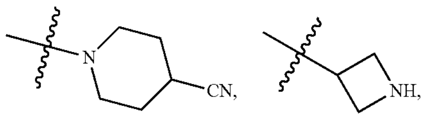

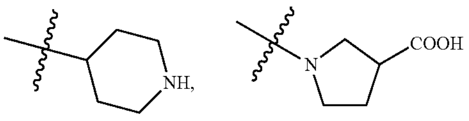

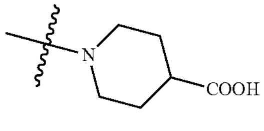

and

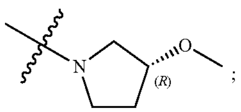

;

According to another embodiment, the invention relates the compound of Formula (Tb), and its tautomeric form, its stereoisomer, its pharmaceutically acceptable salt, hydrate, solvate, or its prodrug, wherein ring A is

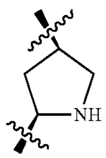

and

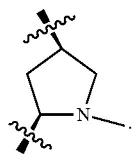

According to another embodiment, the invention relates the compound of Formula (I), Formula (Ia) or Formula (Ib), its tautomeric form, its stereoisomer, its pharmaceutically acceptable salt, hydrate, solvate, or its prodrug, wherein $R^2$ is optionally substituted $C_1$-$C_6$ alkyl.

According to another embodiment, the invention relates the compound of Formula (I), Formula (Ia) or Formula (Tb), its tautomeric form, its stereoisomer, its pharmaceutically acceptable salt, hydrate, solvate, or its prodrug, wherein $R^2$ is optionally substituted ethyl.

According to another embodiment, the invention relates the compound of Formula (I), or Formula (Ia) its tautomeric form, its stereoisomer, its pharmaceutically acceptable salt, hydrate, solvate, or its prodrug, wherein n is 0,1, or 2.

According to another embodiment, the invention relates the compound of Formula (I), or Formula (Ia) its tautomeric form, its stereoisomer, its pharmaceutically acceptable salt, hydrate, solvate, or its prodrug, wherein n is 0.

According to another embodiment, the invention relates the compound of Formula (I), its tautomeric form, its stereoisomer, its pharmaceutically acceptable salt, hydrate, solvate, or its prodrug, wherein $R^2$ is optionally substituted $C_1$-$C_6$ alkyl; n is 0, 1, or 2; and ring A is optionally substituted heterocyclyl or optionally substituted heteroaryl.

In another embodiment, the invention provides a compound of Formula (I), their tautomeric forms, and their all possible geometrical isomers, including, but not limiting to Formula (A), Formula (B), Formula (C), Formula (D), and Formula (E) as represented below:

(I)
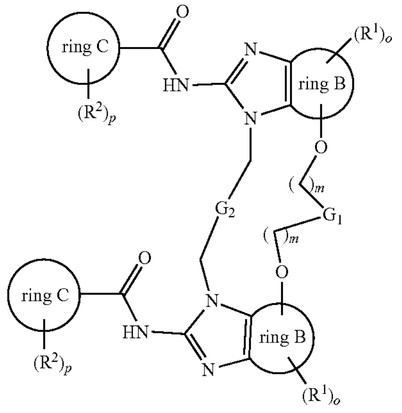
(A)
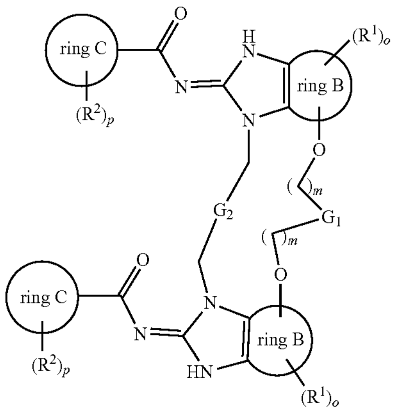
EZ
(B)
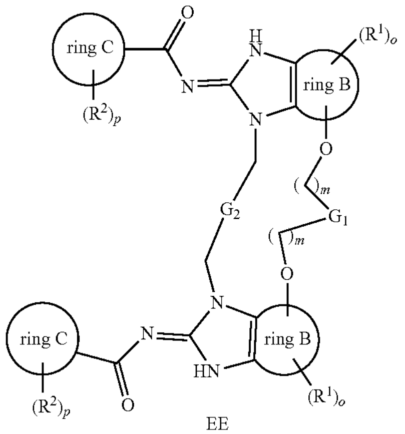
EE
-continued
(C)
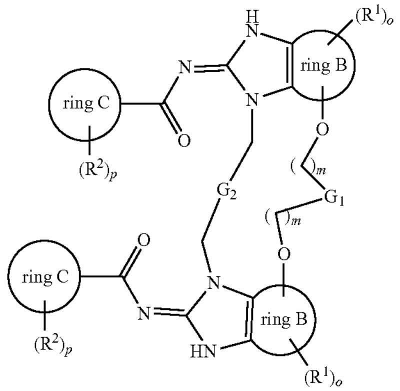
ZZ
(D)
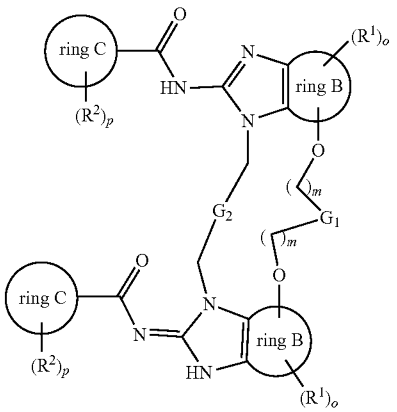
Z
(E)
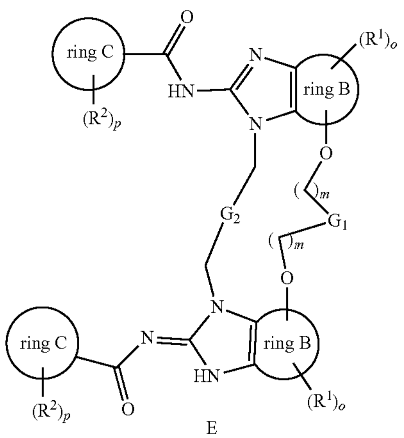
E In another embodiment, the invention provides a compound of Formula (I), Formula (Ia) or Formula (Ib), their tautomeric forms, its pharmaceutically acceptable salt, hydrate, solvate, or its prodrug, wherein the compound is selected from:

| Ex. No | Structure | IUPAC Name |
|---|---|---|
| 1 | 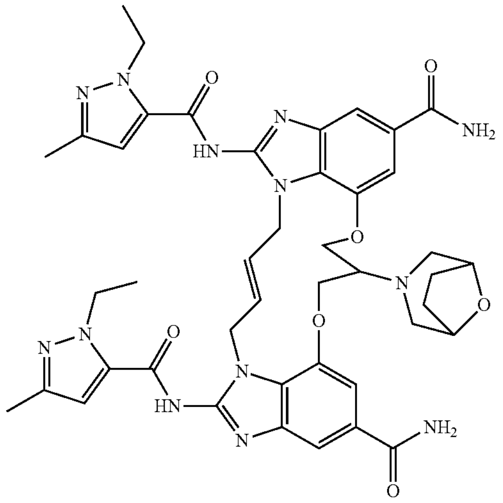 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC2CCC(C1)O2)CO3] | (E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 1) |
| 2 | 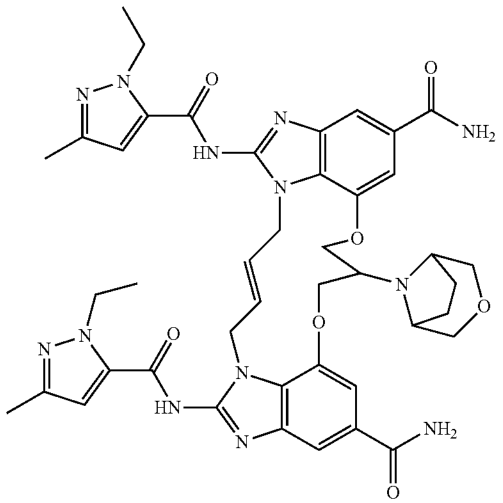 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1C2CCC1COC2)CO3] | (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 2) |

-continued

| Ex. No | Structure | IUPAC Name |
| --- | --- | --- |
| 3 | 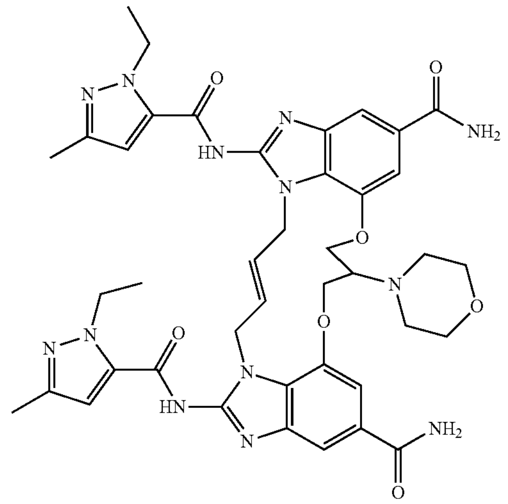 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCOCC1)CO3] | (E)-1,15-bis(1-ethyl-3-methyl-1H-pyrazole-5-carboxamido)-8-morpholino-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 3) |
| 4 | 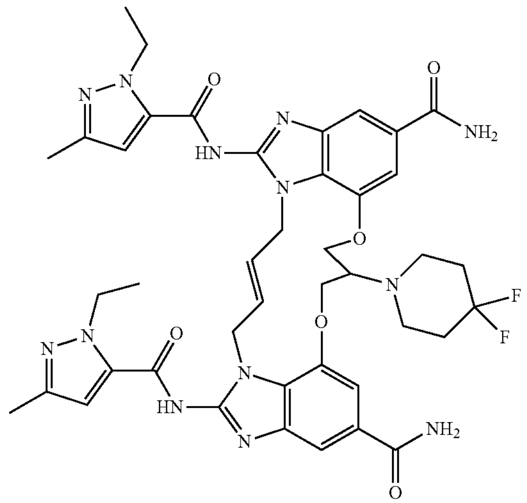 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(F)(F)CC1)CO3] | (E)-8-(4,4-difluoropiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 4) |
| 5 | 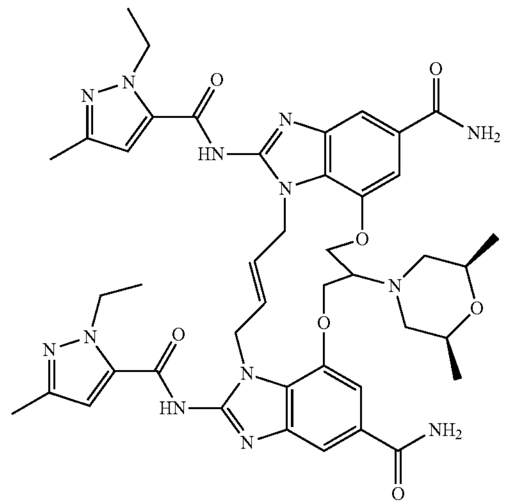 | (E)-8-((2S,6R)-2,6-dimethylmorpholino)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 5) |

-continued

| Ex. No | Structure | IUPAC Name |
| --- | --- | --- |
| 6 | 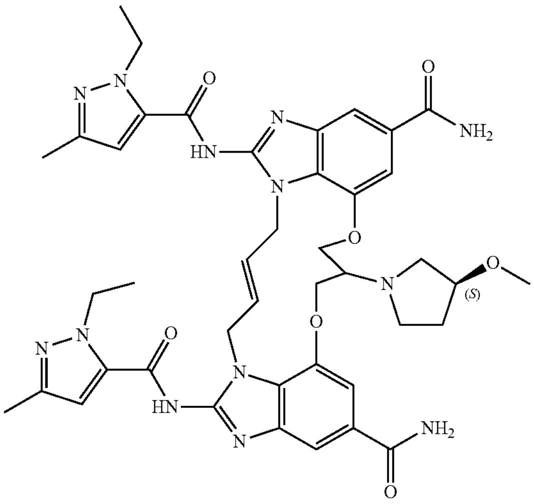 | (S,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 6) |
| 7 | 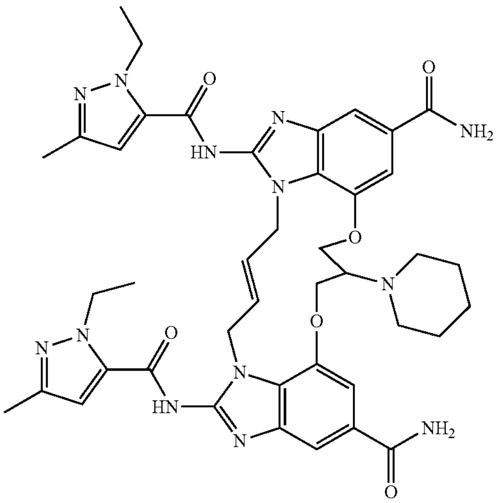 | (E)-1,15-bis(1-ethyl-3-methyl-1H-pyrazole-5-carboxamido)-8-(piperidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 7) |
| 8 | 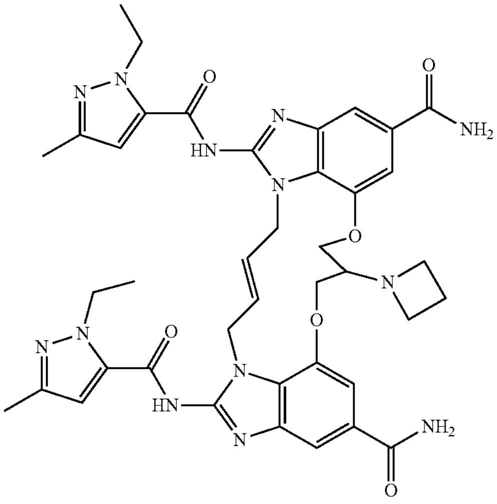 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC1)CO3] | (E)-8-(azetidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 8) |

-continued

| Ex. No | Structure | IUPAC Name |
|---|---|---|
| 9 | 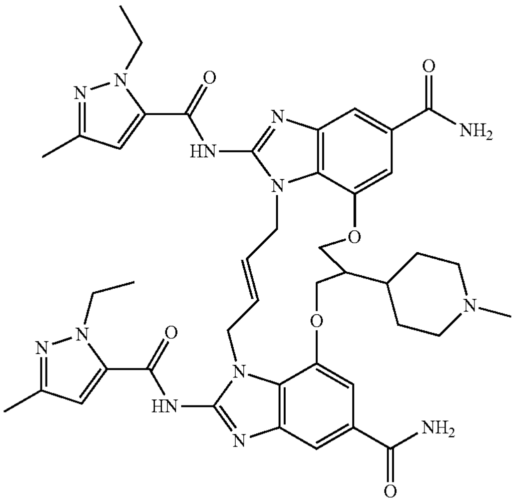 | (E)-1,15-bis(1-ethyl-3-methyl-1H-pyrazole-5-carboxamido)-8-(1-methylpiperidin-4-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 9) |
| 10 | 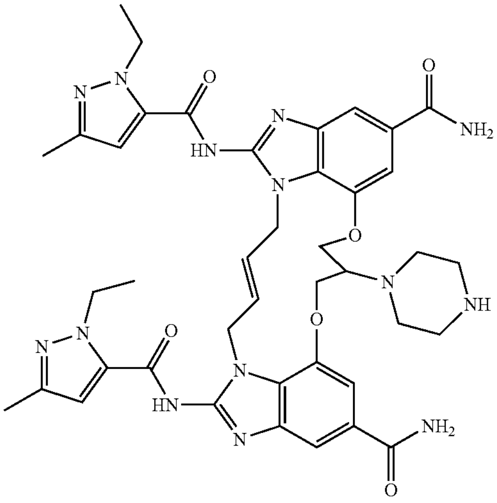 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCNCC1)CO3] | (E)-1,15-bis(1-ethyl-3-methyl-1H-pyrazole-5-carboxamido)-8-(piperazin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 10) |
| 11 | 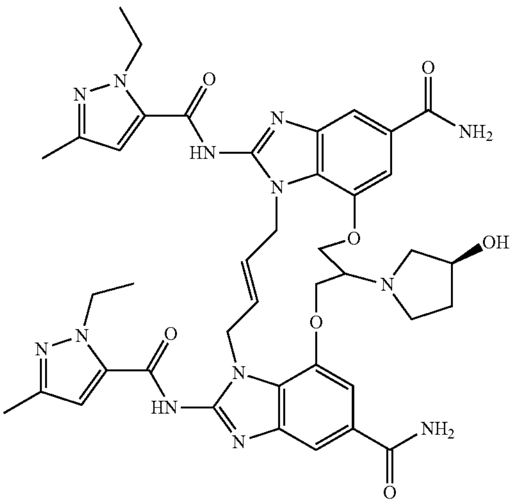 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@H](O)C1)CO3] | (S,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 11) |

-continued

| Ex. No | Structure | IUPAC Name |
|---|---|---|
| 12 | 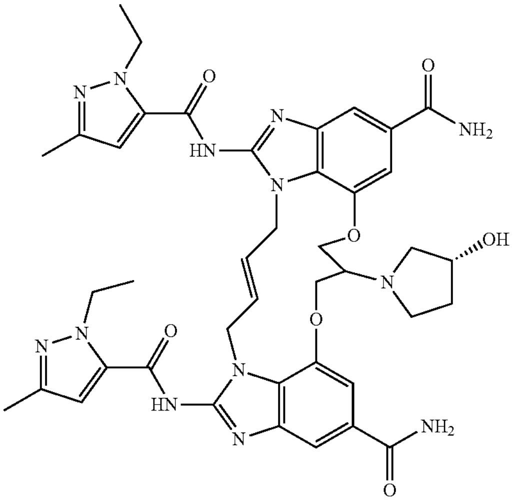 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@@H](O)C1)CO3] | (R,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 12) |
| 13 | 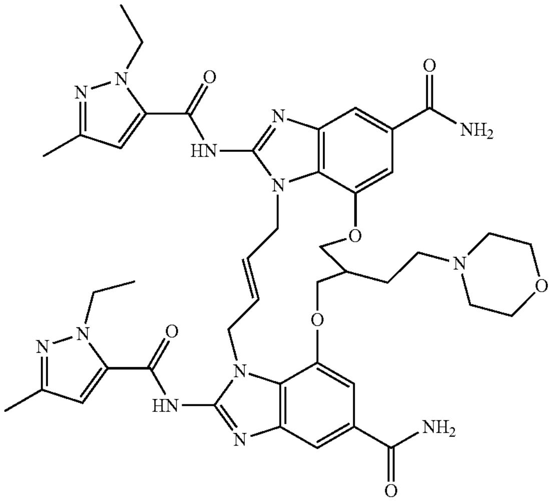 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(CCN1CCOCC1)CO3] | (E)-1,15-bis(1-ethyl-3-methyl-1H-pyrazole-5-carboxamido)-8-(2-morpholinoethyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 13) |
| 14 | 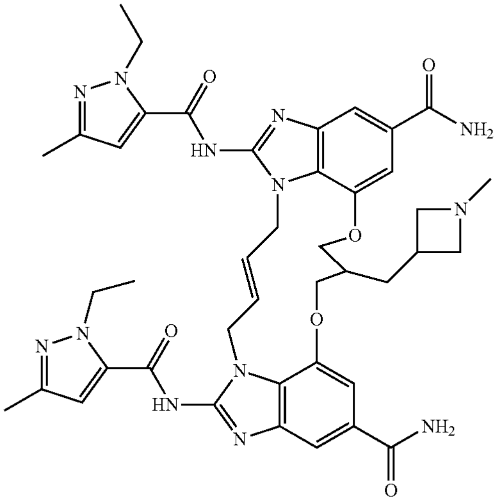 | (E)-1,15-bis(1-ethyl-3-methyl-1H-pyrazole-5-carboxamido)-8-((1-methylazetidin-3-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 14) |

-continued

| Ex. No | Structure | IUPAC Name |
|---|---|---|
| 15 | 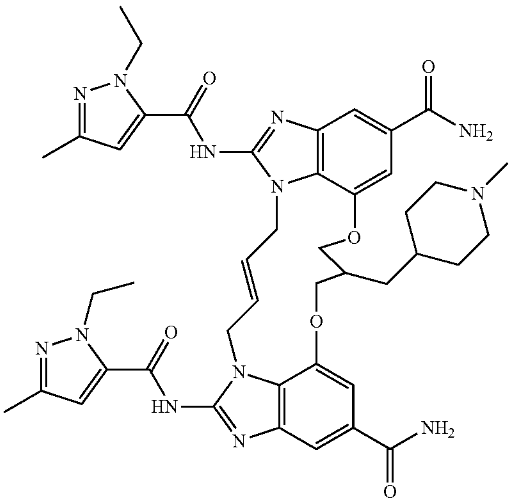 | (E)-1,15-bis(1-ethyl-3-methyl-1H-pyrazole-5-carboxamido)-8-((1-methylpiperidin-4-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 15) |
| 16 | 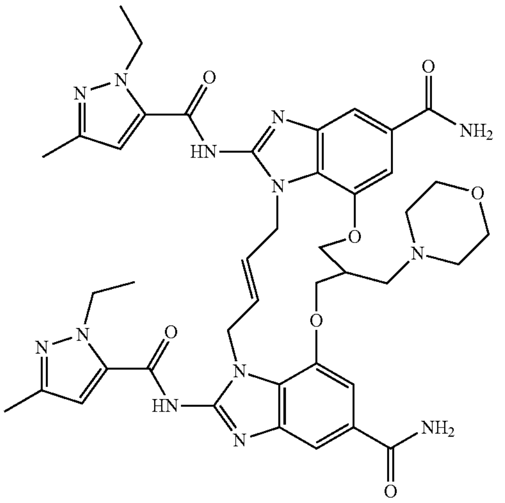 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(CN1CCOCC1)CO3] | (E)-1,15-bis(1-ethyl-3-methyl-1H-pyrazole-5-carboxamido)-8-(morpholinomethyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 16) |
| 17 | 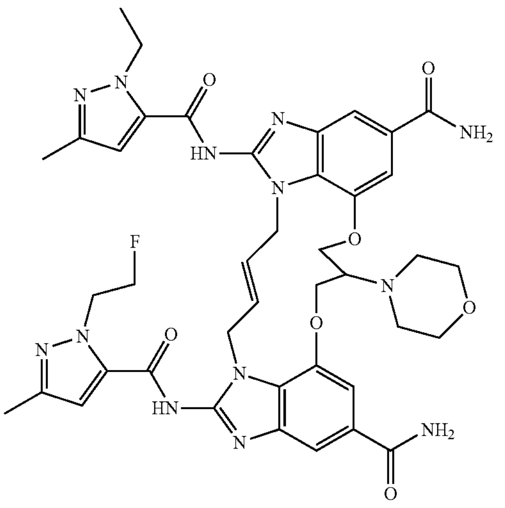 [SMILES: CCn1nc(C)cc1C(=O)Nc1nc2cc(C(N)=O)cc3c2n1C/C=C/Cn1c(NC(=O)c2cc(C)nn2CCF)nc2cc(C(N)=O)cc(c21)OCC(N1CCOCC1)CO3] | (E)-15-(1-ethyl-3-methyl-1H-pyrazole-5-carboxamido)-1-(1-(2-fluoroethyl)-3-methyl-1H-pyrazole-5-carboxamido)-8-morpholino-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 17) |

-continued

| Ex. No | Structure | IUPAC Name |
|---|---|---|
| 18 | 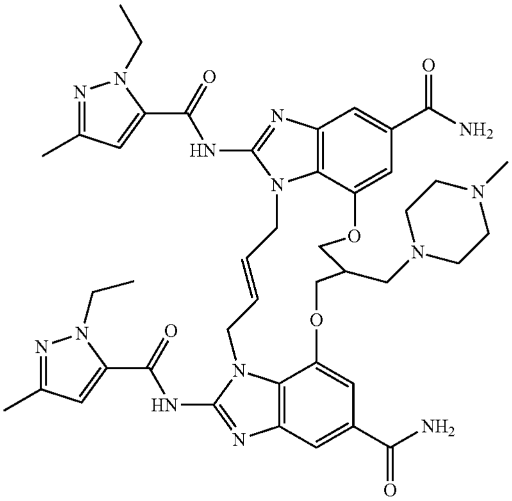 | (E)-1,15-bis(1-ethyl-3-methyl-1H-pyrazole-5-carboxamido)-8-((4-methylpiperazin-1-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 18) |
| 19 | 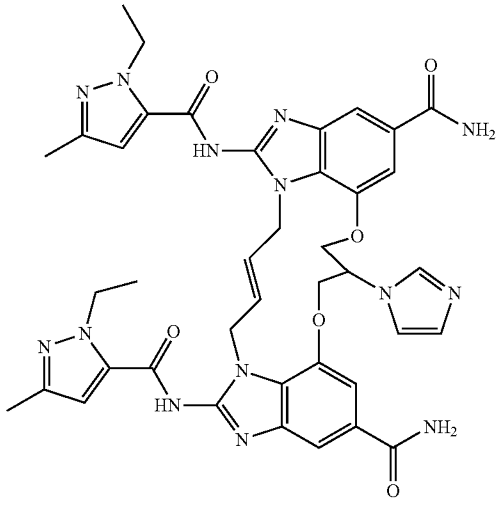 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(n1ccnc1)CO3] | (E)-1,15-bis(1-ethyl-3-methyl-1H-pyrazole-5-carboxamido)-8-(1H-imidazol-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 19) |
| 20 | 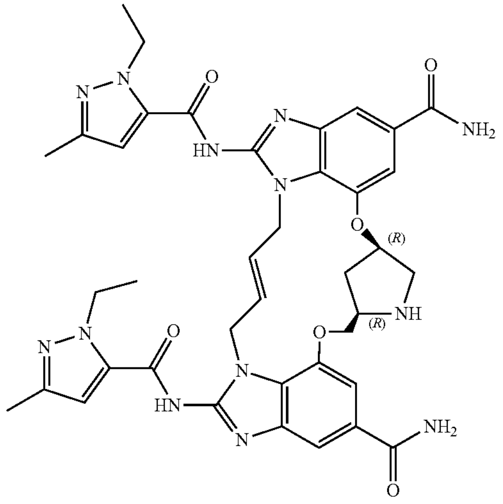 | (33R,35R,E)-12,62-bis(1-ethyl-3-methyl-1H-pyrazole-5-carboxamido)-11H,61H-2,5-dioxa-1,6(7,1)-dibenzo[d]imidazola-3(3,5)-pyrrolidinacyclodecaphan-8-ene-15,65-dicarboxamide (Compound 20) |

-continued

| Ex. No | Structure | IUPAC Name |
|---|---|---|
| 21 | 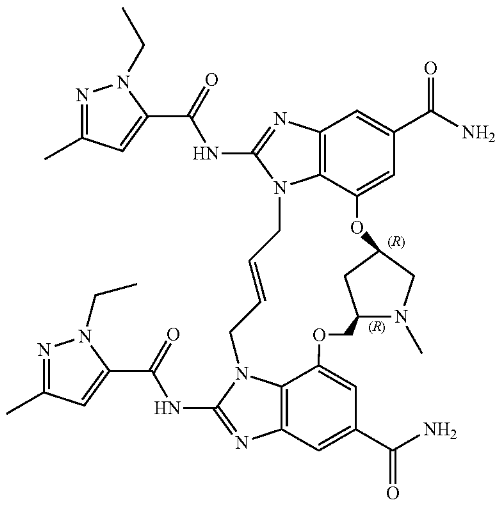 | (33R,35R,E)-12,62-bis(1-ethyl-3-methyl-1H-pyrazole-5-carboxamido)-31-methyl-11H,61H-2,5-dioxa-1,6(7,1)-dibenzo[d]imidazola-3(3,5)-pyrrolidinacyclodecaphan-8-ene-15,65-dicarboxamide (Compound 21) |
| 22 | 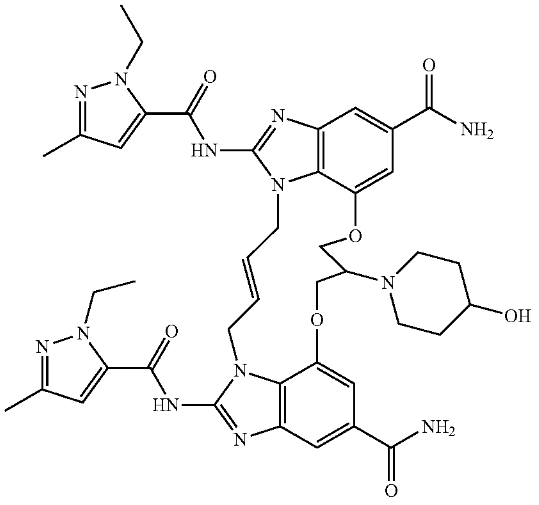 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(O)CC1)CO3] | (E)-1,15-bis(1-ethyl-3-methyl-1H-pyrazole-5-carboxamido)-8-(4-hydroxypiperidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 22) |
| 23 | 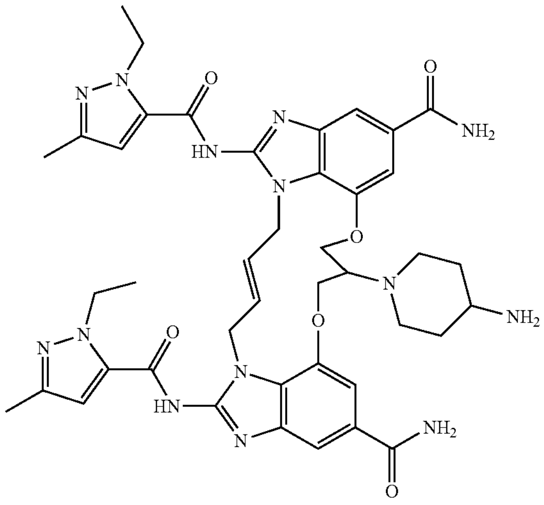 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(N)CC1)CO3] | (E)-8-(4-aminopiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 23) |

-continued

| Ex. No | Structure | IUPAC Name |
|---|---|---|
| 24 | 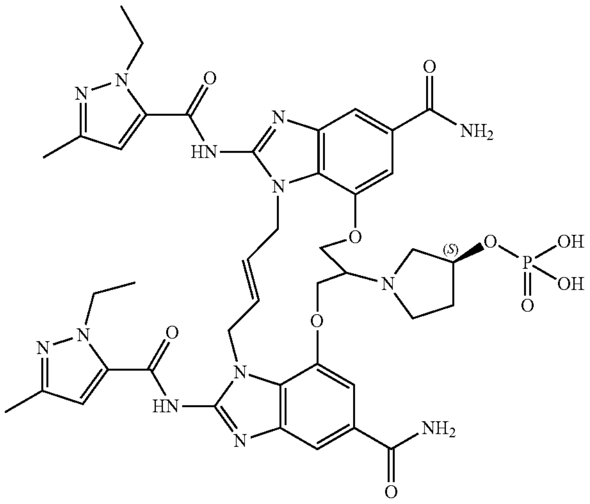 | (S,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl dihydrogen phosphate (Compound 24) |
| 25 | 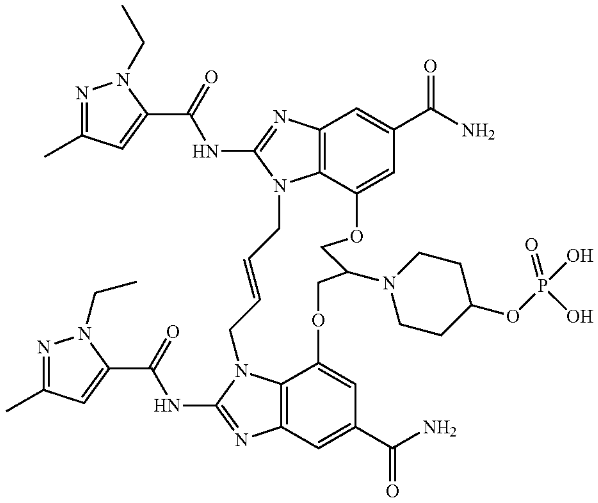 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(OP(=O)(O)O)CC1)CO3] | (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)piperidin-4-yl dihydrogen phosphate (Compound 25) |
| 26 | 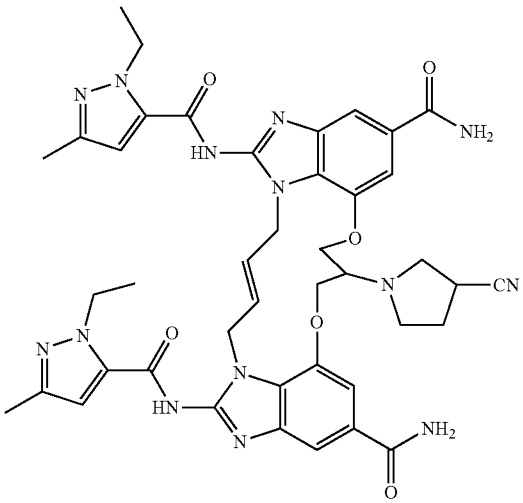 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C#N)C1)CO3] | (E)-8-(3-cyanopyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 26) |

-continued

| Ex. No | Structure | IUPAC Name |
|---|---|---|
| 27 | 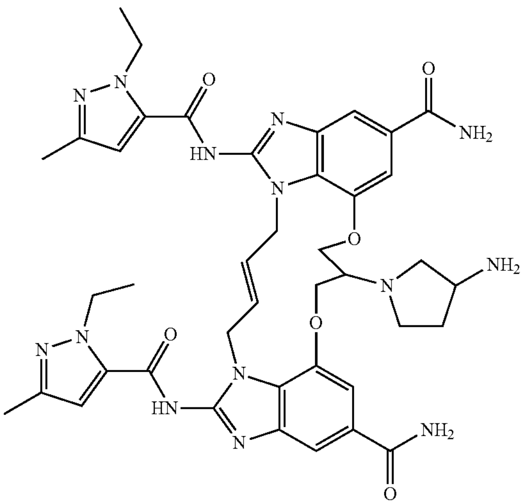 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(N)C1)CO3] | (E)-8-(3-aminopyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 27) |
| 28 | 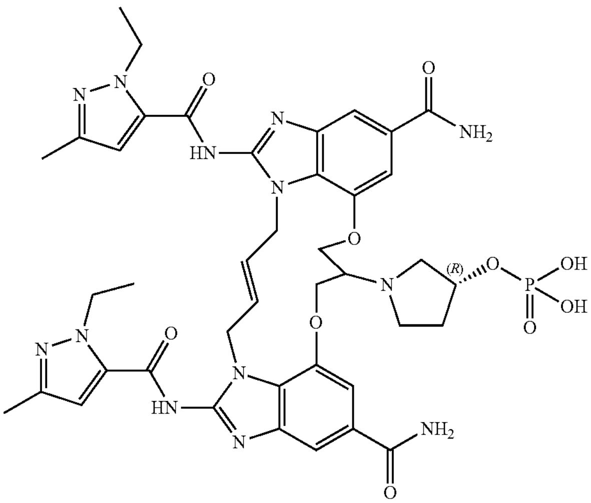 | (R,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl dihydrogen phosphate (Compound 28) |
| 29 | 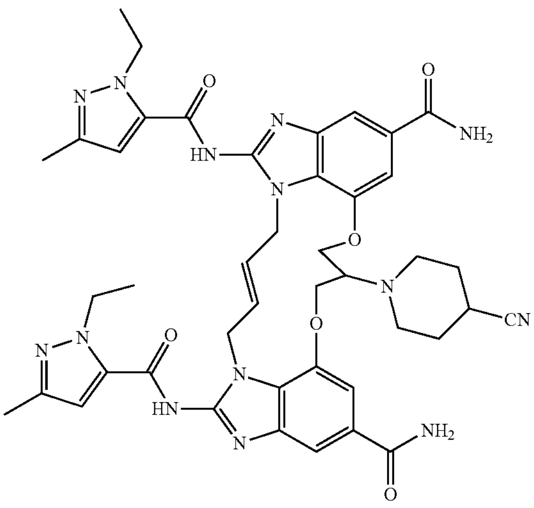 | (E)-8-(4-cyanopiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 29) |

-continued

| Ex. No | Structure | IUPAC Name |
|---|---|---|
| 30 | 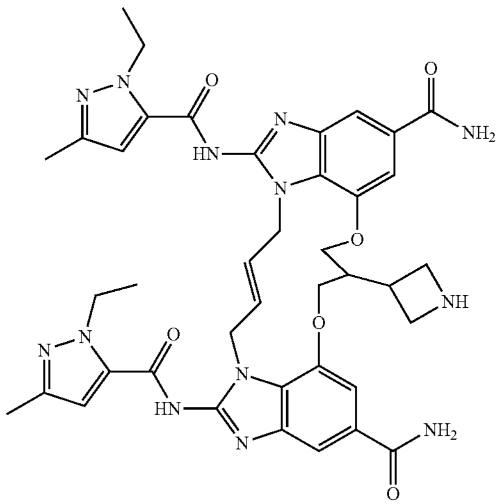 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(C1CNC1)CO3] | (E)-8-(azetidin-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 30) |
| 31 | 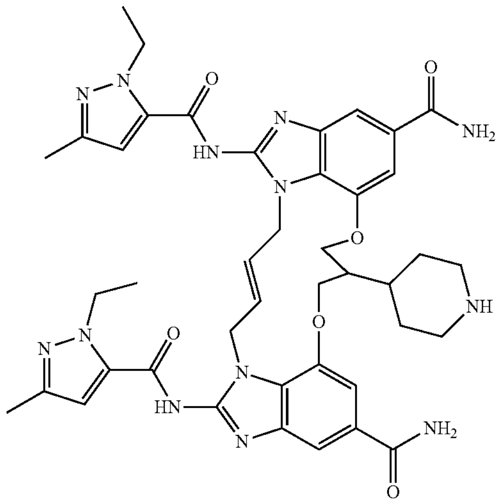 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(C1CCNCC1)CO3] | (E)-1,15-bis(1-ethyl-3-methyl-1H-pyrazole-5-carboxamido)-8-(piperidin-4-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 31) |
| 32 | 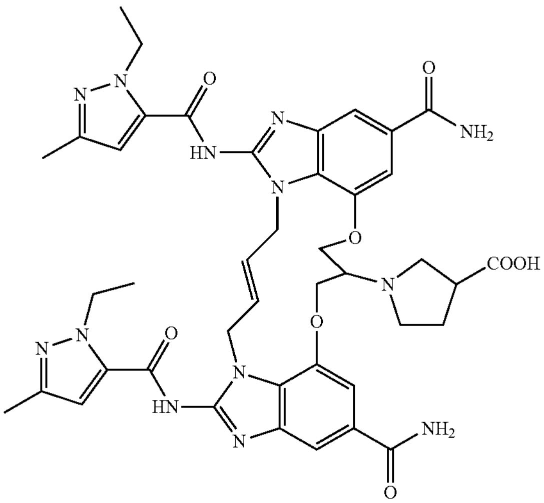 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)O)C1)CO3] | (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidine-3-carboxylic acid (Compound 32) |

-continued

| Ex. No | Structure | IUPAC Name |
|---|---|---|
| 33 | 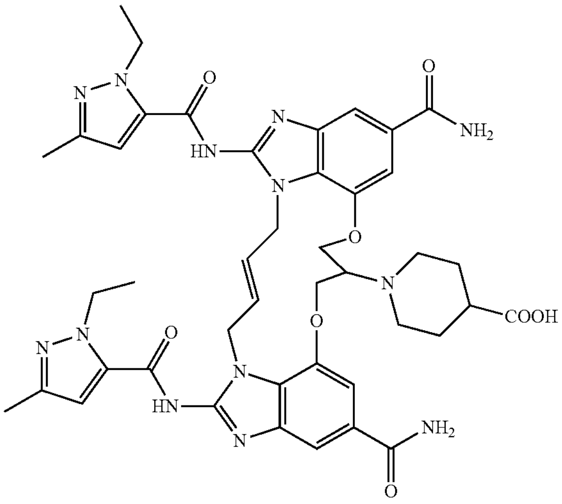 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)O)CC1)CO3] | (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)piperidine-4-carboxylic acid (Compound 33) |
| 34 | 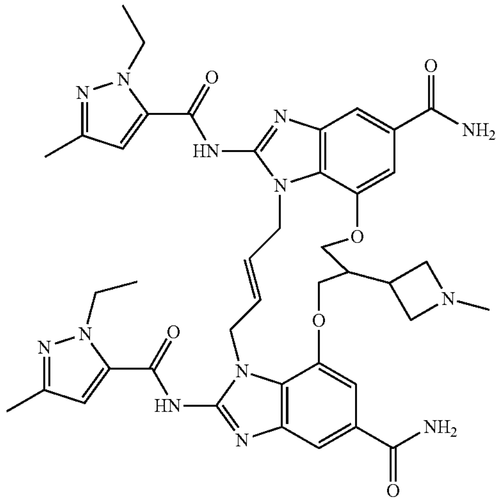 | (E)-1,15-bis(1-ethyl-3-methyl-1H-pyrazole-5-carboxamido)-8-(1-methylazetidin-3-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 34) |
| 35 | 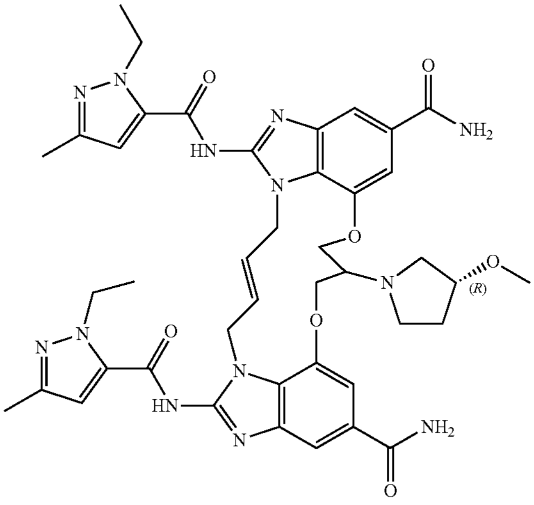 | (R,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 35) |

-continued

| Ex. No | Structure | IUPAC Name |
|---|---|---|
| 36 | 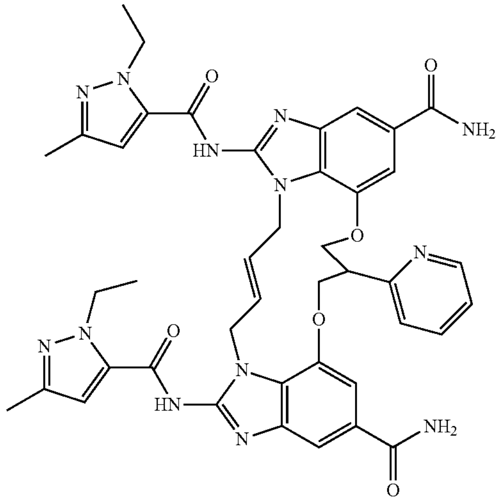 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(c1ccccn1)CO3] | (E)-1,15-bis(1-ethyl-3-methyl-1H-pyrazole-5-carboxamido)-8-(pyridin-2-yl)-8,9,16,19-tetrahydro-7H-6,10-dioxa-2,14,15a,19a-tetraazacyclopentadeca[3,2,1-cd:8,9,10-c'd']diindene-4,12-dicarboxamidexamide (Compound 36) |

In a further embodiment, the present invention provides a pharmaceutical composition comprising the compound of Formula (I), Formula (Ia), Formula (Ib) or pharmaceutically acceptable salts thereof and at least one or more pharmaceutically acceptable excipient.

In a further embodiment, the present invention provides a compound of Formula (I), Formula (Ia), Formula (Ib) or pharmaceutically acceptable salts thereof for use in the treatment of a disease or condition in which activation of STING is beneficial.

In a further embodiment, the present invention provides the use of a compound or pharmaceutical composition of Formula (I), Formula (Ia), Formula (Tb) or pharmaceutically acceptable salts thereof in the manufacture of a medicament for the treatment of a disease or condition in which activation of STING is beneficial.

In a further embodiment, the present invention provides a method of treatment of a disease or condition in which activation of STING is beneficial in a subject comprising administering a therapeutically effective amount of a compound of Formula (I), Formula (Ia), Formula (Ib) or its pharmaceutically acceptable salt thereof.

In a further embodiment, the invention provides a method of treatment of disease or condition selected from cancer and infectious diseases, in a mammal in need thereof, which comprises administering to such mammal a therapeutically effective amount of a compound of Formula (I), Formula (Ia), Formula (Ib) or its pharmaceutically acceptable salt thereof.

In a further embodiment, the invention provides a method of treatment of cancer such as solid tumors, leukemias and lymphomas.

In a further embodiment, the invention provides a method of treatment of infectious diseases such as viral infection or bacterial infection.

In a further embodiment, the invention provides a composition comprising compound of Formula (I), Formula (Ia), Formula (Tb) or pharmaceutically acceptable salts thereof, and one or more additional therapies.

In a further embodiment, the invention provides a composition comprising compound of Formula (I), Formula (Ia), Formula (Tb) or pharmaceutically acceptable salts thereof, and one or more additional therapies such as chemotherapy, immunotherapy or radiotherapy.

In a further embodiment, the invention provides a vaccine adjuvant comprising a compound of Formula (I), Formula (Ia), Formula (Tb) or pharmaceutically acceptable salts thereof.

In a further embodiment, the invention provides a vaccine composition comprising compound of Formula (I), Formula (Ia), Formula (Tb) or pharmaceutically acceptable salts thereof, and an antigen or antigen composition.

DETAILED DESCRIPTION OF THE INVENTION

General terms used in formula can be defined as follows; however, the meaning stated should not be interpreted as limiting the scope of the term per se.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term 'perhaloalkyl', as used herein, means an alkyl group as defined hereinabove wherein all the hydrogen atoms of the said alkyl group are substituted with halogen. The perhaloalkyl group is exemplified by trifluoromethyl, pentafluoroethyl, and the like.

The term "aromatic ring" as used herein, refers to a monocyclic aromatic hydrocarbon ring system.

The term "heteroaromatic ring" as used herein, refers to a 5-6 membered monocyclic aromatic ring system having 1-2 ring heteroatoms selected from O, N, or S.

The term "cycloalkyl" or 'carbocycle' refers to a non-aromatic mono or multicyclic ring system having 3 to 12 carbon atoms, such as cyclopropyl, cyclobutyl, cyclopentyl, cyclohexyl and the like. Unless set forth or recited to the contrary, all cycloalkyl groups described or claimed herein may be substituted or unsubstituted.

The term "$C_3$-$C_5$ monocyclic cycloalkyl" refers to a substituted or unsubstituted non-aromatic monocyclic ring system having 3 to 5 carbon atoms, such as cyclopropyl, cyclobutyl, cyclopentyl, and the like.

The term "aromatic carbocyclic ring", as used herein, refers to aromatic hydrocarbon ring system. Examples include benzene ring, and the like.

The term 'aryl', as used herein, refers to a monovalent monocyclic, bicyclic or tricyclic aromatic hydrocarbon ring system. Examples of aryl groups include phenyl, naphthyl, anthracenyl, fluorenyl, indenyl, azulenyl, and the like.

The term 'heteroaryl', as used herein, refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic.

The term "heterocycle" or "heterocyclyl", unless otherwise specified, refers to substituted or unsubstituted non-aromatic, monocyclic, bicyclic, tricyclic or bridged/fused/spiro ring system having 3- to 15-membered ring which consists of carbon atoms and with one or more (e.g., 2 or 3) heteroatom(s) independently selected from N, O, S, P(O)($OR^4$), P(O)($R^{4a}$) or $S(O)_2$. The point of attachment may be from any suitable carbon or nitrogen.

The term 'oxo' means a divalent oxygen (=O) attached to the parent group. For example oxo attached to carbon forms a carbonyl, oxo substituted on cyclohexane forms a cyclohexanone, and the like.

The term "tautomer" or "tautomeric form" refers to structural isomers of different energies which are interconvertible via a low energy barrier. For example, proton tautomers (also known as prototropic tautomers) include interconversions via migration of a proton, such as keto-enol isomerizations. Valence tautomers include interconversions by reorganization of some of the bonding electrons.

The term "geometric isomer" refers to E or Z geometric isomers (for example, cis or trans) of double bond.

All tautomeric forms and their possible geometrical isomers, including, but not limiting to Formula (s), Formula (r), and Formula (t), of the formulas and compounds described herein are intended to be encompassed within the scope of the present invention.

Formula (s)

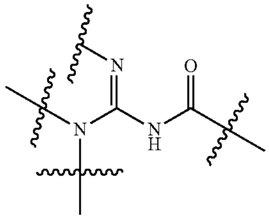

-continued

Formula (r)

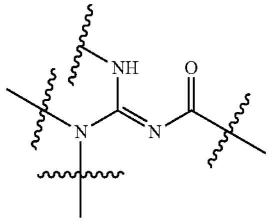

Formula (t)

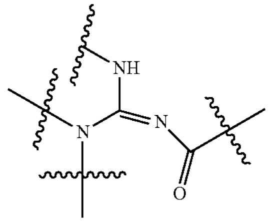

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

The term "treating" or "treatment" of a state, disease, disorder, condition or syndrome includes: (a) preventing or delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "subject" includes mammals, preferably humans and other animals, such as domestic animals; e.g., household pets including cats and dogs.

A "therapeutically effective amount" refers to the amount of a compound that, when administered to a subject in need thereof, is sufficient to cause a desired effect. The "therapeutically effective amount" will vary depending on the compound, the disease and its severity, age, weight, physical condition and responsiveness of the subject to be treated.

Compounds disclosed herein and their tautomeric forms, stereoisomers, prodrugs may be prepared, for example, by techniques well known in the organic synthesis and familiar to a practitioner ordinarily skilled in art of this invention. In addition, the processes described herein may enable the synthesis of the compounds of the present invention. However, these may not be the only means by which the compounds described in the invention may be synthesized. Further, the various synthetic steps described herein may be performed in alternate sequences in order to furnish the desired compounds.

In a further aspect, of the present invention, there is provided a compound of Formula (I), Formula (Ia), and Formula (Ib), or a pharmaceutically acceptable salt thereof for use in the treatment of a disease or condition in which activation of STING is beneficial.

In a further aspect of the present invention, there is provided the use of a compound or pharmaceutical composition of Formula (I), Formula (Ia), and Formula (Ib), or a pharmaceutically acceptable salt thereof for the manufacture of a medicament for use in the treatment of a disease or condition in which activation of STING is beneficial.

In a further aspect of the present invention, there is provided a method of the treatment of a disease or condition in which activation of STING is beneficial in a subject comprising administering a therapeutically effective amount of a compound of Formula (I), Formula (Ia), and Formula (Ib), or its pharmaceutically acceptable salt thereof.

In a further aspect the invention provides a method of treatment of disease or condition selected from cancer and infectious diseases, in a mammal in need thereof, which comprises administering to such mammal a therapeutically effective amount of a compound of Formula (I), Formula (Ia), and Formula (Ib), or its pharmaceutically acceptable salt thereof.

In a further aspect the invention provides a method of treatment cancer such as solid tumors, leukemias and lymphomas.

In a further aspect the invention provides a method of treatment of infectious diseases such as viral infection or bacterial infection. Examples of solid tumors which may be treated with the compounds of present invention include, but are not limited to, breast cancer, pancreatic cancer, lung cancer, colon cancer, coloretal cancer, brain cancer, renal cancer, testicular cancer, cancer of urethra, rectal cancer, cancer of fallopian tubes, penile cancer, vaginal cancer, stomach cancer, skin cancer, melanoma, liver cancer, gastrointestinal stromal tumors, urothelial cancer, thyroid cancer, parathyroid gland cancer, adrenal cancer, bone cancer, oral cancer, ovarian cancer, uterine cancer, head and neck sqamous cell carcinoma, endometrial cancer, gall bladder cancer, bladder cancer, orophyrangeal cancer, lymph node cancer, glioblastoma, astrocytoma, glioblastoma multiforme or sarcomas of soft tissue, fibrosarcoma, chondrosarcoma, hemangioma, teratoma, lipoma, myxoma, fibroma, rhabdomyoma, teratoma, cholangiocarcinoma, Ewing's sarcoma. Examples of leukemia, which may be treated with the compounds of present invention include, but are not limited to Lymphoblastic T cell leukemia, Chronic myelogenous leukemia, Acute lymphoblastic T cell leukemia, Acute myelobastic leukemia, Hairy-cell leukemia, Chronic neutrophilic leukemia, Mantle cell leukemia, Acute megakaryocytic leukemia, Multiple myeloma, Megakaryoblastic leukemia, Erythroleukemia, Plasmacytoma, Promyelocytic leukemia, Chronic myelomonocytic leukemia, Myelodysplastic syndrome, Myelofibrosis, Chronic myelogenous leukemia, Polycythemia vera, Thrombocythemia, Chronic lymphocytic leukemia, Prolymphocytic leukemia, Hairy cell leukemia, Waldenstrom's macroglobulinemia, Castleman's disease, Chronic neutrophilic leukemia, Immunoblastic large cell leukemia, Plasmacytoma, and Leukemias in any other parts of body. Examples of lymphoma, which may be treated with the compounds of present invention include, but are not limited to, Hodgkin's disease, non-Hodgkin's lymphoma, Follicular lymphoma, Mantle cell lymphoma, Burkitt's lymphoma, Lymphoblastic T-cell lymphoma, Marginal zone lymphoma, Cutaneous T cell lymphoma, CNS lymphoma, Small lymphocytic lymphoma, Lymphoplasmacytic lymphoma, Diffuse large B-cell lymphoma (DLBCL), Peripheral T-cell lymphoma, Anaplastic large cell lymphoma, Primary mediastinal lymphoma, Mycosis fungoides, Small non-cleaved cell lymphoma, Lymphoblastic lymphoma, Immunoblastic lymphoma, Primary effusion lymphoma and HIV associated (or AIDS related) lymphomas. Examples of viral infection which may be treated with the compounds of present invention include, but are not limited to, human immune deficiency virus (HIV), Human papillomavirus (HPV), hepatitis C virus (HCV), hepatitis B virus (HBV), Influenza (Orthomyxoviridae), Alphavirus, Rotavirus, Sendai, vaccinia, respiratory synctical virus, Lassa virus (Arenaviridae), Rabies virus (Rhabdoviridae), West nile virus, Dengue virus, Japanese encephalitis virus, and other Flaviviridae, RNA virus, DNA virus, virus belonging to the family of Alphaflexiviridae, Astroviridae, Alphatetraviridae, Alvernaviridae, Asfarviridae, Ampullaviridae, Adenoviridae, Ascoviridae, Betaflexiviridae, Bromoviridae, Barnaviridae, Bicaudaviridae. Baculoviridae Closteroviridae, Caliciviridae, Carmotetraviridae, Clavaviridae, Corticoviridae, Dicistroviridae, Endornaviridae, Filoviridae, Globuloviridae, Guttaviridae, Geminiviridae, Hytrosaviridae, Leviviridae, Luteoviridae, Lipothrixviridae, Mesoniviridae, Marnaviridae, Metaviridae, Malacoherpesviridae, Nodaviridae, Nyamiviridae, Nimaviridae, Nanoviridae, Piconaviridae, Partitiviridae, Picobirnaviridae, Paramyxoviridae, Poxviridae, Pandoraviridae, Polymaviridae, Phycodnaviridae, Papillomaviridae, Polydnaviruses, Polymaviridae, Permutotetraviridae, Potyviridae, Retroviridae, Siphoviridae, Spharolipoviridae, Virgaviridae, Togaviridae, Turriviridae, Tectiviridae. Examples of bacterial infection which may be treated with the compounds of present invention include, but are not limited to, infections caused by bacteria belonging to *Brucella, Clostridium, Clostrodium, Campylobacter, Enterococcus, Fransicella, Listeria, Legionella, Mycobacteria, Pseudomonas, Salmonella, Staphylococcus, Yersinia* genus. In a further aspect, the invention provides a composition comprising compound of Formula (I), Formula (Ia), and Formula (Ib), or its pharmaceutically acceptable salt thereof, and one or more additional therapies.

In a further aspect, the invention provides a composition comprising compound of Formula (I), Formula (Ia), and Formula (Ib), or a pharmaceutically acceptable salt thereof, and one or more additional therapies such as chemotherapy, immunotherapy or radiotherapy.

Chemotherapy comprises administering one or more additional chemotherapeutic agents that may be used in combination with the compounds of Formula (I), Formula (Ia), and Formula (Ib), or a pharmaceutically acceptable salt thereof. chemotherapeutic agents that may be used in combination includes topoisomerase II inhibitors, anti-tumor antibiotics, anti-metabolites, retinoids, antiviral agents, abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-tbutylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Immunotherapy comprises administering one or more additional immunostimulatory agents that may be used in combination with the compound of Formula (I), Formula (Ia), and Formula (Ib), or a pharmaceutically acceptable salt thereof. Immunostimulatory agents that may be used in combination herein includes vaccine adjuvants, such as Toll-like receptor agonists, T-cell checkpoint blockers, CTLA4, PD-1, PD-L1, TIM3, OX40, LAG3, B7-H3, GITR, 4-1BB, ICOS, CD40 and KIR antibody. Examples of CTLA-4 and PD-1 antagonists include, but are not limited to, ipilimumab, tremelimumab, nivolumab, pembrolizumab, CT-011, AMP-224, and MDX-1106.

In a further aspect the invention provides a vaccine adjuvant comprising a compound of Formula (I), Formula (Ia), and Formula (Ib), or a pharmaceutically acceptable salt thereof.

In a further aspect the invention provides a vaccine composition comprising compound of Formula (I), Formula (Ia), and Formula (Ib), or a pharmaceutically acceptable salt thereof, and an antigen or antigen composition.

Antigens and adjuvants that may be used in combination with the compound of Formula (I), Formula (Ia), and Formula (Ib), or a pharmaceutically acceptable salt thereof disclosed herein include B7 costimulatory molecule, interleukin-2, interferon-α, interferon-γ, GM-CSF, CTLA-4 antagonists, OX-40 agonist, CD40 agonist, sargramostim, levamisol, vaccinia virus, Bacille Calmette-Guerin (BCG), liposomes, alum, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-T) agonists such as poly I:C, used separately or in combination with the described compositions are also potential adjuvants.

The pharmaceutical compositions may be administered by a variety of means including non-parenterally, parenterally, by inhalation spray, topically, or rectally in formulations containing pharmaceutically acceptable carriers, adjuvants and vehicles. Intra-tumoral (directly into the tumor mass) or peri-tumoral (around the tumor mass) administration of the compounds of the present invention.

General Methods of Preparation

The compound of formula described herein may be prepared by techniques known in the art. In addition, the compound of formula described herein may be prepared by following the reaction sequence as depicted in Scheme-1 and Scheme-2. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compound of formula in described in these schemes, unless otherwise specified, are also encompassed within the scope of this invention.

The processes described herein may enable the synthesis of the compounds of the present invention. However, these may not be the only means by which the compounds described in the invention may be synthesized. Further, the various synthetic steps described herein may be performed in alternate sequences to afford the desired compounds.

Scheme 1

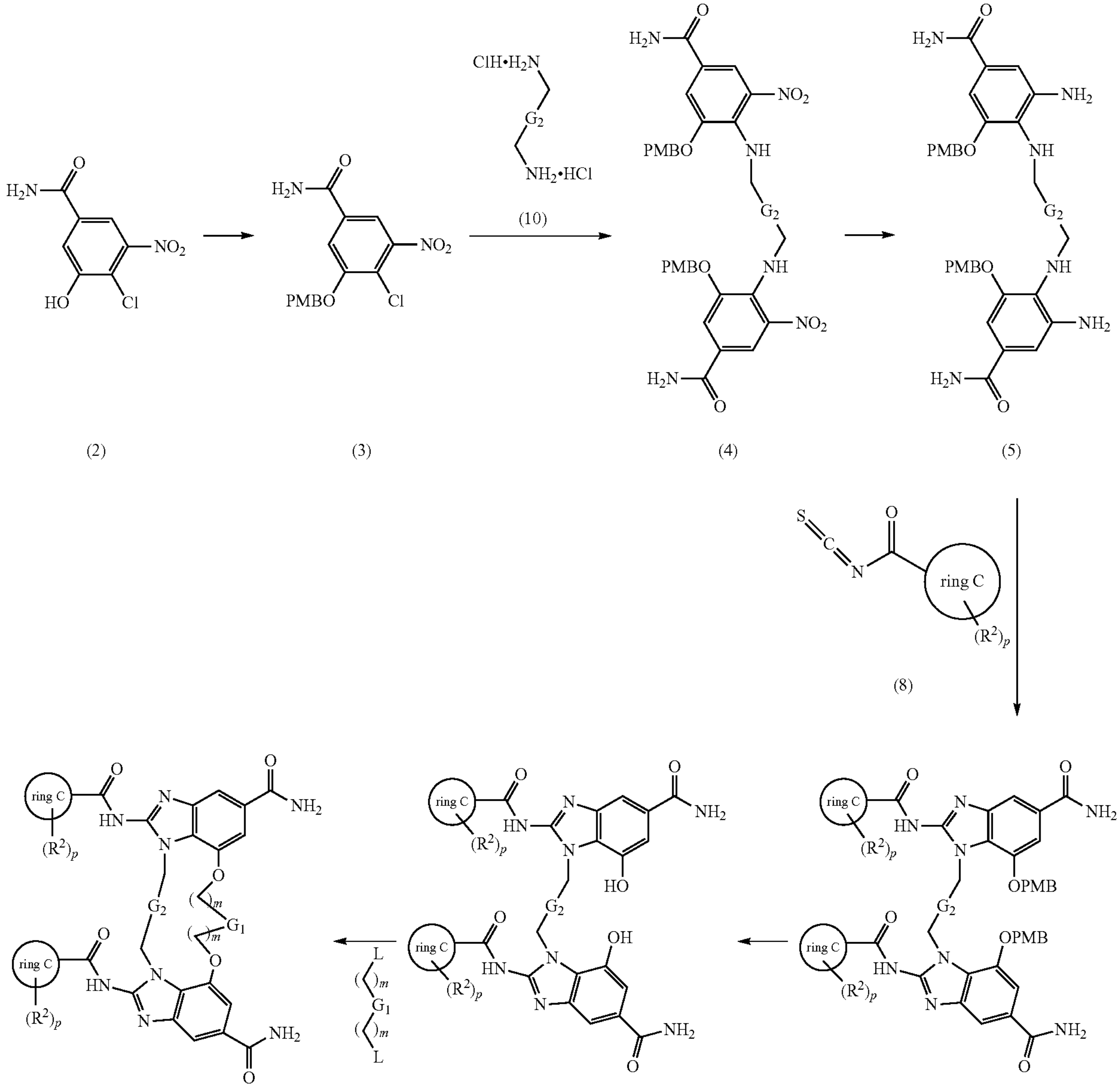

(2) (3) (4) (5)

(8)

(I-A) (9) (7) (6)

Scheme 1 shows a method of preparation of the compound of the formula (I-A) [wherein ring C, m, $G_1$, $G_2$, p and $R^2$ are as defined earlier for Formula 1] from the compound of formula (2).

The compound of the formula (2), is reacted with 1-(chloromethyl)-4-methoxybenzene in presence of base such as cesium carbonate, potassium carbonate, in solvents such as dimethyl formamide, acetonitrile, THF or acetone to obtain to obtain the compound of formula (3).

The compound of the formula (3) as obtained in the previous step is reacted with compounds of formula (10) in presence of base such as DIPEA in solvents like ethanol, methanol, THF or DMSO to obtain the compounds of formula (4).

The compounds of the formula (4) is reacted with sodium dithionite in solvents such as methanol, ethanol or THF to obtain the compounds of formula (5). Coupling of compounds of the formula (5) with compounds of formula (8), by using EDC and base such as triethyl amine or diisopropyl amine in solvents like dimethyl formamide or tetrahydrofuran to give compounds of formula (6).

The compounds of the formula (6) as obtained in the previous step was treated with acid like trifluoracetic acid or hydrochloric acid to deprotect the PMB group and so as to obtain the compounds of formula (7)

The compounds of the formula (7) as obtained is reacted with compounds of formula (9), where, L is halogen (Chloro/bromo) or -OMs or -OTs in presence of base such as sodium hydroxide, sodium hydride, potassium carbonate or caesium carbonate in solvents like tetrahydrofuran or dimethyl formamide at a temperature of about 30-80° C. or higher to afford the compounds of formula (I-A).

Scheme 2

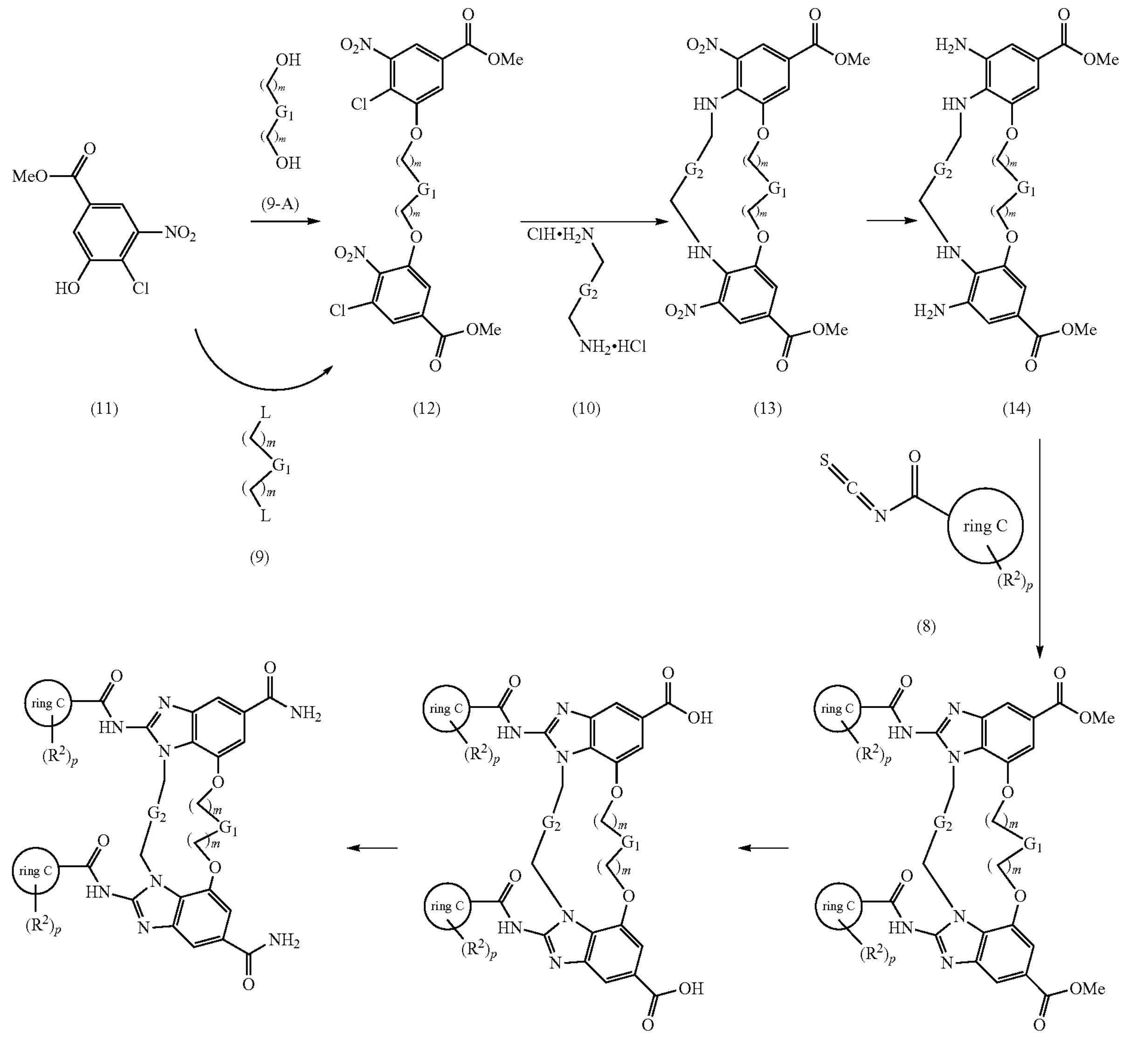

(11) (9) (12) (10) (13) (14) (8)

(I-A) (16) (15)

Scheme 2 shows a method of preparation of the compound of the formula (I-A) [wherein ring C, m, $G_1$, $G_2$, p and $R^2$ as defined earlier for Formula 1] from the compound of formula (11).

The compound of formula (11) was prepared according to the procedure described in WO2017/100594. The compound of the formula (11), is reacted with compounds of formula (9-A) under Mitsunobu condition in presence of reagents like DIAD or DEAD and TPP in solvents such as dimethyl formamide, acetonitrile or THF to obtain the compounds of formula (12).

The compound of the formula (11) is alternatively can be reacted with compounds of formula (9), where, L is halogen (Chloro/bromo) or -OMs or -OTs in presence of base such as sodium hydride, potassium carbonate or caesium carbonate in solvents like tetrahydrofuran or dimethyl formamide at a temperature of about 30-80° C. or higher to afford the compounds of formula (12).

The compounds of the formula (12) as obtained in the previous step is reacted with compounds of formula (10) in presence of base such as DIPEA in solvents like ethanol, methanol, THF or DMSO to obtain the compounds of formula (13).

The compounds of the formula (13) is reacted with sodium dithionite in solvents such as methanol ethanol or THF to obtain the compounds of formula (14). Coupling of compounds of the formula (14) with compounds of formula (8), by using EDC and base such as triethyl amine or diisopropyl amine in solvents like dimethyl formamide or tetrahydrofuran to give compounds of formula (15).

The compounds of the formula (15) as obtained in the previous step was treated with base like lithium hydroxide or sodium hydroxide for hydrolysis to obtain the compounds of formula (16).

The compounds of the formula (16) is reacted with coupling reagent like TBTU or EDC and ammonium chloride in solvents like tetrahydrofuran, dimethyl formamide to afford the compounds of formula (I-A).
Scheme 3
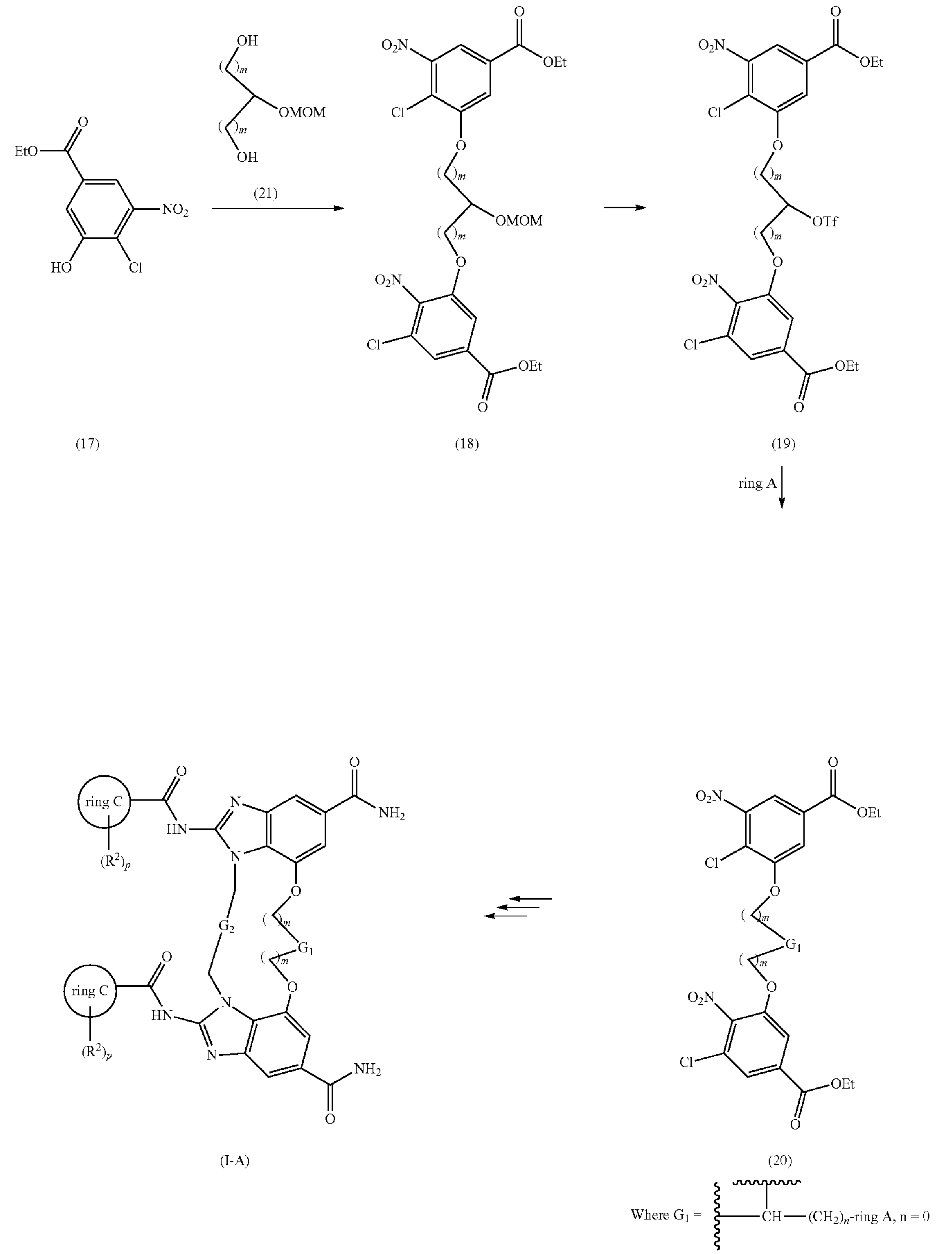
(17) (18) (19) (20) (I-A)

Scheme 3 shows a method of preparation of the compound of the formula (I-A) [wherein ring C, m, $G_1$, $G_2$, p and $R^2$ as defined earlier for Formula 1] from the compound of formula (17).

The compound of the formula (17), is reacted with compounds of formula (21) under Mitsunobu condition in presence of reagents like DIAD or DEAD and TPP in solvents such as dimethyl formamide, acetonitrile or THF to obtain the compounds of formula (18).

The compounds of the formula (18) is reacted with HCl in dioxane in solvents such as chlorinated solvent or tehtrahydrofuran to deprotect the methoxy methyl (MOM) group which upon further treatment with trifluoromethanesulfonic anhydride in presence of base such as 2,6-lutidine to give the compounds of formula (19).

The compounds of the formula (19) is reacted with ring A in presence of base such as triethyl amine in solvents like tehtrahydrofuran or chlorinated solvent to afford the compounds of formula (20).

The compounds of the formula (20) can be converted to the compounds of formula (I-A) by the procedures analogously depicted in the Scheme 2 for the conversion of compounds of formula (12) to the compounds of formula (I-A).

Scheme 4

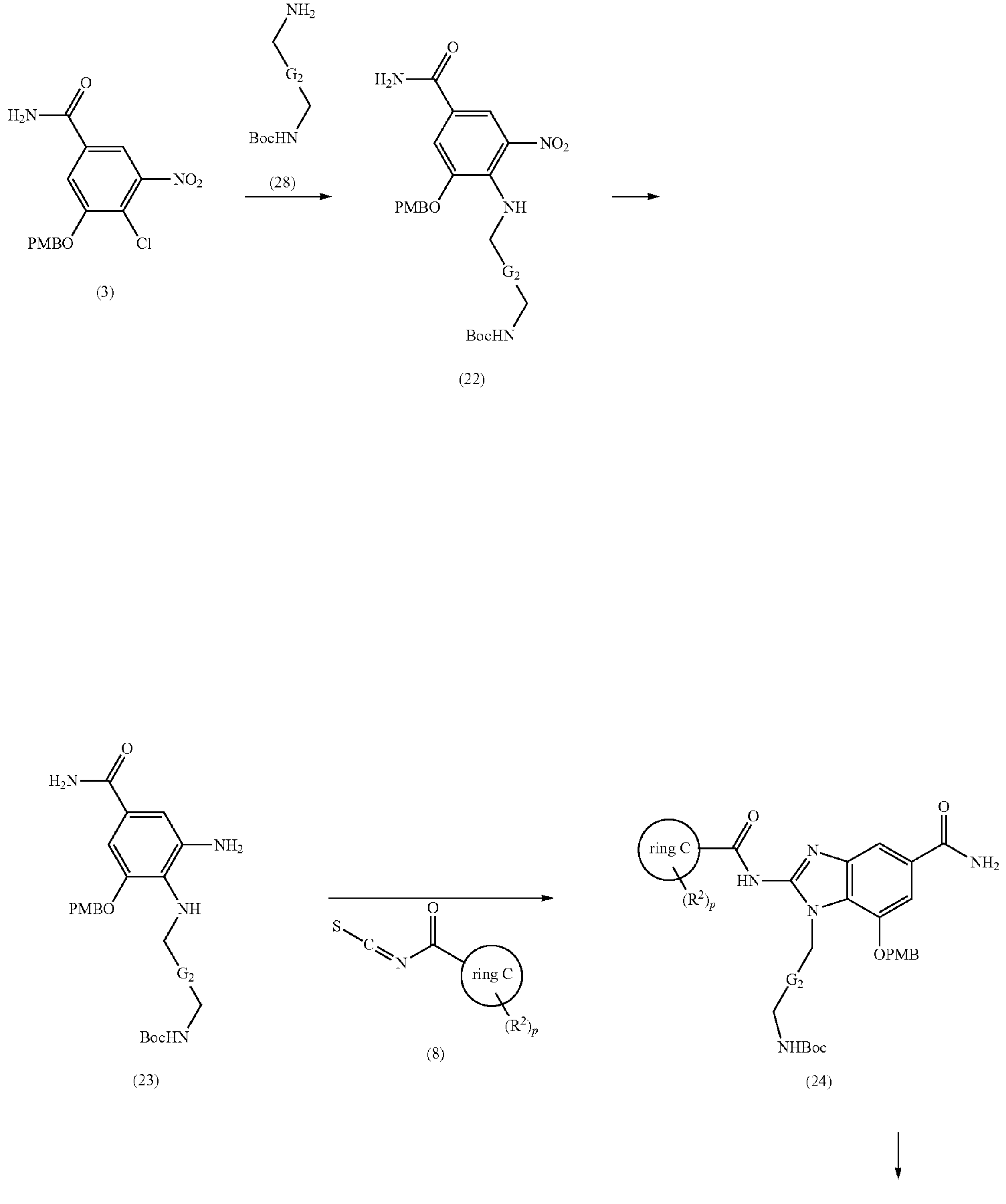

(3) (28) (22)

(23) (8) (24)

-continued

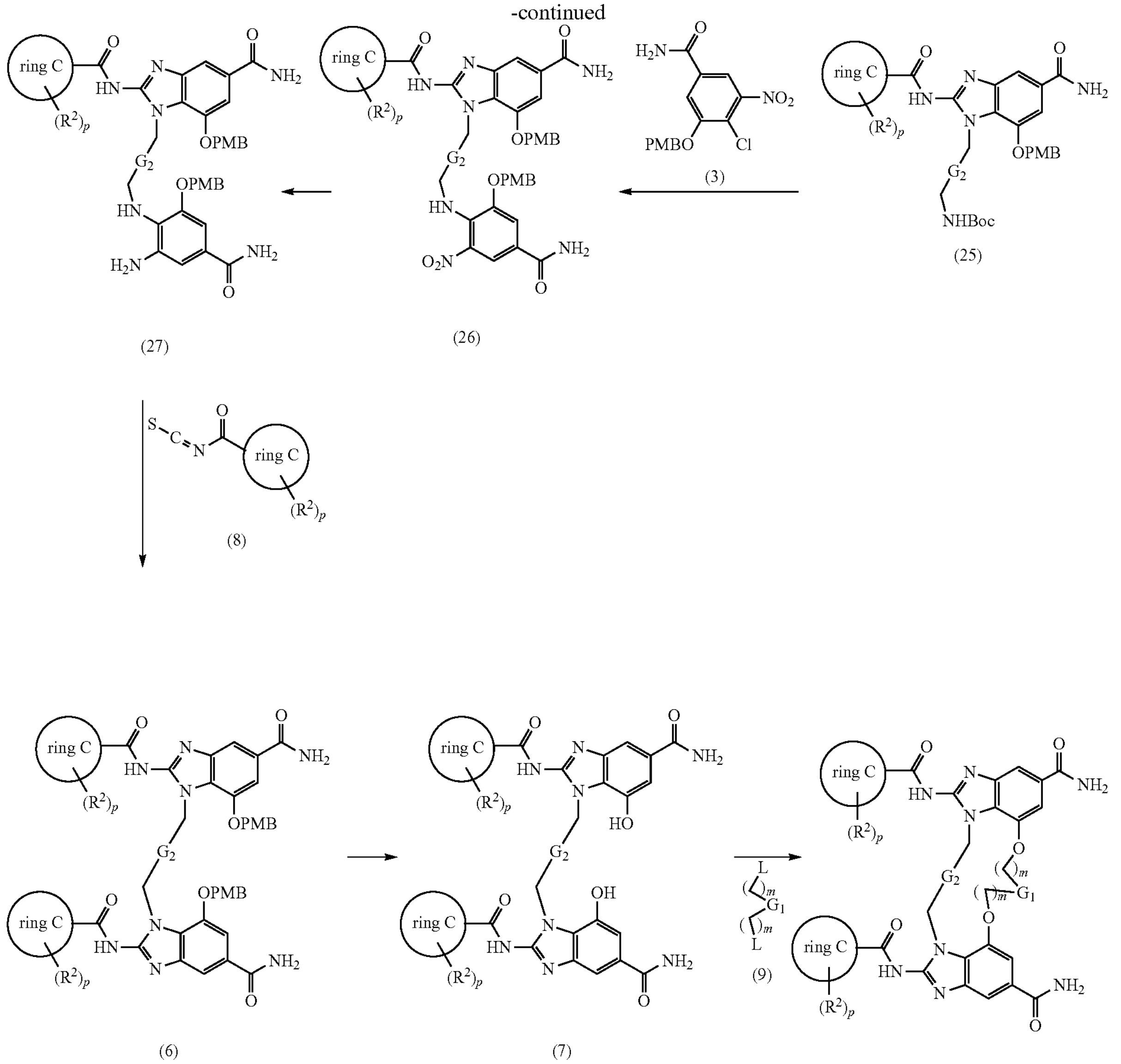

(27) (26) (3) (25)

(8)

(6) (7) (9)

(I-A)

Scheme 4 shows a method of preparation of the compound of the formula (I-A) [wherein ring C, m, $G_1$, $G_2$, p and $R^2$ as defined earlier for Formula 1] from the compound of formula (3).

The compound of the formula (3) is reacted with compound of formula (28) in presence of base such as DIPEA in solvents like ethanol, methanol, THF or DMSO to obtain the compounds of formula (22).

The compounds of the formula (22) is reacted with sodium dithionite in solvents such as methanol, ethanol or THF to obtain the compounds of formula (23). Coupling of compounds of the formula (23) with compounds of formula (8), by using EDC and base such as triethyl amine or diisoproyl amine in solvents like dimethyl formamide or tetrahydrofuran to give compounds of formula (24), which on Boc deprotection using HCl in dioxane to give compounds of formula (25).

The compounds of the formula (25) as obtained in the previous step is reacted with compound of formula (3) in presence of base such as DIPEA in solvents like ethanol, methanol, THF or DMSO to obtain the compounds of formula (26).

The compounds of the formula (26) is reacted with sodium dithionite in solvents such as methanol, ethanol or THF to obtain the compounds of formula (27). Coupling of compounds of the formula (27) with compounds of formula (8), by using EDC and base such as triethyl amine or diisopropyl amine in solvents like dimethyl formamide or tetrahydrofuran to give compounds of formula (6).

The compounds of the formula (6) as obtained in the previous step was treated with acid like trifluoracetic acid or hydrochloric acid to deprotect the PMB group to obtain the compounds of formula (7)

The compounds of the formula (7) as obtained is reacted with compounds of formula (9), where, L is halogen (Chloro/bromo) or -OMs or -OTs in presence of base such as sodium hydroxide, sodium hydride, potassium carbonate or caesium carbonate in solvents like tetrahydrofuran, dimethyl formamide at a temperature of about 30-80° C. or higher to afford the compounds of formula (I-A).

Scheme 5

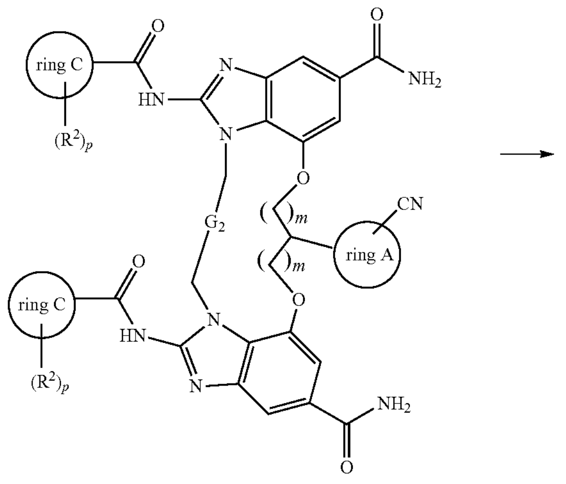

(I-B)

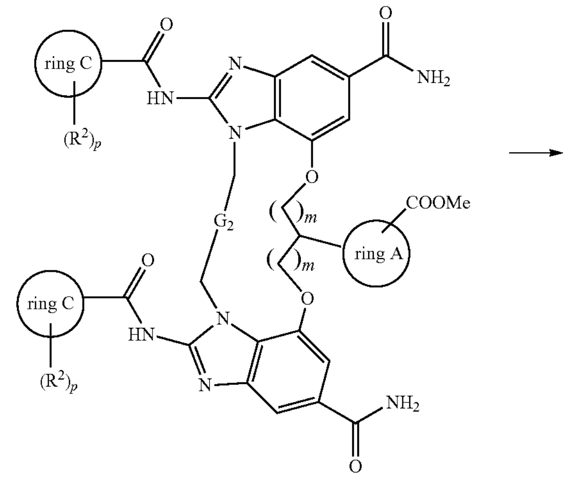

(I-C)

-continued

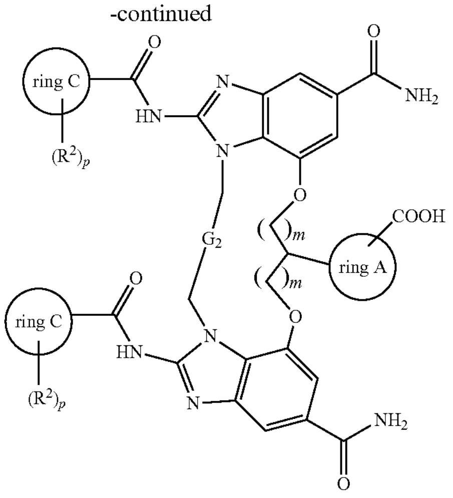

(I-D)

Wherein: ring A is heterocycle substituted with -CN

Scheme 5 shows a method of preparation of the compounds of the formula (I-D) [wherein ring C, m, $G_2$, p and $R^2$ as defined earlier for Formula 1] from the compounds of formula (I-B).

The compounds of the formula (I-B), is reacted with HCl in methanol to obtain the compounds of formula (I-C), which was treated with base like lithium hydroxide or sodium hydroxide for hydrolysis to obtain the compounds of formula (I-D).

ABBREVIATIONS

DMF: dimethylformamide
DMSO: dimethyl sulfoxide
THF: tetrahydrofuran
CDI: 1,1'-Carbonyldiimidazole
EDC: 1-Ethyl-3-(3-dimethylaminopropyl)carbodiimide
TBTU: 2-(1H-Benzotriazole-1-yl)-1,1,3,3-tetramethyluronium tetrafluoroborate
HATU: 1-[Bis(dimethylamino)methylene]-1H-1,2,3-triazolo[4,5-b]pyridinium 3-oxide hexafluorophosphate
DIPEA: diisopropyl amine
NMP: N-Methyl-2-pyrrolidone
TEA: triethyl amine
KI: potassium iodide
DCM: dichloromethane
MeOH: methanol
MOM: methoxy methyl
Ms: methanesulfonyl
Ts: 4-methylbenzenesulfonyl
PMB: 4-methoxy benzyl
DEAD: diethyl azodicarboxylate
DIAD: diisopropyl azodicarboxylate
TPP: triphenyl phosphine Some of the representative examples of the present invention were prepared by following one or more reaction schemes as described above.

The invention is further illustrated by the following examples which are provided merely to be exemplary of the invention and do not limit the scope of the invention. The examples set forth below demonstrate the synthetic procedures for the preparation of the relative compounds. Certain modifications and equivalents will be apparent to those skilled in the art and are intended to be included within the scope of the invention.

Nomenclature of the compounds of the invention is according to ChemDraw Professional 16.0. Structures of the intermediates as well as the final compounds were confirmed by spectral data.

EXPERIMENTAL

Synthesis of Intermediates:

Intermediate 1:

Synthesis of 4-chloro-3-hydroxy-5-nitrobenzamide

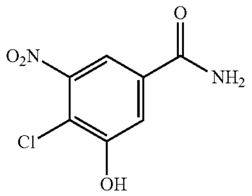 [SMILES: NC(=O)c1cc(O)c(Cl)c([N+](=O)[O-])c1]

Step 1: Synthesis of 4-chloro-3-methoxy-5-nitrobenzamide

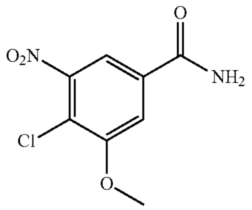

To a suspension of 4-chloro-3-methoxy-5-nitrobenzoic acid (Prepared by following procedure as reported in WO2017/100594, 20.0 g, 86 mmol) and N,N-dimethyl formamide (0.669 ml, 8.64 mmol) in dichloromethane (400 ml) was added oxalyl chloride (8.32 ml, 95 mmol) dropwise at 0° C. and the reaction mixture was stirred for 30 minutes at 40° C. Upon disappearance of starting material, reaction mixture was concentrated in vacuum and dissolved in 500 ml dichloromethane and cooled to 0° C. Ammonium hydroxide (135 ml, 864 mmol, 25% aqueous solution) was added dropwise and the reaction mixture was warmed to room temperature and stirred for 1 hr. Progress of the reaction was monitored by TLC. Upon completion, the reaction mass was concentrated under reduced pressure. The obtained solid was filtered, washed with water and dried under vacuum to afford the title compound (19.0 g, 95% yield).

LCMS (ESI): m/z 230.1 $(M+H)^+$ $^1$H NMR (400 MHz, DMSO-$d_6$) δ 8.31 (s, 1H), 8.06 (d, J=1.8 Hz, 1H), 7.89 (d, J=1.9 Hz, 1H), 7.79 (s, 1H), 4.02 (s, 3H).

Step 2: Synthesis of 4-chloro-3-hydroxy-5-nitrobenzamide (Intermediate 1)

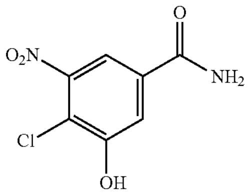 [SMILES: NC(=O)c1cc(O)c(Cl)c([N+](=O)[O-])c1]

4-chloro-3-methoxy-5-nitrobenzamide (Step 1, 18.5 g, 80 mmol) was co evaporated with toluene (4×10 ml) till complete dryness, and then was suspended in dichloromethane (250 ml) and stirred at room temperature. To the reaction was added 1M solution in dichloromethane of boron tribromide (481 ml, 481 mmol) in dropwise manner. The slurry was stirred for 60 hr at 40° C. under nitrogen. Reaction was monitored by 1H NMR. Upon completion, the volatiles were removed under reduced pressure till complete dryness. The reaction mass was cooled to −78° C. and wet ice was added slowly to the reaction mixture (till fuming stops). The reaction mixture was stirred at room temperature for 15 minutes. The precipitate was filtered and washed with water and dried thoroughly under vacuum to obtain the title compound as off-white solid (16.0 g, 92% yield).

LCMS (ESI): m/z 216.2 $(M+H)^+$ $^1$H NMR (400 MHz, DMSO-$d_6$) δ 11.50 (s, 1H), 8.16 (s, 1H), 7.92 (d, J=2.0 Hz, 1H), 7.72 (d, J=2.0 Hz, 1H), 7.63 (s, 1H).

Intermediate 2:

Synthesis of (1R,5S)-3-(1,3-dichloropropan-2-yl)-8-oxa-3-azabicyclo[3.2.1]octane

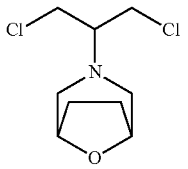 [SMILES: ClCC(CCl)N1CC2CCC(C1)O2]

Step-1: Synthesis of Diethyl 2-((1R,5S)-8-oxa-3-azabicyclo[3.2.1]octan-3-yl)malonate

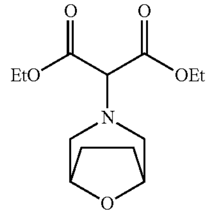 [SMILES: CCOC(=O)C(C(=O)OCC)N1CC2CCC(C1)O2]

To a stirred solution of diethyl 2-bromomalonate (5.0 g, 20.91 mmol), in chloroform (50 ml) was added 8-oxa-3-azabicyclo[3.2.1]octane hydrochloride (4.69 g, 31.4 mmol)

and TEA (14.58 ml, 105 mmol) at rt and heated the reaction mixture at 60° C. for 12 h. Reaction was monitored by using TLC. The reaction mixture was concentrated to get crude product which was purified by combi flash using 15-20% ethyl acetate in hexanes to get the title compound (3.5 g, 61.7% yield).

LCMS (ESI): m/z 271.08 $(M+H)^+$ $^1H$ NMR (400 MHz, DMSO-$d_6$) δ 4.20 (d, J=2.6 Hz, 3H), 4.15 (m, 4H), 2.70 (m, 2H), 2.61 (m, 2H), 1.92-1.74 (m, 2H), 1.74-1.64 (m, 2H), 1.20 (t, J=7.1 Hz, 6H).

Step-2: Synthesis of 2-((1R,5S)-8-oxa-3-azabicyclo [3.2.1]octan-3-yl)propane-1,3-diol

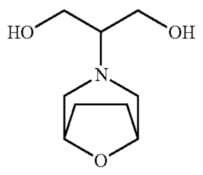

Diethyl 2-(8-oxa-3-azabicyclo[3.2.1]octan-3-yl)malonate (Step 1 Product, 3.50 g, 12.90 mmol) in THF (20 ml) was added to lithium aluminium hydride (2.448 g, 64.5 mmol) solution in THF (20 ml) at 0° C. The resulting solution was stirred at 25° C. for 5 h. The mixture was quenched by adding ethyl acetate 25 ml and sat. aq. NaCl solution dropwise. The solid obtained was filtered through celite pad and the filtrate was concentrated to get crude product which was purified by column chromatography using 10% methanol in dichloromethane to afford title compound (1.5 g, 62.1% yield).

LCMS (ESI): m/z 188.14 $(M+H)^+$ $^1H$ NMR (400 MHz, DMSO-$d_6$) δ 4.16 (m, 2H), 3.44 (m, 4H), 2.69 (m, 2H), 2.44 (m, 2H), 2.36 (m, 1H), 1.86-1.77 (m, 2H), 1.72-1.61 (m, 2H).

Step-3: Synthesis of (1R,5S)-3-(1,3-dichloropropan-2-yl)-8-oxa-3-azabicyclo[3.2.1]octane (Intermediate 2)

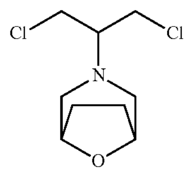 [SMILES: ClCC(CCl)N1CC2CCC(C1)O2]

To a stirred solution of 2-(8-oxa-3-azabicyclo[3.2.1]octan-3-yl)propane-1,3-diol (Step 2 Product, 0.50 g, 2.67 mmol) in THF (10 ml) was added thionyl chloride (0.780 ml, 10.68 mmol) dropwise at 0° C. and stirred the reaction mixture at 25° C. for 16 h. Reaction was monitored by LCMS.

Reaction mixture was concentrated to dryness and washed with diethyl ether to get salt. This salt was neutralized by adding 10% sodium bicarbonate and extracted with ethyl acetate. Ethyl acetate was concentrated to get free base which was purified by silica gel column chromatography using 5-10% ethyl acetate in hexanes to get the title compound (0.20 g, 33.4% yield).

LCMS (ESI): m/z 224.89 $(M+H)^+$ $^1H$ NMR (400 MHz, DMSO-$d_6$) δ 4.20 (m, 2H), 3.78 (m, 2H), 3.69 (m, 2H), 2.91 (q, J=6.3 Hz, 1H), 2.73 (dd, J=11.0, 2.0 Hz, 2H), 2.54 (d, J=1.9 Hz, 2H), 1.90-1.77 (m, 2H), 1.77-1.61 (m, 2H).

Intermediate 3:

Synthesis of (1R,5S)-3-(1,3-dichloropropan-2-yl)-8-oxa-3-azabicyclo[3.2.1]octane Step-1: benzyl 1-(2-fluoroethyl)-3-methyl-1H-pyrazole-5-carboxylate

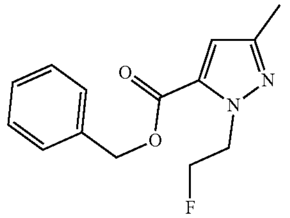 [SMILES: Cc1cc(C(=O)OCc2ccccc2)n(CCF)n1]

In a round bottom flask, benzyl 3-methyl-1H-pyrazole-5-carboxylate (20.0 g, 92 mmol), 2-fluoroethan-1-ol (6.52 g, 102 mmol) and triphenylphospine (31.5 g, 120 mmol) were dissolved into tetrahydrofuran (200 ml) followed by the dropwise addition of diisopropyl azadicarboxylate (23.38 ml, 120 mmol) into the reaction mixture. Reaction mixture was stirred at 25° C. for 60 min. Reaction was monitored by using TLC. Upon completion, the reaction was quenched by addition of water (50 ml) and extracted with ethyl acetate (250 ml×2). Organic layers were combined and washed with brine, dried over sodium sulphate and concentrated under reduced pressure to get crude, which was purified by combi flash chromatography (20% ethyl acetate in hexane) to yield the title compound as white solid (18 g, 74.2% yield).

LCMS (ESI): m/z 262.96 $(M+H)^+$ $^1H$ NMR (400 MHz, Chloroform-d) δ 7.47-7.32 (m, 5H), 6.71 (s, 1H), 5.33 (s, 2H), 4.93-4.79 (m, 3H), 4.71 (t, J=5.0 Hz, 1H), 2.30 (s, 3H).

Step-2: 1-(2-fluoroethyl)-3-methyl-1H-pyrazole-5-carboxylic acid

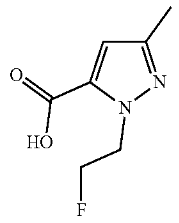

In a round bottom flask, benzyl 1-(2-fluoroethyl)-3-methyl-1H-pyrazole-5-carboxylate (step 1, 17.5 g, 66.7 mmol) was dissolved into tetrahydrofuran (50 ml) followed by the dropwise addition of lithium hydroxide (2.397 g, 100 mmol). Reaction mixture was stirred at 25° C. for 15 hrs. Reaction was monitored by using TLC. The reaction mixture was concentrated under reduced pressure and a sticky solid which was dissolved in water. Ether (100 ml) wash was given ti the aqueous solution and after separation, the aqueous layer PH was adjusted ~2 by 1N HCl. Solid was precipitated out, stirred for 15 min and filtered through Buchner funnel and washed with water. Obtained solid was dried under vacuum to get title compound as white solid (10 g, 87% yield).

LCMS (ESI): m/z 173.01 $(M+H)^+$ $^1H$ NMR (400 MHz, DMSO-$d_6$) δ 13.32 (s, 1H), 6.64 (s, 1H), 4.83-4.73 (m, 2H), 4.73-4.63 (m, 2H), 2.19 (s, 3H).

Step 3: Synthesis of 1-(2-fluoroethyl)-3-methyl-1H-pyrazole-5-carbonyl isothiocyanate (Intermediate 3)

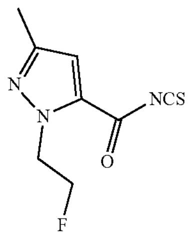

To a stirred solution of 1-(2-fluoroethyl)-3-methyl-1H-pyrazole-5-carboxylic acid (step 2,14.0 g, 81 mmol) in DCM (100 ml), were added DMF (6.30 μl, 0.081 mmol) and oxalyl chloride (7.83 ml, 89 mmol). During addition, the bubbling was observed. After 1 hr stirring the reaction mixture was concentrated under reduced pressure and the crude product (acid chloride) was proceeded further for the next reaction. In another RBF, potassium thiocyanate (7.90 g, 81 mmol) was dissolved in acetone (10 ml). The reaction mixture was cooled at 0-5° C. for 2 hrs. The above intermediate (acid chloride) was dissolved in acetone (10 ml) and added slowly to the reaction mixture. Upon completion, hexane (50 ml) was added to the reaction mixture and the reaction mixture was concentrated under vacuum. Repeated the same procedure for 3 times. After the concentration, hexane (50 ml) was added and filtered the solid compound. The resulting clear yellow filtrate was concentrated under vacuum. A crude product was purified by comb flash using ethyl acetate in hexane. The desired product was eluted by 0-5% of ethyl acetate, (10 gm, 58% yield).

$^1H$ NMR (400 MHz, Chloroform-d) δ 6.79 (s, 1H), 4.86-4.73 (m, 2H), 4.71-4.67 (m, 2H), 2.31 (s, 3H).

Example 1: (E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 1)

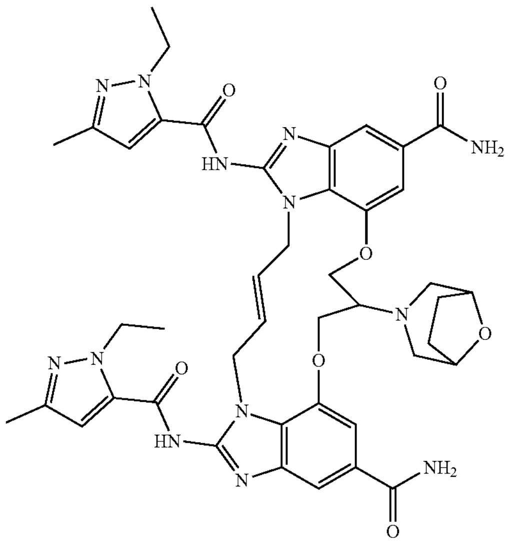 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC2CCC(C1)O2)CO3]

Step-1: Synthesis of 4-chloro-3-((4-methoxybenzyl)oxy)-5-nitrobenzamide

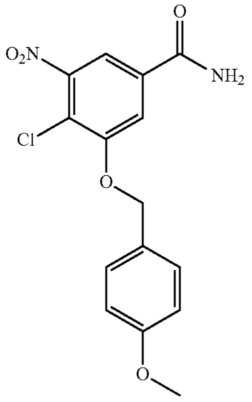 [SMILES: COc1ccc(COc2cc(C(N)=O)cc([N+](=O)[O-])c2Cl)cc1]

To a solution of 4-chloro-3-hydroxy-5-nitrobenzamide (Intermediate 1, 15.0 g, 69.3 mmol) in dimethylformaamide (75 ml) was added cesium carbonate (24.82 g, 76.0 mmol) and the mixture was stirred for 10 minutes at room temperature. 1-(chloromethyl)-4-methoxybenzene (11.39 g, 72.7 mmol) was added slowly at same temperature and the reaction mixture was stirred at 25° C. for 16 h. Reaction was monitored by TLC and LCMS. With vigorous stirring, water (300 mL) was added dropwise and the resulting solid was stirred for 15 minutes. The obtained solid was filtered and washed with water (200 ml). The compound was triturated with pentane to afford the title compound (14 g, 60.0% yield).

$^1H$ NMR (400 MHz, DMSO-$d_6$) δ 8.30 (s, 1H), 8.04 (m, 2H), 7.80 (s, 1H), 7.48-7.40 (m, 2H), 7.03-6.95 (m, 2H), 5.29 (s, 2H), 3.77 (s, 3H).

Step-2: Synthesis of (E)-4,4'-(but-2-ene-1,4-diylbis(azanediyl))bis(3-((4-methoxybenzyl) oxy)-5-nitrobenzamide)

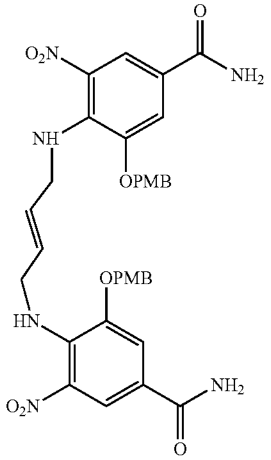

To a suspension of 4-chloro-3-((4-methoxybenzyl)oxy)-5-nitrobenzamide (Step 1 Product, 14.0 g, 41.6 mmol) in ethanol (100 ml) was added (E)-but-2-ene-1,4-diamine dihydrochloride (synthesized by methods known in the literature, 3.31 g, 20.79 mmol) and DIPEA (21.49 g, 166 mmol) and the mixture was allowed to stir at 100° C. for 48 hr in a sealed tube. Progress of the reaction was monitored by TLC and LCMS. Upon completion, the reaction mixture was concentrated under reduced pressure. The crude sticky solid was stirred with methanol (25 ml) for 15 minutes and the solid was filtered through Buchner funnel with bed wash of methanol (5 ml) to afford the title product (14.1 gm, 49.4% yield).

LCMS (ESI): m/z 687.28 $(M+H)^+$ $^1H$ NMR (400 MHz, DMSO-$d_6$) δ 8.20 (d, J=1.9 Hz, 3H), 8.03 (s, 3H), 7.77-7.65 (m, 4H), 7.38-7.29 (m, 4H), 6.94-6.84 (m, 4H), 5.40 (t, J=3.0 Hz, 2H), 5.02 (s, 4H), 3.99 (s, 4H), 3.73 (s, 6H).

Step-3: Synthesis of (E)-4,4'-(but-2-ene-1,4-diylbis(azanediyl))bis(3-amino-5-((4-methoxybenzyl)oxy)benzamide)

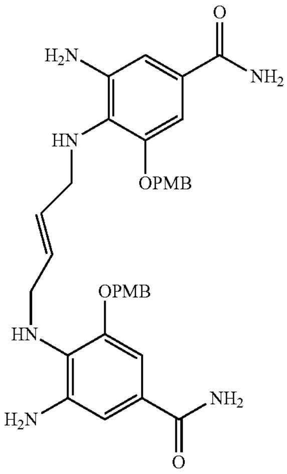

To a stirred suspension of (E)-4,4'-(but-2-ene-1,4-diylbis(azanediyl))bis(3-((4-methoxybenzyl)oxy)-5-nitrobenzamide) (Step 2 Product, 14.0 g, 20.39 mmol) in tetrahydrofuran (35 ml) and methanol (75 ml) was added Sodium dithionite (35.5 g solution in 38 ml of water, 204 mmol) at 0° C. Ammonium hydroxide (79.0 ml, 510 mmol) was added at same temperature. Reaction mixture was warmed to 25° C. and stirred at 25° C. for 15 hr. Progress of reaction was monitored by LCMS. Organic solvents were removed from the reaction mixture under vacuum. The crude product was dissolved in 15% of methanol in methylene dichloride (250 ml). A solid compound was precipitated out, stirred for 15 min. The solid was filtered out and the filtrate organic layer was concentrated udder reduced pressure. The compound was co-evaporated with toluene (100 ml) twice to remove the traces water to obtain the title compound (6.2 gm, 48.5% yield).

LCMS (ESI): m/z 627.46 $(M+H)^+$ $^1H$ NMR (400 MHz, DMSO-$d_6$) δ 7.63 (s, 1H), 7.47-7.31 (m, 5H), 7.21 (m, 3H), 7.01-6.80 (m, 9H), 5.61 (t, J=6.7 Hz, 2H), 4.97 (d, J=9.6 Hz, 4H), 4.65 (s, 1H), 3.81-3.73 (m, 3H), 3.72 (s, 6H), 3.48 (d, J=3.5 Hz, 4H).

Step-4: Synthesis of (E)-1,1'-(but-2-ene-1,4-diyl)bis(2-(1-ethyl-3-methyl-1H-pyrazole-5-carboxamido)-7-((4-methoxybenzyl)oxy)-1H-benzo[d]imidazole-5-carboxamide)

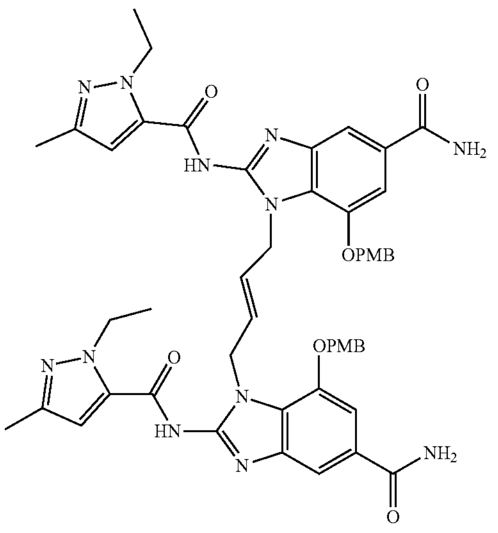

(E)-4,4'-(but-2-ene-1,4-diylbis(azanediyl))bis(3-amino-5-((4-methoxybenzyl)oxy)benzamide) (Step 3 Product, 6.0 g, 9.57 mmol) was dissolved in 50 mL DMF and the solution cooled to 0° C. and a solution of 1-ethyl-3-methyl-1H-pyrazole-5-carbonyl isothiocyanate (Synthesized by methods reported in the literature, 4.67 g, 23.93 mmol) in 5 mL DMF was added to it. The reaction mixture was stirred at 0° C. for 30 minutes after which 3-(ethyliminomethylideneamino)-N,N-dimethylpropan-1-amine; hydrochloride (5.51 g, 28.7 mmol) was added to the reaction mixture followed by the addition of diisopropylethylamine (10.02 mL, 57.4 mmol). The reaction mixture was allowed to warm to RT and stirred overnight. The progress of the reaction was monitored by LCMS and upon completion, the reaction mixture was concentrated under reduced pressure and water was added. The solid precipitate obtained was filtered to get the product (6.2 g, 68.2% yield).

LCMS (ESI): m/z 949.82 $(M+H)^+$ $^1H$ NMR (400 MHz, DMSO-$d_6$) δ 12.92 (s, 2H), 7.99 (s, 2H), 7.74 (s, 2H), 7.41 (m, 4H), 7.34-7.00 (m, 8H), 6.67 (d, J=8.4 Hz, 2H), 6.52 (s, 2H), 5.48 (s, 2H), 4.80 (m, 6H), 4.53 (d, J=7.5 Hz, 4H), 3.61 (s, 4H), 2.24-2.00 (m, 6H), 1.27 (m, 8H).

Step-5: Synthesis of (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide)

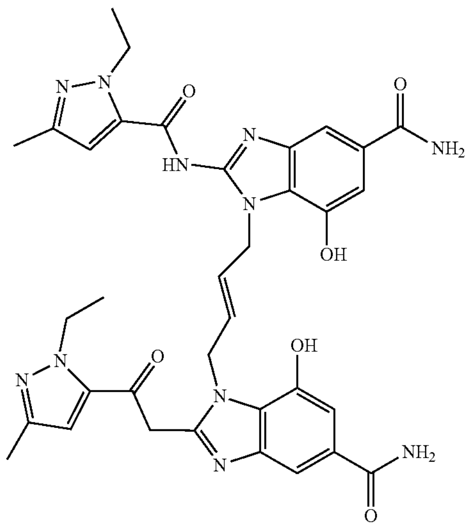 [SMILES: CCn1nc(C)cc1C(=O)Cc1nc2cc(C(N)=O)cc(O)c2n1C/C=C/Cn1c(NC(=O)c2cc(C)nn2CC)nc2cc(C(N)=O)cc(O)c21]

To a stirred solution of (E)-1,1'-(but-2-ene-1,4-diyl)bis(2-(1-ethyl-3-methyl-1H-pyrazole-5-carboxamido)-7-((4-methoxybenzyl)oxy)-1H-benzo[d]imidazole-5-carboxamide) (Step 4 Product, 5.80 g, 6.11 mmol) in 50 mL dichloromethane was added trifluoroacetic acid (50 ml, 306 mmol) at room temperature. The reaction mixture was stirred for 1 h and after the completion of the reaction as judged from TLC, the volatiles were concentrated, and water was added to the residue resulting in the precipitation of the crude product. The solid was filtered and washed with water and dried by azeotropic distillation with toluene. The dried crude product was purified by trituration successively with diethyl ether, dichloromethane and acetonitrile and filtered to obtain the product (4.0 gm, 92% yield).

LCMS (ESI): m/z 709.32 $(M+H)^+$ $^1H$ NMR (400 MHz, DMSO-$d_6$) δ 12.77 (s, 2H), 10.45 (m, 2H), 7.82 (s, 2H), 7.44 (m, 3H), 7.18 (m, 3H), 6.50 (s, 2H), 5.95 (s, 2H), 4.95 (s, 4H), 4.51 (d, J=7.0 Hz, 4H), 2.09 (m, 6H), 1.24 (t, J=7.1 Hz, 6H).

Step 6: Synthesis of (E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 1)

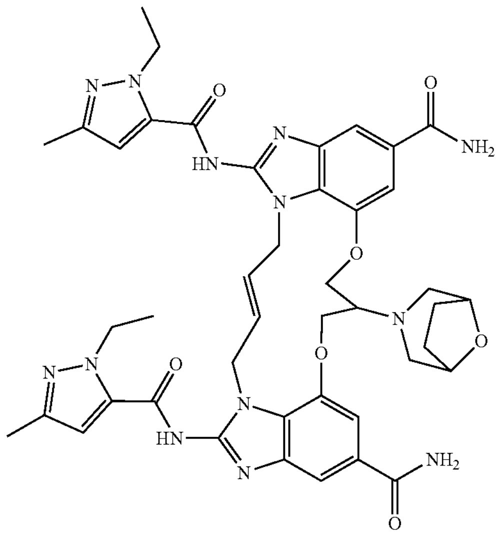 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC2CCC(C1)O2)CO3]

To a stirred solution of (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) (Step 5 Product, 200 mg, 0.282 mmol) in DMF (4 ml) was added 3-(1,3-dichloropropan-2-yl)-8-oxa-3-azabicyclo[3.2.1]octane (Intermediate 2, 95 mg, 0.423 mmol), sodium hydroxide (45.1 mg, 1.129 mmol) and potassium iodide (23.42 mg, 0.141 mmol). Then the reaction mixture was heated at 60° C. for 10 h. Reaction was monitored by LCMS. Reaction mixture was concentrated to dryness and washed with acetonitrile and purified by preparative HPLC to obtain the title compound (18 mg, 7.04% yield).

LCMS (ESI): m/z 860.68 $(M+H)^+$ $^1$H NMR (400 MHz, DMSO-$d_6$) δ 12.88 (brs, 2H), 8.00 (brs, 2H), 7.69 (d, J=1.2 Hz, 2H), 7.58 (d, J=1.4 Hz, 2H), 7.41 (brs, 2H), 6.52 (s, 2H), 5.49 (s, 2H), 5.02-4.76 (m, 4H), 4.59 (dd, J=10.4, 4.2 Hz, 2H), 4.53 (q, J=7.1 Hz, 4H), 4.35-4.25 (m, 2H), 4.19 (dd, J=10.4, 6.4 Hz, 2H), 3.08 (s, 2H), 2.92-2.83 (m, 2H), 2.76-2.65 (m, 2H), 2.08-2.02 (m, 7H), 1.82-1.70 (m, 2H), 1.27 (t, J=7.1 Hz, 6H).

Example 2: (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 2)

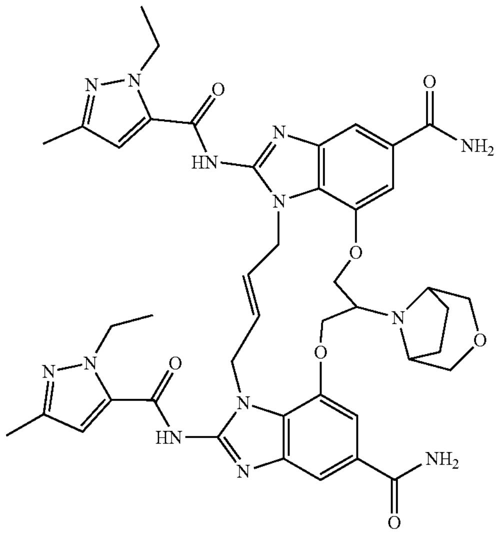 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1C2CCC1COC2)CO3]

Step 1: Synthesis of diethyl 5,5'-((2-(methoxymethoxy)propane-1,3-diyl)bis(oxy))bis(4-chloro-3-nitrobenzoate)

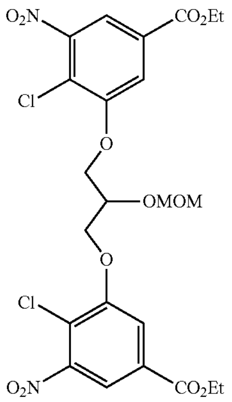

To a cooled solution of ethyl 4-chloro-3-hydroxy-5-nitrobenzoate (32.5 g, 132.3 mmol), 2-(methoxymethoxy)propane-1,3-diol (9.0 g, 66.2 mmol), triphenylphosphine (69.4 g, 264.6 mmol)) in THF (200 ml) was added DIAD (51.5 ml, 264.6 mmol) in dropwise manner at room temperature and reaction mixture was stirred at 60° C. for 16 h. The progress of the reaction was monitored by TLC. Reaction mixture was concentrated to get crude material, to this IPA (200 ml) was added and stirred for 30 min at room temperature and then at −78° C. for 30 min, filtered solid, dried well to afford the title compound, (23.0 g 59% yield).

$^1$H NMR (400 MHz, Chloroform-d) δ 8.08 (d, J=1.7 Hz, 2H), 7.84 (d, J=1.8 Hz, 2H), 4.91 (s, 2H), 4.58-4.40 (m, 9H), 3.48 (s, 3H), 1.44 (t, J=7.1 Hz, 6H).

Step 2: Synthesis of diethyl 5,5'-((2-hydroxypropane-1,3-diyl)bis(oxy))bis(4-chloro-3-nitrobenzoate)

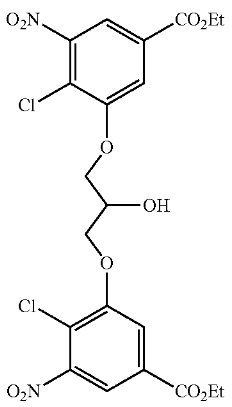 [SMILES: CCOC(=O)c1cc(OCC(O)COc2cc(C(=O)OCC)cc([N+](=O)[O-])c2Cl)c(Cl)c([N+](=O)[O-])c1]

To a cooled solution of diethyl 5,5'-((2-(methoxymethoxy)propane-1,3-diyl)bis(oxy))bis(4-chloro-3-nitrobenzoate) (Step 1, 23.0 g, 38.9 mmol) in DCM (150 ml) and Ethanol (150 ml) was added HCl in dioxane (100 ml, 388.9 mmol), and reaction mixture was stirred at 25° C. for 12 h. The progress of the reaction was monitored by TLC. Reaction mixture was concentrated and dissolved in DCM (50 ml) and washed by 8% sodium bicarbonate solution and by water, organic phase was dried over sodium sulphate and distilled under reduced pressure to get the title compound, (21.0 g, 97% yield).

$^1$H NMR (400 MHz, Chloroform-d) δ 8.10 (d, J=1.7 Hz, 2H), 7.85 (d, J=1.8 Hz, 2H), 4.61 (p, J=5.1 Hz, 1H), 4.50-4.40 (m, 6H), 3.72 (s, 3H), 1.44 (t, J=7.1 Hz, 6H).

Step 3: Synthesis of diethyl 5,5'-((2-(((trifluoromethyl)sulfonyl)oxy)propane-1,3-diyl)bis(oxy))bis(4-chloro-3-nitrobenzoate)

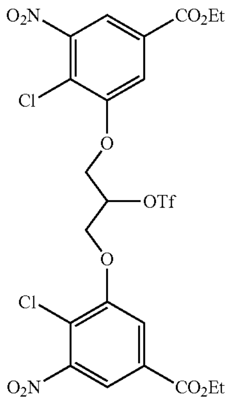 [SMILES: CCOC(=O)c1cc(OCC(COc2cc(C(=O)OCC)cc([N+](=O)[O-])c2Cl)OS(=O)(=O)C(F)(F)F)c(Cl)c([N+](=O)[O-])c1]

To a cooled solution of diethyl 5,5'-((2-hydroxypropane-1,3-diyl)bis(oxy))bis(4-chloro-3-nitrobenzoate) (Step 2, 21.0 g, 38.4 mmol), in DCM (200 ml) 2,6-lutidine (17.9 ml, 153.5 mmol), trifluoromethanesulfonic anhydride (16.2 g, 57.6 mmol)) was added dropwise and reaction mixture was stirred at 0° C. for 1 h. The progress of the reaction was monitored by TLC.

Reaction mixture was quenched with 2N aqueous HCl and extracted by DCM and washed by water, dried over sodium sulphate and concentrated under reduced pressure to get the title compound, (24.0 g, 92% yield).

$^1$H NMR (400 MHz, Chloroform-d) δ 8.15 (d, J=1.7 Hz, 2H), 7.83 (d, J=1.7 Hz, 2H), 5.64 (p, J=4.8 Hz, 1H), 4.70-4.66 (m, 3H), 4.47 (q, J=7.1 Hz, 4H), 3.73 (s, 1H), 1.45 (t, J=7.1 Hz, 6H).

Step 4: Synthesis of diethyl 5,5'-((2-((1R,5S)-3-oxa-8-azabicyclo[3.2.1]octan-8-yl)propane-1,3-diyl)bis(oxy))bis(4-chloro-3-nitrobenzoate)

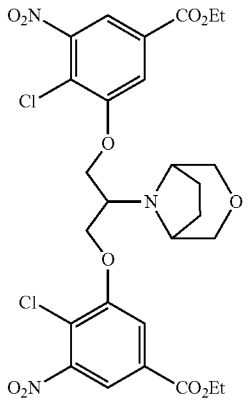 [SMILES: CCOC(=O)c1cc(OCC(COc2cc(C(=O)OCC)cc([N+](=O)[O-])c2Cl)N2C3CCC2COC3)c(Cl)c([N+](=O)[O-])c1]

To a cooled solution of (1R,5S)-3-oxa-8-azabicyclo[3.2.1]octane hydrochloride (10.1 g, 67.7 mmol) in THF (30 ml) was added, TEA (18.9 ml, 135.4 mmol) and stirred for 30 min at 0° C. and then added diethyl 5,5'-((2-(((trifluoromethyl)sulfonyl)oxy)propane-1,3-diyl)bis(oxy))bis(4-chloro-3-nitrobenzoate) (Step 3, 23.0 g, 33.9 mmol), stirred at 25° C. for 12 h. The progress of the reaction was monitored by TLC. Reaction mixture was concentrated and purified by column chromatography to get the title compound, (18.0 g, 83% yield).

LCMS (ESI): m/z 641.47 [M+1]

$^1$H NMR (400 MHz, Chloroform-d) δ 8.07 (d, J=1.7 Hz, 2H), 7.94-7.78 (m, 2H), 4.52-4.29 (m, 8H), 3.77 (d, J=10.5 Hz, 2H), 3.60 (d, J=10.1 Hz, 2H), 3.50-3.33 (m, 2H), 3.33-3.21 (m, 1H), 2.11-1.93 (m, 4H), 1.44 (t, J=7.1 Hz, 6H).

Step 5: Synthesis of diethyl (E)-7-(3-oxa-8-azabicyclo[3.2.1]octan-8-yl)-1,13-dinitro-7,8,14,15,18,19-hexahydro-6H-dibenzo[b,j][1,12]dioxa[4,9]diazacyclopentadecine-3,11-dicarboxylate

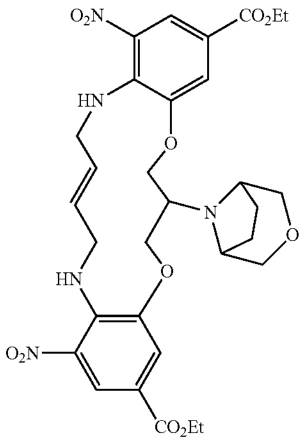 [SMILES: CCOC(=O)c1cc2c(c([N+](=O)[O-])c1)NC/C=C/CNc1c(cc(C(=O)OCC)cc1[N+](=O)[O-])OCC(N1C3CCC1COC3)CO2]

To a solution of diethyl 5,5'-((2-(3-oxa-8-azabicyclo[3.2.1]octan-8-yl)propane-1,3-diyl)bis(oxy))bis(4-chloro-3-nitrobenzoate) (Step 4, 17.9 g, 27.9 mmol) in ethanol (300 ml) in 1 lit autoclave was added (E)-but-2-ene-1,4-diamine dihydrochloride (5.7 g, 36.2 mmol) and DIPEA (38.9 ml, 22.29 mmol) and stirred the reaction mixture at 110° C. for 24 h. The progress of the reaction was monitored by TLC. Reaction mixture was cooled to room temperature and the solid obtained was filtered and dried to get the title compound, (15.5 g, 85% yield).

LCMS (ESI): m/z 656.22 [M+1]

$^1$H NMR (400 MHz, Chloroform-d) δ 8.57 (d, J=1.9 Hz, 2H), 8.46 (m, 2H), 7.64 (d, J=1.9 Hz, 2H), 5.76 (s, 2H), 4.47 (dd, J=16.4, 6.8 Hz, 2H), 4.39 (q, J=7.1 Hz, 4H), 4.26 (dd, J=9.7, 5.1 Hz, 2H), 4.06 (dd, J=16.0, 7.0 Hz, 2H), 3.88-3.78 (m, 4H), 3.63 (d, J=10.5 Hz, 2H), 3.46-3.40 (m, 2H), 3.16 (t, J=5.3 Hz, 1H), 2.04 (s, 4H), 1.41 (t, J=7.1 Hz, 6H).

Step 6: Synthesis of diethyl (E)-1,13-diamino-7-(3-oxa-8-azabicyclo[3.2.1]octan-8-yl)-7,8,14,15,18,19-hexahydro-6H-dibenzo[b,j][1,12]dioxa[4,9]diazacyclopentadecine-3,11-dicarboxylate

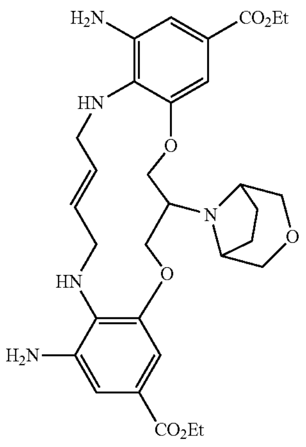

To a stirred suspension of diethyl (E)-7-(3-oxa-8-azabicyclo[3.2.1]octan-8-yl)-1,13-dinitro-7,8,14,15,18,19-hexahydro-6H-dibenzo[b,j][1,12]dioxa[4,9]diazacyclopentadecine-3,11-dicarboxylate (Step 5, 15.0 g, 22.9 mmol) in THF (30 ml) and ethanol (30 ml) was added Sodium dithionite (39.8 g, 228.8 mmol) (solution in 5.0 ml of water) at 0° C. Ammonium hydroxide (71.3 ml, 457.6 mmol) was added at same temperature. Reaction mixture was warmed to 0-25° C. and stirred at 25° C. for 3 h. Progress of reaction was monitored by LCMS. Solid was filtered off and organic solvents were removed under vacuum. Water was added to the reaction mixture and extracted with DCM (4×50 ml). The organic layer was dried over sodium sulphate and concentrated to get crude residue. Solid was washed with ether to get the title compound, (13.0 g, 95% yield).

LCMS (ESI): m/z 596.08 [M+1]

Step 7: Synthesis of diethyl (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxylate

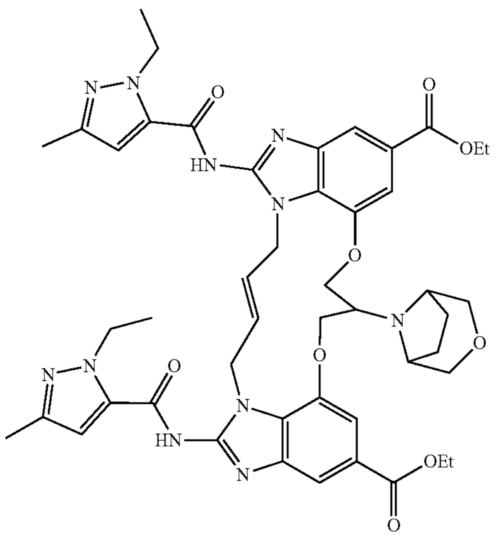 [SMILES: CCOC(=O)c1cc2c3c(c1)nc(NC(=O)c1cc(C)nn1CC)n3C/C=C/Cn1c(NC(=O)c3cc(C)nn3CC)nc3cc(C(=O)OCC)cc(c31)OCC(N1C3CCC1COC3)CO2]

To a stirred solution of diethyl (E)-1,13-diamino-7-(3-oxa-8-azabicyclo[3.2.1]octan-8-yl)-7,8,14,15,18,19-hexahydro-6H-dibenzo[b,j][1,12]dioxa[4,9]diazacyclopentadecine-3,11-dicarboxylate (Step 6, 14.0 g, 23.5 mmol) in DMF (200 ml), 1-ethyl-3-methyl-1H-pyrazole-5-carbonyl isothiocyanate (8.3 g, 42.3 mmol) in 1 ml of DMF was added at 0° C. and stirred for 30 min followed by addition of EDC (18.0 g, 94.0 mmol) and TEA (26.2 ml, 188.0 mmol) were added at 0° C. and stirred for 18 hr. Reaction was monitored by LCMS. After completion, the mixture was concentrated under reduced pressure, water was added solid was filtered and dried to get crude material, which was purified by column chromatography (5% MeOH/DCM) to get the title compound, (14.0 g, 65% yield).

LCMS (ESI): m/z 918.07 [M+1]

$^1$H NMR (400 MHz, DMSO-$d_6$) δ 12.91 (s, 2H), 7.83 (d, J=1.3 Hz, 2H), 7.61 (d, J=1.4 Hz, 2H), 6.50 (s, 2H), 5.39 (s, 2H), 4.95 (d, J=16.0 Hz, 2H), 4.81 (d, J=16.4 Hz, 2H), 4.58 (dd, J=10.7, 4.4 Hz, 2H), 4.55-4.46 (m, 4H), 4.38-4.28 (m, 4H), 3.99-3.90 (m, 2H), 3.69 (d, J=10.1 Hz, 2H), 3.58 (d,

J=4.2 Hz, 2H), 3.51 (d, J=10.2 Hz, 2H), 2.93 (t, J=5.1 Hz, 1H), 2.04 (s, 6H), 1.99-1.90 (m, 2H), 1.87-1.77 (m, 2H), 1.33 (t, J=7.1 Hz, 6H), 1.25 (t, J=7.1 Hz, 6H).

Step 8: Synthesis of (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxylic acid

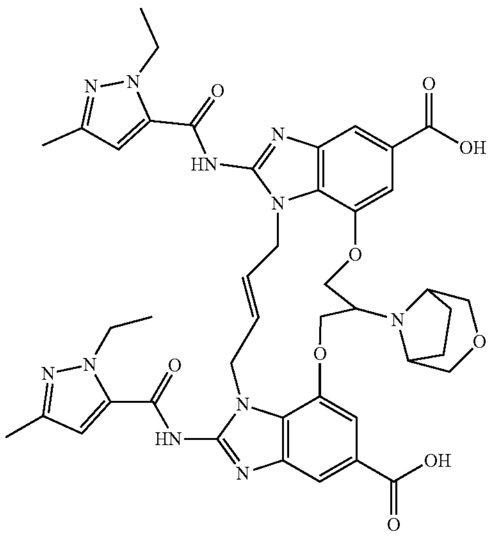 [SMILES: CCn1nc(C)cc1C(=O)Nc1nc2cc(C(=O)O)cc3c2n1C/C=C/Cn1c(NC(=O)c2cc(C)nn2CC)nc2cc(C(=O)O)cc(c21)OCC(N1C2CCC1COC2)CO3]

To the stirred solution of diethyl (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd'] diindene-4,12-dicarboxylate (Step 7, 14.0 g, 15.3 mmol) in ethanol (70 ml) and THF (70 ml) was added lithium hydroxide hydrate (6.4 g, 152.5 mmol) by dissolving it in water (10 ml) at room temperature and stirred for 16 h at 50° C. The reaction was monitored by LCMS, after completion it was concentrated under reduced pressure, water was added and pH was adjusted to acidic by using 1N HCl. Solid was precipitate out, which was filtered and dried to get the title compound, (12.0 g, 91% yield).

LCMS (ESI): m/z 862.05 [M+1]

$^1$H NMR (400 MHz, DMSO-$d_6$) δ 7.94-7.81 (m, 2H), 7.70 (s, 2H), 5.55 (s, 2H), 5.20-4.97 (m, 4H), 4.86 (t, J=16.4 Hz, 2H), 4.64-4.39 (m, 8H), 3.81-3.63 (m, 5H), 2.41-2.32 (m, 2H), 2.15 (d, J=8.4 Hz, 2H), 2.06 (s, 6H), 1.26 (t, J=7.1 Hz, 6H).

Step 9: Synthesis of (E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 2)

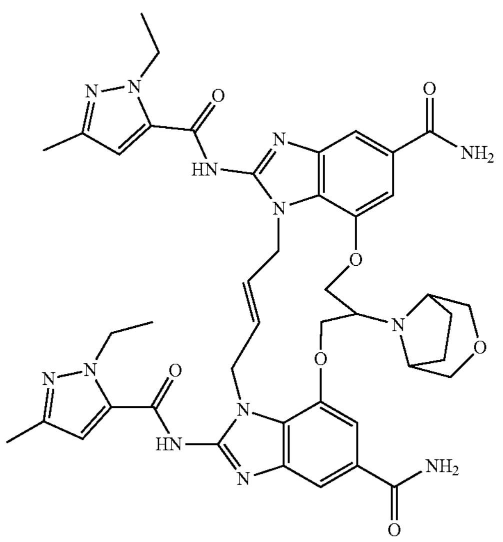 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1C2CCC1COC2)CO3]

(E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxylic acid (Step 8, 10.0 g, 11.6 mmol) was dissolved in DMSO (80 ml). To this stirred solution were added HOBT (8.9 g, 58.0 mmol), EDC (11.1 g, 58.0 mmol) and DIPEA (16.2 ml, 92.8 mmol) in dropwise manner followed by addition of ammonium chloride (21.7 g, 406.1 mmol) at 0° C. Reaction mixture was allowed to stir at room temperature for overnight. The reaction was monitored by LCMS. After completion, the reaction mixture was poured into cold water, solid was precipitated out which was filtered & washed with water. Solid was dried well to get crude material. Crude product was purified by column chromatography, (DCM: MeOH) 20% and obtained solid was washed with acetonitrile and filtered to get the title compound, (6.0 g 60% yield).

LCMS (ESI): m/z 860.68 $(M+H)^+$ $^1$H NMR (400 MHz, DMSO-$d_6$) δ 12.88 (s, 2H), 8.01 (s, 2H), 7.73 (s, 2H), 7.63 (s, 2H), 7.38 (s, 2H), 6.50 (s, 2H), 5.40 (s, 2H), 4.98 (d, J=16.4 Hz, 2H), 4.79 (d, J=16.5 Hz, 2H), 4.60 (dd, J=10.7, 4.6 Hz, 2H), 4.50 (q, J=7.2 Hz, 4H), 3.97 (dd, J=10.8, 5.5 Hz, 2H), 3.68 (d, J=10.1 Hz, 2H), 3.60 (s, 2H), 3.53 (d, J=10.0 Hz, 2H), 2.96-2.84 (m, 1H), 2.04 (s, 6H), 1.95 (s, 2H), 1.84-1.74 (m, 2H), 1.28-1.21 (m, 6H).

Example 3: (E)-1,15-bis(1-ethyl-3-methyl-1H-pyrazole-5-carboxamido)-8-morpholino-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 3)

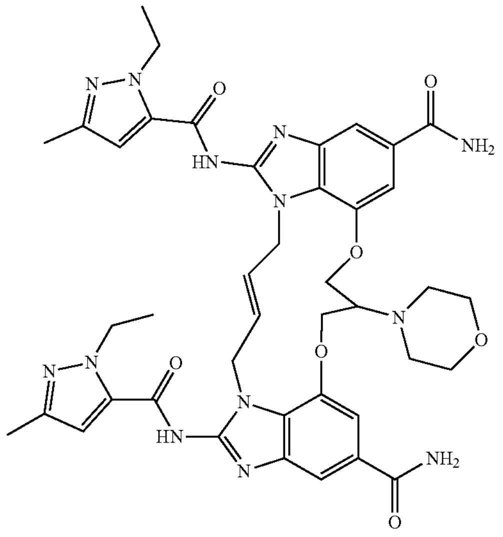 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCOCC1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 4-(1,3-dichloropropan-2-yl)morpholine and converting the product to the corresponding hydrochloride salt.

LCMS (ESI): m/z 834.67 $(M+H)^+$ $^1$H NMR (400 MHz, DMSO-$d_6$) δ 12.24 (brs, 2H), 8.12 (brs, 2H), 7.95 (s, 2H), 7.81 (d, J=1.2 Hz, 2H), 7.51 (brs, 2H), 6.52 (s, 2H), 5.29 (s, 2H), 5.16 (d, J=9.0 Hz, 2H), 5.00-4.77 (m, 4H), 4.49 (q, J=7.1 Hz, 4H), 4.40 (dd, J=11.8, 6.0 Hz, 2H), 4.14-4.02 (m, 5H), 3.73-3.50 (m, 4H), 2.03 (s, 6H), 1.24 (t, J=7.1 Hz, 6H).

Example 4: (E)-8-(4,4-difluoropiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 4)

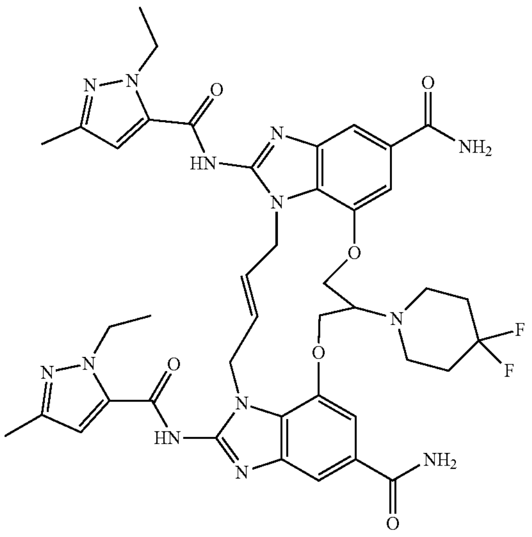 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(F)(F)CC1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 1-(1,3-dichloropropan-2-yl)-4,4-difluoropiperidine.

LCMS (ESI): m/z 868.67 $(M+H)^+$ $^1$H NMR (400 MHz, DMSO-$d_6$) δ 12.86 (s, 2H), 8.32 (s, 1H), 8.01 (s, 2H), 7.67 (d, J=2.7 Hz, 4H), 7.43 (s, 2H), 6.55 (s, 2H), 5.58 (s, 2H), 4.90 (s, 4H), 4.66-4.46 (m, 7H), 4.26 (dd, J=10.6, 6.5 Hz, 2H), 2.94 (d, J=5.5 Hz, 4H), 2.08 (m, 10H), 1.27 (m, 6H).

Example 5: (E)-8-((2S,6R)-2,6-dimethylmorpholino)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 5)

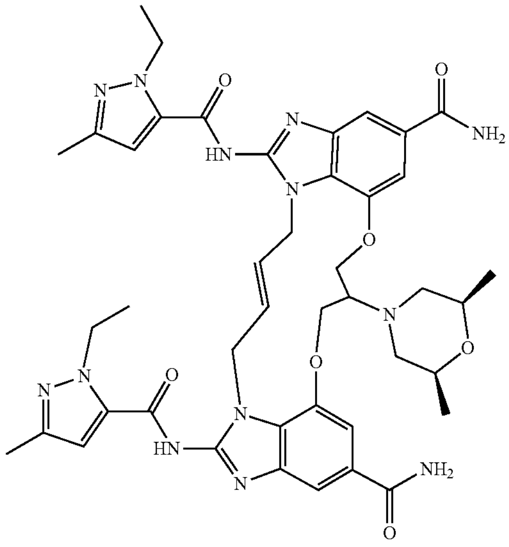

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and (2S,6R)-4-(1,3-dichloropropan-2-yl)-2,6-dimethylmorpholine and converting the product to the corresponding hydrochloride salt.

LCMS (ESI): m/z 862.80 $(M+H)^+$ $^1$H NMR (400 MHz, DMSO-$d_6$) δ 8.14 (s, 2H), 7.97 (s, 2H), 7.80 (d, J=1.1 Hz, 2H), 7.49 (s, 2H), 6.52 (s, 2H), 4.92 (s, 3H), 4.50 (t, J=7.0 Hz, 4H), 4.39-4.28 (m, 4H), 3.80-3.68 (m, 4H), 3.38 (qd, J=7.1, 5.5 Hz, 6H), 3.17 (s, 3H), 2.03 (s, 6H), 1.22 (t, J=7.0 Hz, 6H), 1.09 (d, J=7.0 Hz, 6H).

Example 6: (S,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 6)

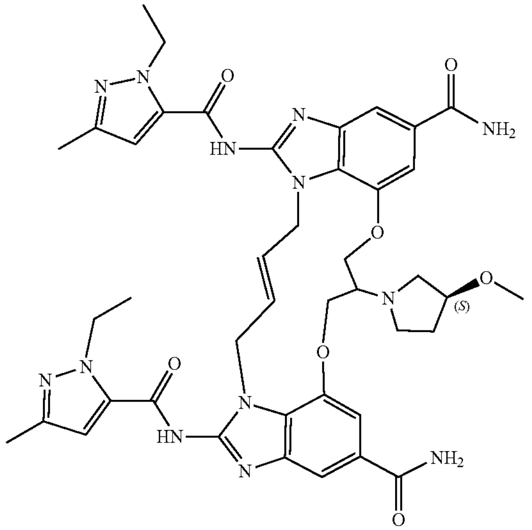

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and (S)-1-(1,3-dichloropropan-2-yl)-3-methoxypyrrolidine.

LCMS (ESI): m/z 848.18 $(M+H)^+$ $^1$H NMR (400 MHz, DMSO-$d_6$) δ 12.86 (s, 2H), 8.02 (s, 2H), 7.73 (s, 2H), 7.64 (s, 2H), 7.39 (s, 2H), 6.52 (s, 2H), 5.44 (s, 2H), 4.98-4.79 (m, 4H), 4.64 (d, J=10.6 Hz, 3H), 4.51 (d, J=7.8 Hz, 4H), 4.13 (s, 2H), 3.95 (s, 1H), 3.23 (s, 3H), 3.07 (d, J=11.4 Hz, 2H), 2.85 (m, 2H), 2.05 (s, 6H), 1.76 (s, 2H), 1.28 (t, J=7.1 Hz, 6H).

Example 7: (E)-1,15-bis(1-ethyl-3-methyl-1H-pyrazole-5-carboxamido)-8-(piperidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 7)

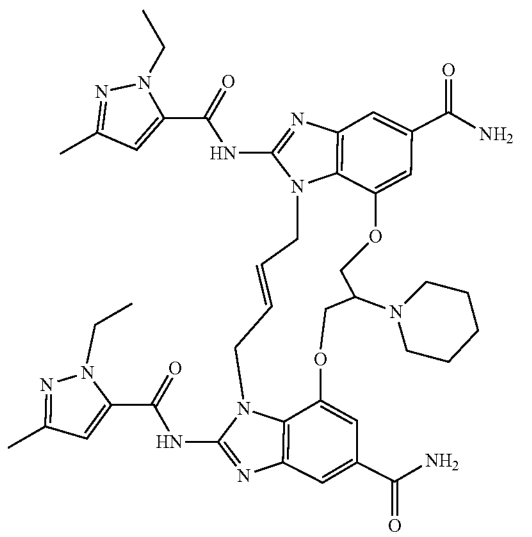 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCCCC1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 1-(1,3-dichloropropan-2-yl)piperidine.

LCMS (ESI): m/z 832.52 $(M+H)^+$ $^1H$ NMR (400 MHz, DMSO-$d_6$) δ 12.89 (s, 2H), 8.00 (s, 2H), 7.70 (s, 2H), 7.62 (d, J=5.2 Hz, 2H), 7.39 (s, 2H), 6.54 (s, 2H), 5.54 (s, 2H), 4.90 (m, 4H), 4.62 (dd, J=10.5, 4.3 Hz, 2H), 4.53 (q, J=7.4 Hz, 3H), 4.20 (dd, J=10.5, 6.4 Hz, 2H), 2.78 (t, J=5.2 Hz, 4H), 2.07 (s, 6H), 1.60 (s, 4H), 1.47 (s, 2H), 1.27 (t, J=6.8 Hz, 6H).

Example 8: (E)-8-(azetidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 8)

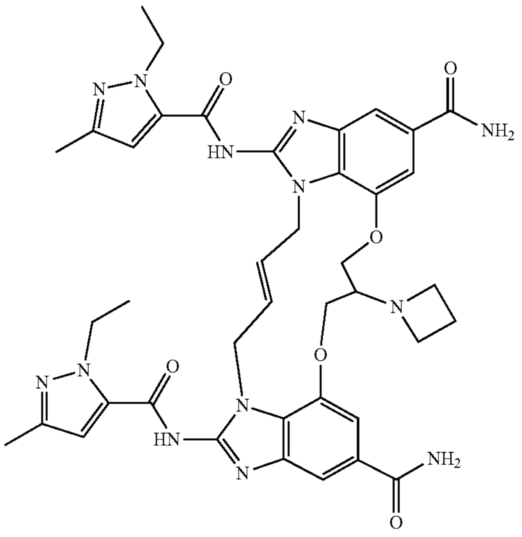 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 1-(1,3-dichloropropan-2-yl)azetidine hydrochloride.

LCMS (ESI): m/z 804.67 $(M+H)^+$ $^1H$ NMR (400 MHz, DMSO-$d_6$) δ 12.86 (brs, 2H), 7.98 (d, J=1.6 Hz, 2H), 7.66 (d, J=1.8 Hz, 2H), 7.35 (m, 4H), 6.45 (m, 2H), 6.12 (m, 2H), 5.12 (m, 1H), 5.05-4.88 (m, 3H), 4.65-4.34 (m, 6H), 4.28 (t, J=7.8 Hz, 1H), 3.65 (t, J=9.9 Hz, 1H), 2.08 (m, 2H), 1.89 (d, J=8.0 Hz, 6H), 1.80-1.69 (m, 1H), 1.55 (d, J=6.7 Hz, 1H), 1.34-1.18 (m, 6H).

Example 9: (E)-1,15-bis(1-ethyl-3-methyl-1H-pyrazole-5-carboxamido)-8-(1-methylpiperidin-4-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 9)

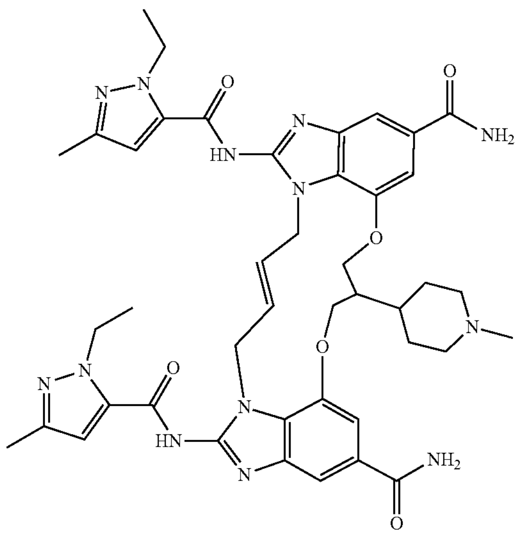

The title compound as its formate salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 4-(1,3-dichloropropan-2-yl)-1-methylpiperidine.

LCMS (ESI): m/z 846.68 $(M+H)^+$ $^1$H NMR (400 MHz, DMSO-$d_6$) δ 12.95 (s, 3H), 8.48 (s, 1H), 8.60-8.42 (m, 2H), 8.02-7.95 (m, 1H), 7.81 (s, 1H), 7.66 (s, 1H), 7.40 (d, J=7.4 Hz, 3H), 7.33 (s, 1H), 7.25 (s, 1H), 6.56 (s, 1H), 6.44 (s, 1H), 5.82 (m, 2H), 4.92 (m, 4H), 4.52 (m, 4H), 4.05 (d, J=7.6 Hz, 2H), 2.89 (s, 4H), 2.55-2.54 (s, 3H), 2.10 (d, J=21.4 Hz, 6H), 2.00 (s, 2H), 1.84 (d, J=7.5 Hz, 1H), 1.59 (s, 1H), 1.38-1.15 (m, 8H).

Example 10: (E)-1,15-bis(1-ethyl-3-methyl-1H-pyrazole-5-carboxamido)-8-(piperazin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 10)

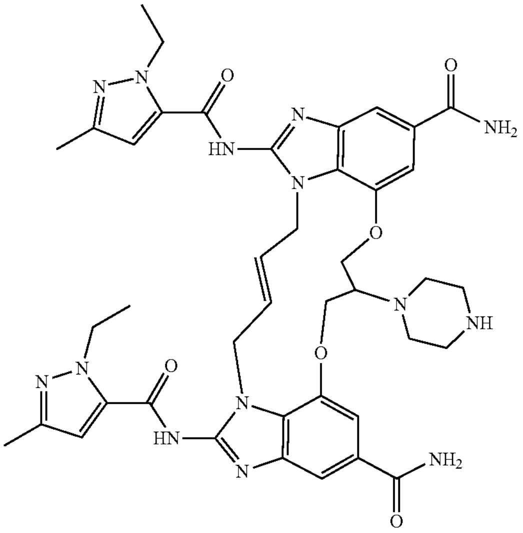 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCNCC1)CO3]

The title compound as its dihydrochloride salt was prepared by following the procedure outlined for Example 1 using (E)-1,1'-(but-2-ene-1,4-diyl)bis(2-(I-ethyl-3-methyl-1H-pyrazole-5-carboxamido)-7-hydroxy-1H-benzo[d]imidazole-5-carboxamide) and tert-butyl 4-(1,3-dichloropropan-2-yl)piperazine-1-carboxylate followed by Boc deprotection.

LCMS (ESI): m/z 833.80 $(M+H)^+$ $^1$H NMR (400 MHz, DMSO-$d_6$) δ 8.07 (s, 2H), 7.79 (d, J=18.4 Hz, 4H), 7.45 (s, 2H), 6.53 (s, 2H), 5.43 (s, 1H), 4.91 (s, 6H), 4.51 (d, J=7.4 Hz, 5H), 3.46-3.30 (m, 9H), 2.04 (s, 6H), 1.27 (d, J=7.0 Hz, 6H).

Example 11: (S,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 11)

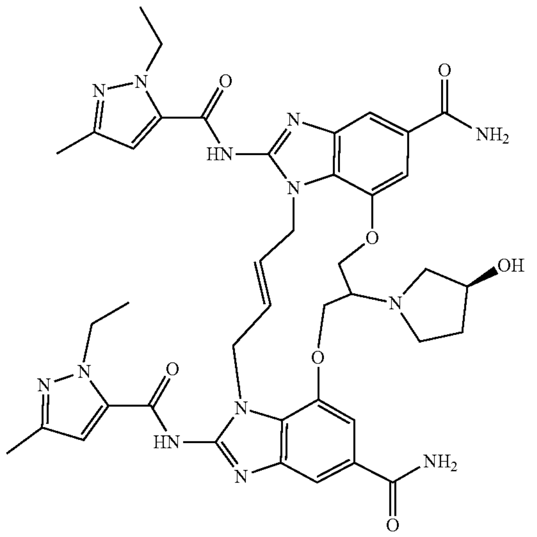 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@H](O)C1)CO3]

Step-1: Synthesis of diethyl (S)-2-(3-((tert-butyldimethylsilyl)oxy)pyrrolidin-1-yl)malonate

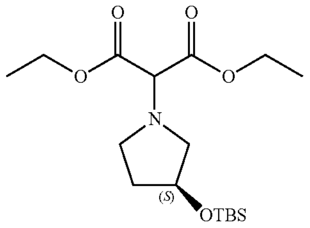

Diethyl (S)-2-(3-((tert-butyldimethylsilyl)oxy)pyrrolidin-1-yl)malonate synthesized from diethyl 2-bromomalonate and (S)-3-((tert-butyldimethylsilyl)oxy)pyrrolidine hydrochloride by using the procedure disclosed in Step-1 of Intermediate 2.

LCMS (ESI): m/z 360.41 $(M+H)^+$ $^1$H NMR (400 MHz, $CDCl_3$) δ 4.49-4.38 (m, 1H), 4.26 (q, J=7.0 Hz, 4H), 3.26 (dd, J=9.4, 6.3 Hz, 1H), 3.03-2.82 (m, 2H), 2.63 (dd, J=9.4, 4.8 Hz, 1H), 2.19-2.01 (m, 1H), 1.81-1.65 (m, 2H), 1.31 (t, 6H), 0.89 (s, 9H), 0.06 (s, 6H).

Step-2: Synthesis of (S)-2-(3-((tert-butyldimethylsilyl)oxy)pyrrolidin-1-yl)propane-1,3-diol

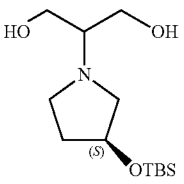

(S)-2-(3-((tert-butyldimethylsilyl)oxy)pyrrolidin-1-yl)propane-1,3-diol synthesized from diethyl (S)-2-(3-((tert-butyldimethylsilyl)oxy)pyrrolidin-1-yl)malonate (Step 1 product) by using the procedure disclosed in Step-2 of Intermediate 2.

LCMS (ESI): m/z 276.21 $(M+H)^+$ $^1$H NMR (400 MHz, $CDCl_3$) δ 4.42 (m, 1H), 3.94-3.82 (m, 1H), 3.81-3.73 (m, 4H), 3.19 (dd, J=10.6, 5.3 Hz, 1H), 3.01-2.95 (m, 1H), 2.85-2.73 (m, 2H), 2.14-2.01 (m, 1H), 1.91-1.74 (m, 1H), 0.91 (s, 9H), 0.10 (s, 6H).

Step 3: Synthesis of dimethyl 5,5'-((2-(3-((tert-butyldimethylsilyl)oxy)pyrrolidin-1-yl)propane-1,3-diyl)bis(oxy))(S)-bis(4-chloro-3-nitrobenzoate)

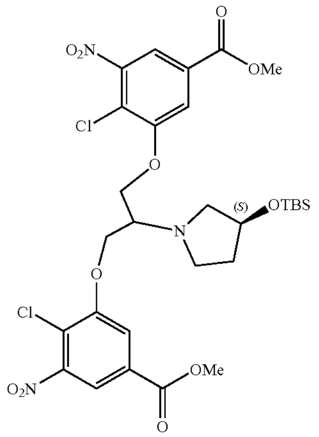

To the stirred solution of methyl 4-chloro-3-hydroxy-5-nitrobenzoate (Synthesized by methods reported in the literature, 3.87 g, 16.70 mmol), (S)-2-(3-((tert-butyldimethylsilyl)oxy)pyrrolidin-1-yl)propane-1,3-diol (Step-2 product, 2.3 g, 8.35 mmol) and triphenylphosphine (8.76 g, 33.4 mmol) in THF (10 ml) was added DIAD (6.49 ml, 33.4 mmol) in dropwise manner at 0-5° C. After the addition reaction mixture was stirred at 50° C. for 8 hr. After the completion of reaction as it was monitored by TLC, the volatiles were concentrated under reduced pressure and the crude purified by column chromatography to afford the title product as an off-white solid (2.3 g, 40%).

LCMS (ESI): m/z 702.58 $(M+H)^+$ $^1$H NMR (400 MHz, $CDCl_3$) δ 8.13-8.03 (m, 2H), 7.89-7.76 (m, 2H), 4.48 (m, 5H), 3.99 (s, 6H), 3.67-3.43 (m, 1H), 3.16 (m, 3H), 2.79 (s, 1H), 2.21-1.89 (m, 2H), 0.89 (s, 9H), 0.08 (s, 6H).

Step 4: Synthesis of dimethyl (S,E)-7-(3-((tert-butyldimethylsilyl)oxy)pyrrolidin-1-yl)-1,13-dinitro-7,8,14,15,18,19-hexahydro-6H-dibenzo[b,j][1,12]dioxa[4,9]diazacyclopentadecine-3,11-dicarboxylate

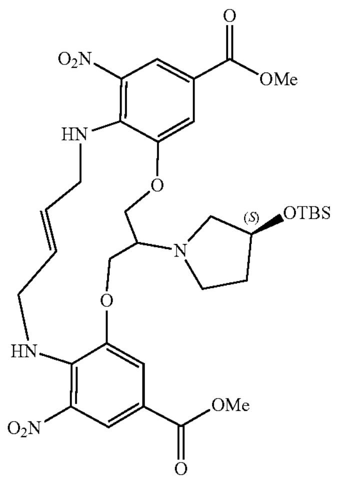

To the stirred solution of dimethyl 5,5'-((2-(3-((tert-butyldimethylsilyl)oxy)pyrrolidin-1-yl)propane-1,3-diyl)bis(oxy))(S)-bis(4-chloro-3-nitrobenzoate) (Step 3, 1.2 g, 1.71 mmol) in 30 ml ethanol were added (E)-but-2-ene-1,4-diamine dihydrochloride (0.27 g, 1.71 mmol) and DIPEA (1.79 ml, 10.25 mmol). The reaction mixture was stirred at 120° C. for 16 hr in a sealed tube. The progress of the reaction was monitored by LCMS and TLC. After the completion, the reaction mass was concentrated under reduced pressure and the crude purified by column chromatography to afford the title product as a red coloured solid. (0.76 g, 62%).

LCMS (ESI): m/z 716.77 $(M+H)^+$ $^1$H NMR (400 MHz, Chloroform-d) δ 8.56 (d, J=2.1 Hz, 2H), 8.45 (t, J=6.6 Hz, 2H), 7.62 (d, J=2.0 Hz, 2H), 5.79 (d, J=1.5 Hz, 2H), 4.56-4.44 (m, 3H), 4.37 (q, J=7.1 Hz, 3H), 4.11-4.01 (m, 3H), 3.91 (s, 6H), 3.89-3.85 (m, 2H), 1.81-1.75 (m, 2H), 1.45-1.38 (m, 3H), 0.92 (s, 9H), 0.11 (d, J=1.3 Hz, 6H).

Step 5: Synthesis of dimethyl (S,E)-1,13-diamino-7-(3-((tert-butyldimethylsilyl)oxy)pyrrolidin-1-yl)-7,8,14,15,18,19-hexahydro-6H-dibenzo[b,j][1,12]dioxa[4,9]diazacyclopentadecine-3,11-dicarboxylate

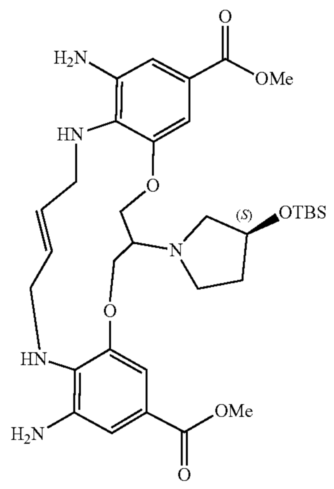

To the solution of dimethyl (S,E)-7-(3-((tert-butyldimethylsilyl)oxy)pyrrolidin-1-yl)-1,13-dinitro-7,8,14,15,18,19-hexahydro-6H-dibenzo[b,j][1,12]dioxa[4,9]diazacyclopentadecine-3,11-dicarboxylate (Step 4, 0.750 g, 1.048 mmol) in methanol:THF (15 ml:15 ml) was added solution of sodium dithionite (2.159 g, 10.48 mmol) in 10 ml water followed by the addition of ammonium hydroxide (4.08 ml, 26.2 mmol) at 0° C. Reaction was monitored by TLC and LCMS. Reaction mass was added to water (20 ml) and was extracted with ethyl acetate and dried over sodium sulphate and concentrated under reduced pressure to get crude which was purified by column chromatography to afford the title product (0.6 g, 87%).

LCMS (ESI): m/z 656.70 $(M+H)^+$

Step 6: Synthesis of Dimethyl (S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd'] diindene-4,12-dicarboxylate

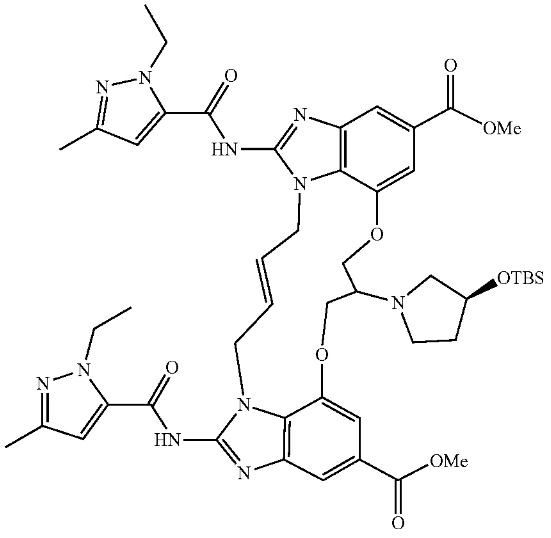 [SMILES: CCn1nc(C)cc1C(=O)Nc1nc2cc(C(=O)OC)cc3c2n1C/C=C/Cn1c(NC(=O)c2cc(C)nn2CC)nc2cc(C(=O)OC)cc(c21)OCC(N1CC[C@H](O[Si](C)(C)C(C)(C)C)C1)CO3]

To a stirred solution of dimethyl (S,E)-1,13-diamino-7-(3-((tert-butyldimethylsilyl)oxy)pyrrolidin-1-yl)-7,8,14,15,18,19-hexahydro-6H-dibenzo[b,j][1,12]dioxa[4,9]diazacyclopentadecine-3,11-dicarboxylate (Step 5, 0.65 g, 0.99 mmol) in 20 ml DMF was added 1-ethyl-3-methyl-1H-pyrazole-5-carbonyl isothiocyanate (0.35 g, 1.78 mmol) at 0° C. The reaction mixture was stirred for 30 min followed by the addition of EDC (0.57 g, 2.97 mmol) and $Et_3N$ (0.69 ml, 4.96 mmol) and the reaction mixture allowed to warm at room temperature for overnight. After the completion of the reaction, the mixture was concentrated under reduced pressure and water was added resulting in the precipitation of the product as a white solid which was filtered and dried. (800 mg, 83%).

LCMS (ESI): m/z 977.58 $(M+H)^+$ $^1$H NMR (400 MHz, DMSO-$d_6$) δ 12.94 (brs, 2H), 7.83 (d, J=5.8 Hz, 2H), 7.62 (d, J=4.9 Hz, 2H), 6.53 (s, 2H), 5.49 (d, J=10.3 Hz, 2H), 4.92 (m, 4H), 4.71-4.47 (m, 6H), 4.43 (s, 2H), 4.33 (q, J=7.0 Hz, 2H), 4.21 (m, 2H), 3.87 (s, 6H), 3.13 (m, 1H), 2.99 (s, 1H), 2.88 (d, J=10.6 Hz, 1H), 2.78-2.65 (m, 2H), 2.05 (s, 6H), 1.66 (s, 1H), 1.26 (t, J=6.9 Hz, 6H), 0.88 (s, 9H), 0.08 (d, J=1.8 Hz, 6H).

Step 7: Synthesis of (S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca [3,2,1-cd:8,9,10-c'd']diindene-4,12-dicarboxylic acid

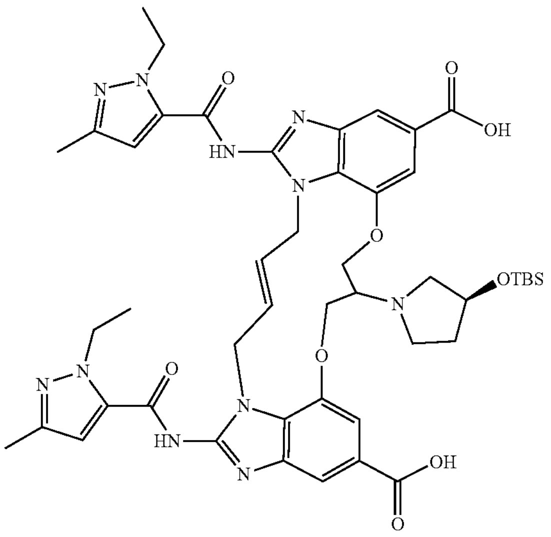 [SMILES: CCn1nc(C)cc1C(=O)Nc1nc2cc(C(=O)O)cc3c2n1C/C=C/Cn1c(NC(=O)c2cc(C)nn2CC)nc2cc(C(=O)O)cc(c21)OCC(N1CC[C@H](O[Si](C)(C)C(C)(C)C)C1)CO3]

To a solution of Dimethyl (S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxylate (Step 6, 800 mg, 0.82 mmol) in 15 ml of a mixture of THF, methanol and water (1:1:1) was added lithium hydroxide (19.58 mg, 0.82 mmol) & stirred for 12 hr at room temperature. Reaction was monitored by LCMS. After the completion of reaction, the mixture was concentrated under reduced pressure to get a residue which was diluted with water. A solution of 1 N HCl was added until the pH 5 and the resulting white precipitate was filtered and dried to afford the title compound (640 mg, 84% yield).

LCMS (ESI): m/z 950.82 $(M+H)^+$ $^1$H NMR (400 MHz, DMSO-$d_6$) δ 12.96 (brs, 4H), 7.86 (d, J=8.2 Hz, 2H), 7.83-7.62 (m, 2H), 6.54 (s, 2H), 5.47 (s, 2H), 5.12-4.76 (m, 8H), 4.51 (d, J=7.6 Hz, 8H), 4.30-3.98 (m, 1H), 2.80-2.63 (m, 2H), 2.17 (d, J=2.6 Hz, 1H), 2.05 (s, 6H), 1.29-1.25 (m, 6H), 0.87 (s, 9H), 0.10 (s, 6H).

Step 8: Synthesis of (S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide

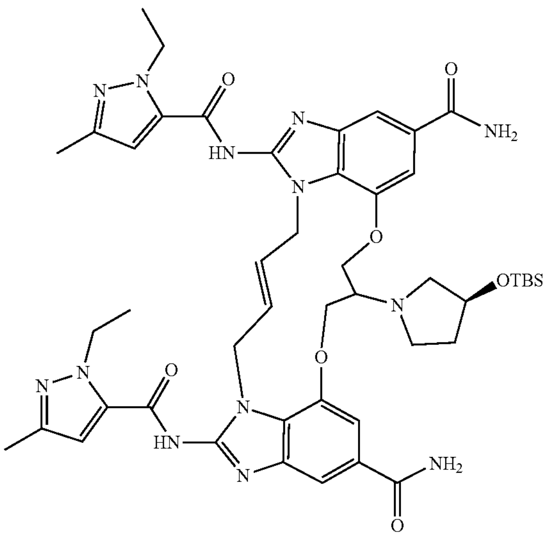 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@H](O[Si](C)(C)C(C)(C)C)C1)CO3]

(S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxylic acid (Step 7, 650 mg, 0.684 mmol) was dissolved in 50 ml DMF. Ammonium chloride (1.1 g, 20.52 mmol), TBTU (661 mg, 2.052 mmol) followed by DIPEA (0.717 ml, 4.10 mmol) was added and the reaction mixture was allowed to stir at room temperature overnight. The reaction was monitored by LCMS, and after the completion of reaction, the mixture was concentrated and poured into crushed ice. The diamide as a white solid was obtained which was filtered and dried (600 mg, 92% yield).

LCMS (ESI): m/z 949.07 $(M+H)^+$ $^1$H NMR (400 MHz, DMSO-$d_6$) δ 12.95 (brs, 2H), 7.78 (brs, 2H), 7.32 (brs, 2H), 7.19 (s, 2H), 7.06 (s, 2H), 6.52 (s, 2H), 5.34 (d, J=16.4 Hz, 2H), 5.11-4.76 (m, 8H), 4.50 (d, J=7.2 Hz, 6H), 3.71-3.50 (m, 2H), 3.13 (dd, J=7.3, 4.2 Hz, 2H), 2.16 (s, 2H), 2.04 (s, 6H), 1.30-1.20 (m, 6H), 0.87 (s, 9H), 0.10 (s, 6H).

Step 9: Synthesis of (S,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide hydrochloride salt (Compound 11)

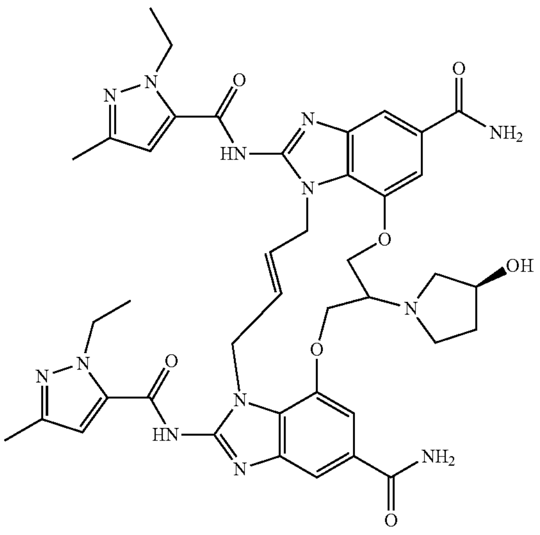 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@H](O)C1)CO3]

(S,E)-8-(3-((tert-butyldimethylsilyl)oxy)pyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Step 8, 600 mg, 0.633 mmol) was stirred in 3 M HCl in methanol for 16 hrs at room temperature. The progress of the reaction was monitored by LCMS. After completion of the reaction, the volatiles were removed under reduced pressure to get the crude, which was triturated with ether to obtain the title compound which was further purified by preparative HPLC. (150 mg, 28% yield).

LCMS (ESI): m/z 834.80 $(M+H)^+$ $^1$H NMR (400 MHz, DMSO-$d_6$) δ 8.19-8.00 (m, 2H), 7.89-7.76 (m, 4H), 7.48 (s, 2H), 6.54 (d, J=2.0 Hz, 2H), 5.34 (d, J=3.9 Hz, 2H), 4.94 (m, 6H), 4.50 (m, 10H), 4.06-3.37 (m, 2H), 2.55 (d, J=2.3 Hz, 2H), 2.04 (m, 6H), 1.26-1.23 (m, 6H).

Example 12: (R,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 12)

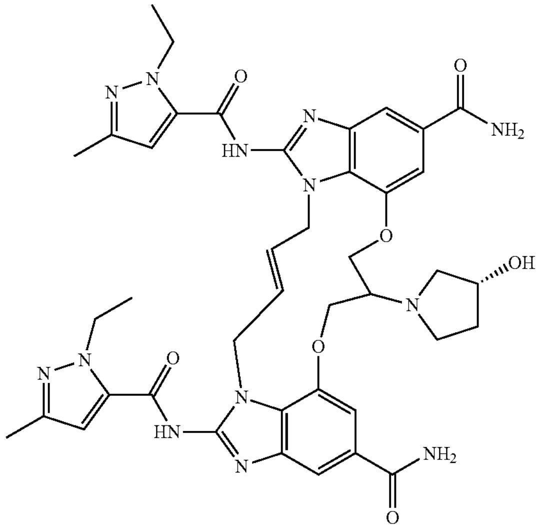 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@@H](O)C1)CO3]

The title compound as its hydrochloride salt was prepared by following the procedure outlined for Example 11 using methyl 4-chloro-3-hydroxy-5-nitrobenzoate and (R)-2-(3-((tert-butyldimethylsilyl)oxy)pyrrolidin-1-yl)propane-1,3-diol LCMS (ESI): m/z 834.80 $(M+H)^+$ $^1$H NMR (400 MHz, DMSO-$d_6$) δ 8.19-8.00 (m, 2H), 7.89-7.76 (m, 4H), 7.48 (s, 2H), 6.54 (d, J=2.0 Hz, 2H), 5.34 (d, J=3.9 Hz, 2H), 4.94 (m, 6H), 4.50 (m, 10H), 4.06-3.37 (m, 2H), 2.55 (d, J=2.3 Hz, 2H), 2.04 (m, 6H), 1.26-1.23 (m, 6H).

Example 13: (E)-1,15-bis(1-ethyl-3-methyl-1H-pyrazole-5-carboxamido)-8-(2-morpholinoethyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 13)

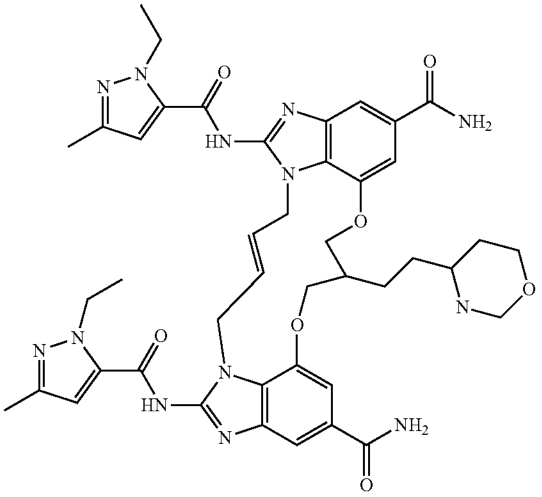 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(CCC1CCOCN1)CO3]

The title compound as its hydrochloride salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 4-(4-chloro-3-(chloromethyl)butyl)morpholine.

LCMS (ESI): m/z 862.51 $(M+H)^+$ $^1$H NMR (400 MHz, DMSO-$d_6$) δ 12.90 (brs, 2H), 10.57 (brs, 1H), 7.98 (brs, 1H), 7.88 (brs, 1H), 7.67 (s, 1H), 7.44 (brs, 1H), 7.38 (s, 1H), 7.33 (s, 1H), 7.29 (brs, 1H), 7.19 (s, 1H), 6.55 (s, 1H), 6.48 (s, 1H), 5.87-5.74 (m, 2H), 5.05-4.80 (m, 4H), 4.63-4.42 (m, 4H), 4.05 (d, J=5.4 Hz, 4H), 3.87-3.31 (m, 6H), 2.68-2.60 (m, 4H), 2.35-2.25 (m, 3H), 2.13 (s, 3H), 2.09 (s, 3H), 1.29 (t, J=7.1 Hz, 6H).

Example 14: (E)-1,15-bis(1-ethyl-3-methyl-1H-pyrazole-5-carboxamido)-8-((1-methylazetidin-3-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 14)

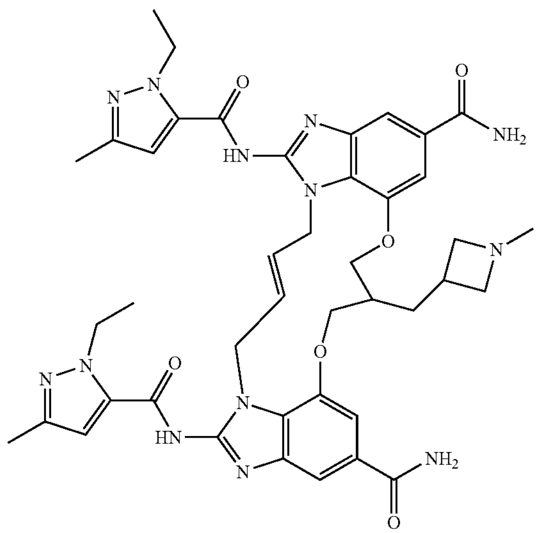

The title compound as its formate salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 3-(1,3-dichloropropan-2-yl)-1-methylazetidine.

LCMS (ESI): m/z 832.52 $(M+H)^+$ $^1$H NMR (400 MHz, DMSO-$d_6$) δ 12.83 (s, 3H), 8.27 (s, 1H), 8.16-7.91 (m, 1H), 7.73 (s, 1H), 7.72-7.63 (m, 1H), 7.61 (s, 1H), 7.49-7.25 (m, 4H), 6.53 (s, 2H), 5.39 (s, 2H), 5.05-4.81 (m, 4H), 4.65-4.44 (m, 4H), 4.35 (m, 2H), 4.14 (dd, J=9.7, 6.7 Hz, 2H), 3.57 (t, J=7.3 Hz, 2H), 2.99 (s, 2H), 2.55 (s, 3H), 2.47-2.39 (m, 2H), 2.25-1.98 (m, 8H), 1.32-1.14 (m, 6H).

Example 15: (E)-1,15-bis(1-ethyl-3-methyl-1H-pyrazole-5-carboxamido)-8-((1-methylpiperidin-4-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 15)

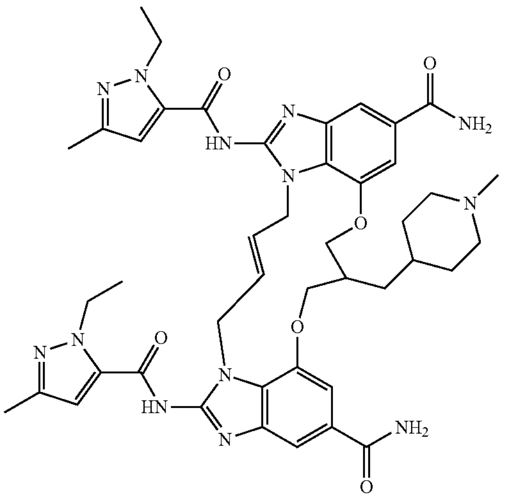

The title compound as its formate salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 4-(3-chloro-2-(chloromethyl)propyl)-1-methylpiperidine.

LCMS (ESI): m/z 860.53 $(M+H)^+$ $^1$H NMR (400 MHz, DMSO-$d_6$) δ 12.92 (brs, 2H), 8.31 (s, 1H), 8.02 (brs, 2H), 7.73 (d, J=1.2 Hz, 2H), 7.59 (s, 2H), 7.40 (brs, 2H), 6.53 (s, 2H), 5.39 (s, 2H), 4.98-4.79 (m, 4H), 4.51 (q, J=7.1 Hz, 4H), 4.37 (m, 2H), 4.16 (m, 2H), 2.79 (m, 2H), 2.46 (m, 2H), 2.17 (s, 3H), 2.06 (s, 6H), 1.94 (m, 2H), 1.75 (d, J=12.4 Hz, 2H), 1.50 (t, J=7.0 Hz, 2H), 1.25-1.23 (m, 8H).

Example 16: (E)-1,15-bis(1-ethyl-3-methyl-1H-pyrazole-5-carboxamido)-8-(morpholinomethyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 16)

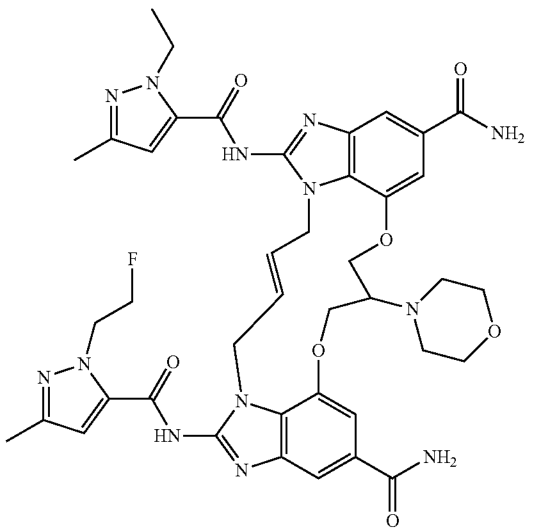 [SMILES: CCn1nc(C)cc1C(=O)Nc1nc2cc(C(N)=O)cc3c2n1C/C=C/Cn1c(NC(=O)c2cc(C)nn2CCF)nc2cc(C(N)=O)cc(c21)OCC(N1CCOCC1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 4-(3-chloro-2-(chloromethyl)propyl)morpholine.

LCMS (ESI): m/z 848.18 $(M+H)^+$ $^1H$ NMR (400 MHz, DMSO-$d_6$) δ 12.91 (brs, 2H), 8.24 (s, 1H), 8.01 (brs, 2H), 7.70 (d, J=1.2 Hz, 2H), 7.62 (s, 2H), 7.39 (brs, 2H), 6.53 (s, 2H), 5.39 (s, 2H), 4.88 (s, 4H), 4.61-4.38 (m, 6H), 4.23 (t, J=4 Hz, 2H), 3.68 (t, J=4.5 Hz, 4H), 2.06 (s, 8H), 1.28-1.22 (m, 6H).

Example 17: (E)-15-(1-ethyl-3-methyl-1H-pyrazole-5-carboxamido)-1-(1-(2-fluoroethyl)-3-methyl-1H-pyrazole-5-carboxamido)-8-morpholino-8,9,16,19-tetrahydro-7H-6,10-dioxa-2,14,15a,19a-tetraazacyclopentadeca[3,2,1-cd:8,9,10-c'd'] diindene-4,12-dicarboxamide (Compound 17)

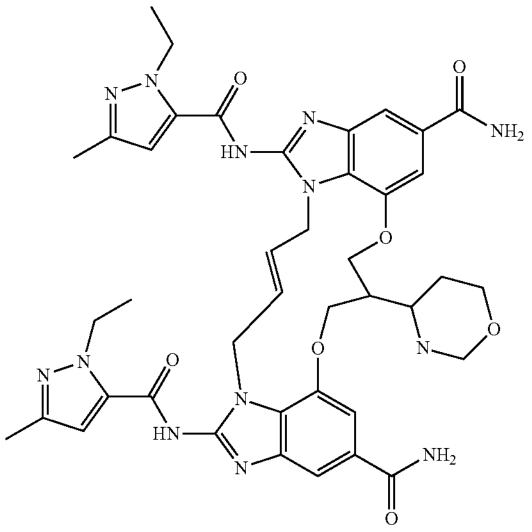 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(C1CCOCN1)CO3]

Step-1: Tert-butyl (E)-(4-((4-carbamoyl-2-((4-methoxybenzyl)oxy)-6-nitrophenyl)amino) but-2-en-1-yl)carbamate

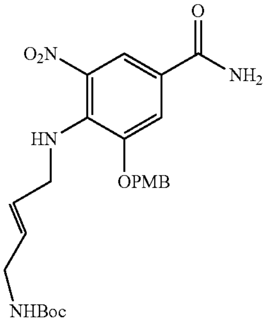

In a 250 ml sealed tube, to a solution of 4-chloro-3-((4-methoxybenzyl)oxy)-5-nitrobenzamide (Step 1 product of example 1, 24.00 g, 71.3 mmol) in ethanol (100 ml), tert-butyl (E)-(4-aminobut-2-en-1-yl)carbamate (19.91 g, 107 mmol) was added followed by addition of diisopropylethylamine (62.2 ml, 356 mmol) and heated at 120° C. for 16 hr. LCMS of the aliquot showed starting amide unreacted, so added another 0.6 eq of tert-butyl (E)-(4-aminobut-2-en-1-yl)carbamate and reaction continued for another 16 hr. Progress of the reaction was monitored by TLC. The mixture was cooled, the red solid was filtered and washed with ethanol. The compound was purified by combiflash chromatography using methanol in DCM. The desired product was eluted at 4-5% of methanol in dichloromethane to obtain the title compound (14.0 g, 40.4% yield).

LCMS (ESI): m/z 487.36 $(M+H)^+$ $^1$H NMR (400 MHz, DMSO-$d_6$) δ 8.22 (d, J=2.0 Hz, 1H), 8.02 (s, 1H), 7.82-7.67 (m, 2H), 7.48-7.40 (m, 2H), 7.34 (s, 1H), 7.03-6.89 (m, 3H), 5.55-5.37 (m, 2H), 5.12 (s, 2H), 4.06 (t, J=5.6 Hz, 2H), 3.77 (s, 3H), 3.45 (t, J=5.3 Hz, 2H), 1.36 (s, 9H).

Step-2: Tert-butyl (E)-(4-((2-amino-4-carbamoyl-6-((4-methoxybenzyl)oxy)phenyl)amino) but-2-en-1-yl)carbamate

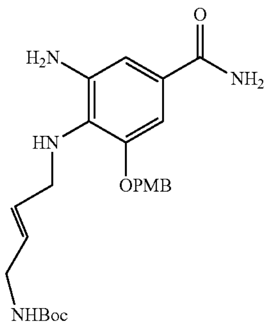

In a round bottom flask, to a stirred solution of tert-butyl (E)-(4-((4-carbamoyl-2-((4-methoxybenzyl)oxy)-6-nitrophenyl)amino)but-2-en-1-yl)carbamate (Step 1, 14.00 g, 28.8 mmol) in methanol (500 ml) at 0° C., was added sodium dithionite (29.7 g, 144 mmol) in methanol:THF (50 ml, 1:1) followed by addition of ammonium hydroxide (53.8 ml, 345 mmol). The reaction mixture was allowed to warm at room temperature for 30 min. Reaction was monitored by TLC. The mixture was diluted with water (100 ml) and ethyl acetate (300 ml). Organic layer was separated and aqueous layer was extracted with ethyl acetate (300×3). The combined organic layer was dried over sodium sulphate and concentrated under vacuum to give the title compound as brown solid (11.5 g, 88% yield).

LCMS (ESI): m/z 457.50 $(M+H)^+$ $^1$H NMR (400 MHz, DMSO-$d_6$) δ 7.62 (s, 1H), 7.40 (m, 2H), 7.06-6.80 (m, 5H), 5.67-5.41 (m, 2H), 5.01 (d, J=8.2 Hz, 2H), 4.70 (s, 1H), 3.77 (s, 3H), 3.53 (s, 3H), 3.34 (s, 2H), 1.37 (s, 9H).

Step-3: Tert-butyl (E)-(4-(5-carbamoyl-2-(1-ethyl-3-methyl-1H-pyrazole-5-carboxamido)-7-((4-methoxybenzyl)oxy)-1H-benzo[d]imidazol-1-yl)but-2-en-1-yl)carbamate

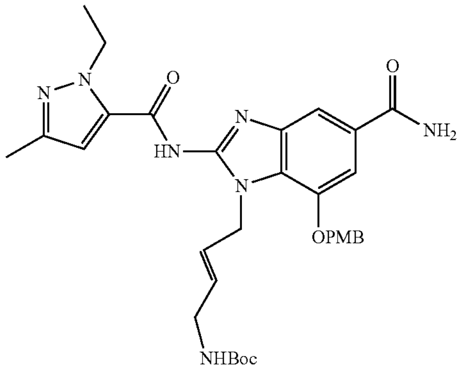

In a round bottom flask, to a stirred solution of tert-butyl (E)-(4-((2-amino-4-carbamoyl-6-((4-methoxybenzyl)oxy) phenyl)amino)but-2-en-1-yl)carbamate (step 2, 11 g, 24.09 mmol) in dimethylformamide (100 ml), 1-ethyl-3-methyl-1H-pyrazole-5-carbonyl isothiocyanate (4.70 g, 24.09 mmol) in 1 ml of dimethylformamide was added at 0° C. and stirred for 30 min. To this reaction mixture, EDC (6.93 g, 36.1 mmol) and triethylamine (10.08 ml, 72.3 mmol) were added at 0° C. and stirred for 18 hr. After completion the mixture was concentrated under reduced pressure. Water was added, a resulting solid was filtered and dried to get the title compound (11.5 g, 18.62 mmol, 77% yield).

LCMS (ESI): m/z 618.46 $(M+H)^+$ $^1$H NMR (400 MHz, DMSO-$d_6$) δ 12.86 (s, 1H), 8.00 (s, 1H), 7.67 (d, J=1.2 Hz, 1H), 7.53 (d, J=1.4 Hz, 1H), 7.50-7.46 (m, 2H), 7.38 (d, J=7.5 Hz, 1H), 7.08-6.87 (m, 5H), 6.61 (s, 1H), 5.67 (d, J=15.3 Hz, 1H), 5.38 (m, 1H), 5.22 (s, 2H), 4.85 (d, J=6.8 Hz, 2H), 4.60 (q, J=7.0 Hz, 2H), 3.78 (d, J=8.1 Hz, 5H), 3.44 (m, 2H), 2.17 (s, 4H), 1.32 (s, 9H).

Step 4: (E)-1-(4-aminobut-2-en-1-yl)-2-(1-ethyl-3-methyl-1H-pyrazole-5-carboxamido)-7-((4-methoxybenzyl)oxy)-1H-benzo[d]imidazole-5-carboxamide hydrochloride

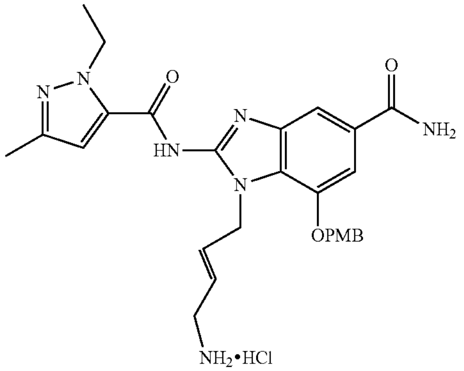

In a round bottom flask, tert-butyl (E)-(4-(5-carbamoyl-2-(1-ethyl-3-methyl-1H-pyrazole-5-carboxamido)-7-((4-methoxybenzyl)oxy)-1H-benzo[d]imidazol-1-yl)but-2-en-1-yl)carbamate (step 3, 11.45 g, 18.54 mmol) was dissolved in dichloromethane (150.00 ml) and a methanol (~15 ml) was added to it. To the solution, was added hydrochloric acid (4 M in dioxane) (46.3 ml, 185 mmol) slowly. The reaction mixture was stirred at room temperature for 2 hr. Upon completion, the reaction mixture was concentrated and the solid obtained was triturated with diethyl ether to get the title compound (10.0 g, 97% yield).

LCMS (ESI): m/z 518.36 $(M+H)^+$ $^1$H NMR (400 MHz, DMSO-$d_6$) δ 7.69 (d, J=1.2 Hz, 2H), 7.59 (d, J=1.4 Hz, 2H), 7.56-7.45 (m, 3H), 7.43-7.33 (m, 2H), 7.09-6.99 (m, 3H), 6.71 (m, 1H), 6.02-5.92 (m, 1H), 5.56-5.43 (m, 1H), 5.27 (s, 2H), 4.94 (d, J=5.6 Hz, 2H), 4.60 (q, J=6.8 Hz, 2H), 3.77 (m, 4H), 3.43-3.31 (m, 2H), 2.19 (d, J=4.4 Hz, 2H), 1.36 (m, 3H).

Step 5: (E)-1-(4-((4-carbamoyl-2-((4-methoxybenzyl)oxy)-6-nitrophenyl)amino)but-2-en-1-yl)-2-(1-ethyl-3-methyl-1H-pyrazole-5-carboxamido)-7-((4-methoxybenzyl)oxy)-1H-benzo[d]imidazole-5-carboxamide

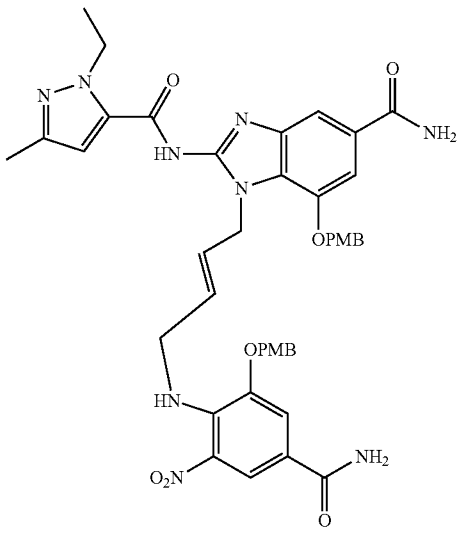

In a round bottom flask, (E)-1-(4-aminobut-2-en-1-yl)-2-(1-ethyl-3-methyl-1H-pyrazole-5-carboxamido)-7-((4-methoxybenzyl)oxy)-1H-benzo[d]imidazole-5-carboxamide hydrochloride (9.95 g, 17.96 mmol) and 4-chloro-3-((4-methoxybenzyl)oxy)-5-nitrobenzamide (step 4, 6.05 g, 17.96 mmol) was suspended in isopropyl alcohol (100 ml) and diisopropylethylamine (25.09 ml, 144 mmol) was added and the mixture heated at 115° C. in a sealed tube for 36 hrs. The progress of the reaction was monitored by LCMS. Upon completion (~10% of starting observed) the reaction mixture was concentrated under reduced pressure and was purified by column chromatography using ethyl acetate in hexane, to remove the starting compound. Then the desired compound was eluted at ~10-15% of methanol in dichloromethane to obtained the title compound (10.5 g, 71.5% yield).

LCMS (ESI): m/z 818.61 $(M+H)^+$ $^1$H NMR (400 MHz, DMSO-$d_6$) δ 9.34 (br s, 2H), 8.05 (s, 1H), 7.34 (m, 3H), 7.17 (d, J=8.6 Hz, 1H), 6.89-6.81 (m, 1H), 6.76 (d, J=8.7 Hz, 1H), 4.92-4.72 (m, 2H), 4.55 (q, J=7.2 Hz, 2H), 4.00 (s, 2H), 3.77-3.68 (m, 3H), 3.59 (m, 8H), 3.35 (m, 8H), 3.12 (m, 6H), 2.16 (m, 2H).

Step 6: (E)-1-(4-((2-amino-4-carbamoyl-6-((4-methoxybenzyl)oxy)phenyl)amino)but-2-en-1-yl)-2-(1-ethyl-3-methyl-1H-pyrazole-5-carboxamido)-7-((4-methoxybenzyl)oxy)-1H-benzo[d]imidazole-5-carboxamide

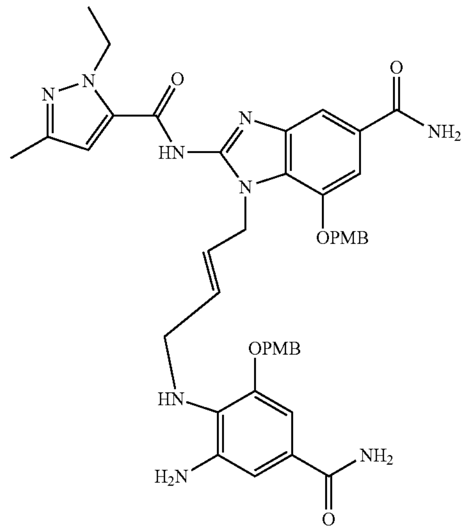

(E)-1-(4-((4-carbamoyl-2-((4-methoxybenzyl)oxy)-6-nitrophenyl)amino)but-2-en-1-yl)-2-(l-ethyl-3-methyl-1H-pyrazole-5-carboxamido)-7-((4-methoxybenzyl)oxy)-1H-benzo[d]imidazole-5-carboxamide (step 7, 10 g, 12.23 mmol) was dissolved in 50 mL methanol. The solution was cooled to 0° C. and a solution of sodium dithionite (12.60 g, 61.1 mmol) in 25 ml water was added to it followed by 28% aqueous solution of ammonium hydroxide (22.85 ml, 147 mmol). The reaction mixture was allowed to warm to room temperature and stirred for 2 h after which TLC indicated completion of reaction. The volatiles were then concentrated on rotavapour and the crude product precipitated out. The solid obtained was stirred with 20% MeOH-DCM and then filtered to obtain the product (7.5 g, 78% yield).

LCMS (ESI): m/z 788.73 $(M+H)^+$ $^1$H NMR (400 MHz, DMSO-$d_6$) δ 8.05 (s, 2H), 7.65 (m, 3H), 7.51 (t, J=1.6 Hz, 2H), 7.43-7.35 (m, 4H), 7.21 (m, 2H), 6.99 (m, 2H), 6.94-6.86 (m, 4H), 6.85-6.76 (m, 2H), 6.61 (dq, J=8.4, 4.1 Hz, 1H), 5.71 (m, 1H), 5.19-5.04 (m, 3H), 4.87-4.76 (m, 4H), 4.70-4.47 (m, 4H), 3.53 (m, 5H), 2.23-2.10 (m, 4H), 1.32-1.27 (m, 4H).

Step 7: (E)-1-(4-(5-carbamoyl-2-(1-(2-fluoroethyl)-3-methyl-1H-pyrazole-5-carboxamido)-7-((4-methoxybenzyl)oxy)-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide

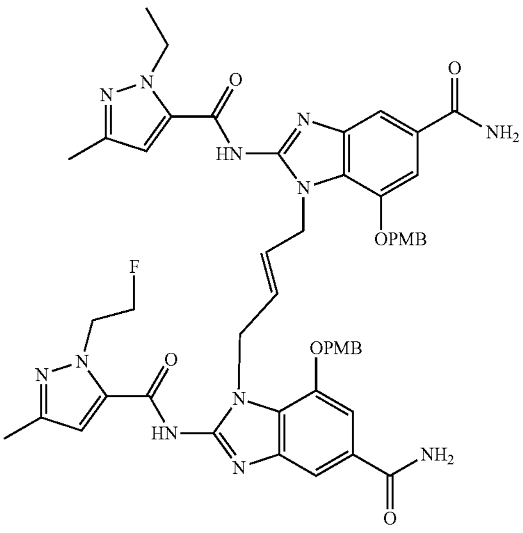

(E)-1-(4-((2-amino-4-carbamoyl-6-((4-methoxybenzyl)oxy)phenyl)amino)but-2-en-1-yl)-2-(1-ethyl-3-methyl-1H-pyrazole-5-carboxamido)-7-((4-methoxybenzyl)oxy)-1H-benzo[d]imidazole-5-carboxamide (4.5 g, 5.71 mmol) was dissolved in 50 mL DMF and the solution cooled to 0° C. and a solution of 1-(2-fluoroethyl)-3-methyl-1H-pyrazole-5-carbonyl isothiocyanate (Intermediate 3, 1.22 g, 5.71 mmol) in 5 mL DMF was added to it. The reaction mixture was stirred at 0° C. for 30 minutes after which 3-(ethyliminomethylideneamino)-N,N-dimethylpropan-1-amine; hydrochloride (1.64 g, 8.57 mmol) was added to the reaction mixture followed by the addition of triethylamine (2.39 mL, 17.13 mmol). The reaction mixture was allowed to warm to RT and stirred overnight. The progress of the reaction was monitored by LCMS and upon completion, the reaction mixture was concentrated under reduced pressure and water was added. The solid precipitate obtained was filtered to get the crude product (2.3 g, 41.6% yield).

LCMS (ESI): m/z 967.70 $(M+H)^+$ $^1H$ NMR (400 MHz, DMSO-$d_6$) δ 12.91 (s, 2H), 7.98 (s, 2H), 7.74 (s, 2H), 7.40 (m, 4H), 7.14-6.97 (m, 3H), 6.82-6.64 (m, 4H), 6.55 (m, 2H), 5.48 (s, 2H), 4.99-4.73 (m, 10H), 4.70-4.45 (m, 3H), 3.61 (s, 6H), 3.33 (s, 4H), 2.12 (d, J=5.6 Hz, 6H), 1.35-1.23 (m, 4H)

Step 8: (E)-1-(4-(5-carbamoyl-2-(1-(2-fluoroethyl)-3-methyl-1H-pyrazole-5-carboxamido)-7-hydroxy-1H-benzo[d]imidazol-1-yl)but-2-en-1-yl)-2-(1-ethyl-3-methyl-1H-pyrazole-5-carboxamido)-7-hydroxy-1H-benzo[d]imidazole-5-carboxamide

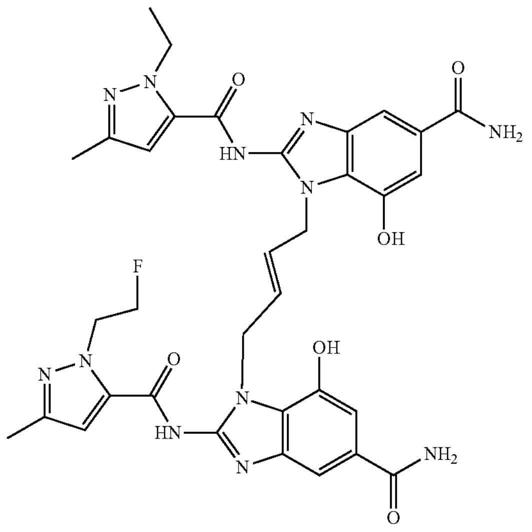 [SMILES: CCn1nc(C)cc1C(=O)Nc1nc2cc(C(N)=O)cc(O)c2n1C/C=C/Cn1c(NC(=O)c2cc(C)nn2CCF)nc2cc(C(N)=O)cc(O)c21]

(E)-1-(4-(5-carbamoyl-2-(1-(2-fluoroethyl)-3-methyl-1H-pyrazole-5-carboxamido)-7-((4-methoxybenzyl)oxy)-1H-benzo[d]imidazol-1-yl)but-2-en-1-yl)-2-(1-ethyl-3-methyl-1H-pyrazole-5-carboxamido)-7-((4-methoxybenzyl)oxy)-1H-benzo[d]imidazole-5-carboxamide (Product from Step 9, 2.2 g, 2.28 mmol) was dissolved in 50 mL DCM and trifluoroacetic acid (5.19 g, 45.5 mmol) was added and the reaction mixture stirred at room temperature for 16 h. The progress of the reaction was monitored by LCMS and upon completion, the reaction mixture was concentrated under reduced pressure and diethyl ether was added resulting in the precipitation of the product as a solid which was filtered and washed with ether (1.6 g, 97% yield).

LCMS (ESI): m/z 727.53 $(M+H)^+$ $^1H$ NMR (400 MHz, DMSO-$d_6$) δ 10.47 (s, 2H), 7.91-7.74 (m, 2H), 7.50-7.41 (m, 3H), 7.23 (s, 2H), 7.17-7.08 (m, 2H), 6.53 (m, 2H), 5.95 (m, 2H), 4.96 (s, 4H), 4.92-4.72 (m, 4H), 4.66 (t, J=5.1 Hz, 1H), 4.51 (q, J=7.1 Hz, 2H), 2.11 (m, 6H), 1.25 (t, J=7.1 Hz, 4H).

Step 9: (E)-15-(1-ethyl-3-methyl-1H-pyrazole-5-carboxamido)-1-(1-(2-fluoroethyl)-3-methyl-1H-pyrazole-5-carboxamido)-8-morpholino-8,9,16,19-tetrahydro-7H-6,10-dioxa-2,14,15a,19a-tetraazacyclopentadeca[3,2,1-cd:8,9,10-c'd']diindene-4,12-dicarboxamide formic acid salt (Compound 17)

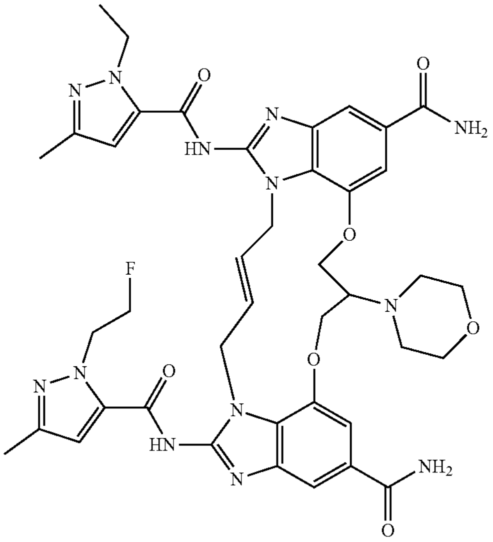 [SMILES: CCn1nc(C)cc1C(=O)Nc1nc2cc(C(N)=O)cc3c2n1C/C=C/Cn1c(NC(=O)c2cc(C)nn2CCF)nc2cc(C(N)=O)cc(c21)OCC(N1CCOCC1)CO3]

The title compound was prepared by following the procedure outlined for step 6 of Example 1 using (E)-1-(4-(5-carbamoyl-2-(1-(2-fluoroethyl)-3-methyl-1H-pyrazole-5-carboxamido)-7-hydroxy-1H-benzo[d]imidazol-1-yl)but-2-en-1-yl)-2-(1-ethyl-3-methyl-1H-pyrazole-5-carboxamido)-7-hydroxy-1H-benzo[d]imidazole-5-carboxamide (step 8 product) and 4-(1,3-dichloropropan-2-yl)morpholine.

LCMS (ESI): m/z 852.5 $(M+H)^+$ $^1$H NMR (400 MHz, DMSO-$d_6$) δ 8.01 (s, 2H), 7.77-7.71 (m, 2H), 7.66 (s, 2H), 7.41 (s, 2H), 6.57 (d, J=21.9 Hz, 2H), 5.53 (s, 2H), 4.99-4.86 (m, 4H), 4.86-4.74 (m, 2H), 4.72-4.59 (m, 3H), 4.53 (q, J=7.1 Hz, 2H), 4.21 (dd, J=10.4, 6.2 Hz, 2H), 3.76-3.62 (m, 4H), 3.15 (q, J=5.4 Hz, 1H), 2.83 (q, J=6.1, 4.7 Hz, 4H), 2.09-2.04 (m, 6H), 1.28-1.22 (m, 3H).

Example 18: (E)-1,15-bis(1-ethyl-3-methyl-1H-pyrazole-5-carboxamido)-8-((4-methylpiperazin-1-yl)methyl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 18)

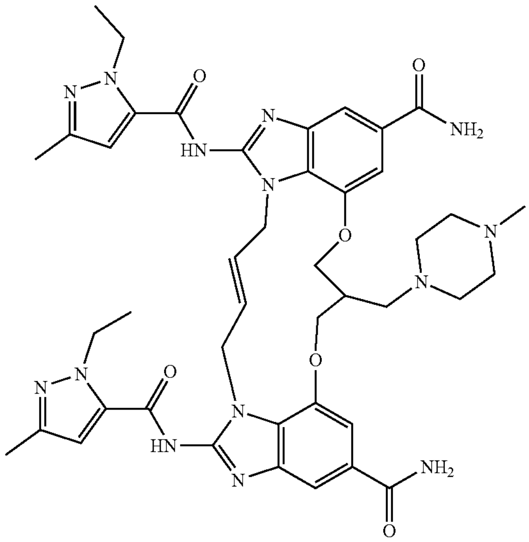

The title compound as its dihydrochloride salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 1-(3-chloro-2-(chloromethyl)propyl)-4-methylpiperazine dihydrochloride.

LCMS (ESI): m/z 861.68 $(M+H)^+$ $^1$H NMR (400 MHz, DMSO-$d_6$) δ 8.04 (brs, 2H), 7.95 (brs, 2H), 7.77 (s, 2H), 7.46 (brs, 2H), 6.57-6.55 (s, 2H), 5.42 (s, 2H), 4.92 (s, 6H), 4.51 (q, J=7.1 Hz, 6H), 4.38-4.36 (m, 2H), 2.90-2.88 (s, 3H), 2.60-2.53 (m, 2H), 2.50 (s, 3H), 2.06 (s, 6H), 1.55-1.53 (m, 1H), 1.26-1.23 (m, 6H).

Example 19: (E)-1,15-bis(1-ethyl-3-methyl-1H-pyrazole-5-carboxamido)-8-(1H-imidazol-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 19)

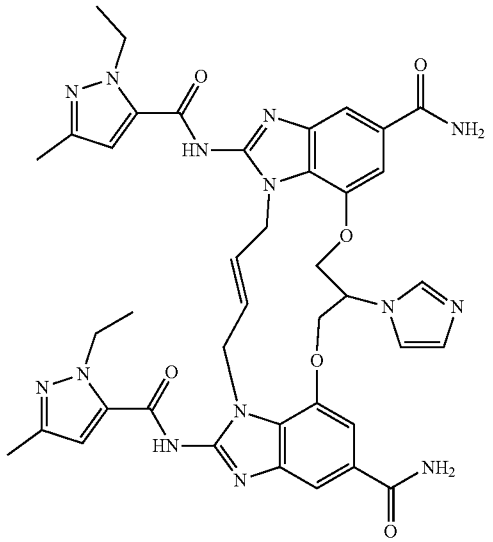 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(n1ccnc1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 1-(1,3-dichloropropan-2-yl)-1H-imidazole.

LCMS (ESI): m/z 815.67 $(M+H)^+$ $^1$H NMR (400 MHz, DMSO-$d_6$) δ 7.96 (s, 2H), 7.81 (s, 1H), 7.68 (s, 1H), 7.50-7.39 (m, 4H), 7.22 (s, 1H), 7.14 (s, 1H), 6.99 (s, 1H), 6.47 (s, 2H), 5.75-5.58 (m, 2H), 5.35 (s, 1H), 5.12 (d, J=9.8 Hz, 3H), 4.94-4.82 (m, 2H), 4.69-4.61 (m, 2H), 4.56-4.40 (m, 5H), 2.09 (s, 6H), 1.25-1.17 (m, 6H).

Example 20: (33R,35R,E)-12,62-bis(1-ethyl-3-methyl-1H-pyrazole-5-carboxamido)-11H,61H-2,5-dioxa-1,6(7,1)-dibenzo[d]imidazola-3(3,5)-pyrrolidinacyclodecaphan-8-ene-15,65-dicarboxamide (Compound 20)

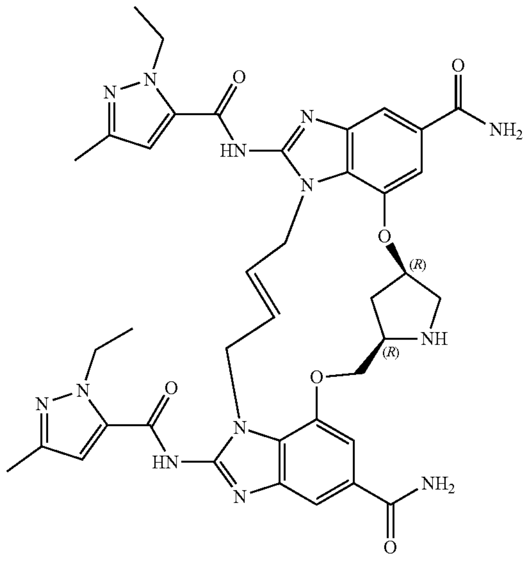

The title compound as its hydrochloride salt was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and tert-butyl (2R,4R)-4-(tosyloxy)-2-((tosyloxy)methyl)pyrrolidine-1-carboxylate followed by deprotection of the Boc group and conversion to its salt.

LCMS (ESI): m/z 789.91 $(M+H)^+$ $^1$H NMR (400 MHz, DMSO-$d_6$) δ 10.44 (s, 1H), 9.14 (s, 1H), 8.13 (brs, 2H), 7.76 (s, 1H), 7.74 (s, 1H), 7.62 (brs, 1H), 7.47-7.40 (m, 3H), 6.59-6.57 (m, 2H), 6.00 (s, 1H), 5.81 (s, 1H), 5.58 (s, 1H), 5.26-5.07 (m, 2H), 4.90 (s, 2H), 4.61-4.51 (m, 6H), 4.32-4.22 (m, 1H), 3.94-3.84 (m, 1H), 2.98-2.87 (m, 1H), 2.06 (s, 3H), 2.01 (s, 3H), 1.29 (t, J=7.1 Hz, 6H).

Example 21: (33R,35R,E)-12,62-bis(1-ethyl-3-methyl-1H-pyrazole-5-carboxamido)-31-methyl-11H,61H-2,5-dioxa-1,6(7,1)-dibenzo[d]imidazola-3(3,5)-pyrrolidinacyclodecaphan-8-ene-15,65-dicarboxamide (Compound 21)

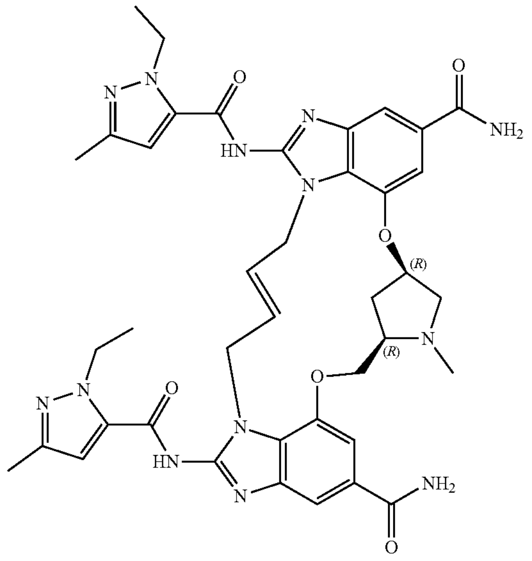

To a stirred solution of (33S,35R,E)-12,62-bis(1-ethyl-3-methyl-1H-pyrazole-5-carboxamido)-11H,61H-2,5-dioxa-1,6(7,1)-dibenzo[d]imidazola-3(3,5)-pyrrolidinacyclodecaphan-8-ene-15,65-dicarboxamide (0.015 g, 0.019 mmol) [Example 20] in 3 mL of MeOH-DCM (1:2) was added formaldehyde (0.035 g, 0.38 mmol) and stirred for 2 h at 25° C. after which sodium triacetoxyborohydride (8.05 mg, 0.038 mmol) was added and stirred for 1 h at 25° C. The reaction was monitored by LCMS and after completion the volatiles were conc. under reduced pressure and water was added. The solid precipitated was filtered and dried to get the crude product which was purified by prep HPLC and converted to the hydrochloride salt.

LCMS (ESI): m/z 804.6 $(M+H)^+$ $^1H$ NMR (400 MHz, DMSO-$d_6$) δ 8.13 (s, 2H), 7.76 (m, 3H), 7.45 (s, 3H), 6.59 (s, 2H), 6.16-5.99 (m, 1H), 5.99-5.81 (m, 1H), 5.78-5.56 (m, 1H), 5.17-4.79 (m, 4H), 4.66-4.48 (m, 6H), 3.10 (s, 3H), 2.07 (s, 3H), 2.03 (s, 3H), 1.32-1.27 (m, 6H).

Example 22: (E)-1,15-bis(1-ethyl-3-methyl-1H-pyrazole-5-carboxamido)-8-(4-hydroxypiperidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 22)

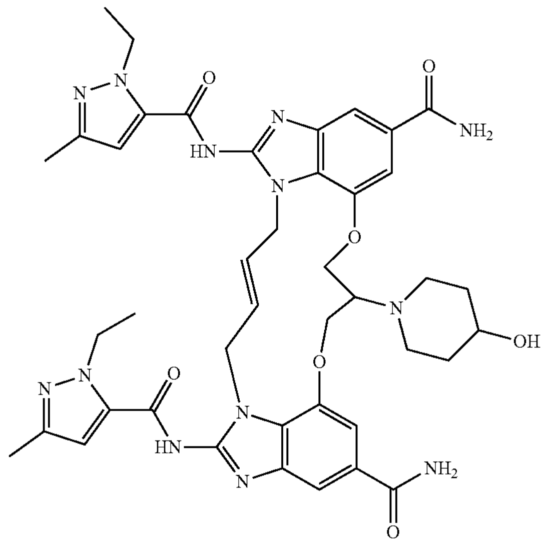 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(O)CC1)CO3]

The title compound as its hydrochloride salt was prepared by following the procedure outlined for Example 11 using methyl 4-chloro-3-hydroxy-5-nitrobenzoate and 2-(4-((tert-butyldimethylsilyl)oxy)piperidin-1-yl)propane-1,3-diol followed by deprotection of the TBS group and conversion to its salt.

LCMS (ESI): m/z 848.18 $(M+H)^+$ $^1H$ NMR (400 MHz, DMSO-$d_6$) δ 11.25 (s, 1H), 8.14 (s, 2H), 7.95 (d, J=6.8 Hz, 2H), 7.82-7.76 (m, 2H), 7.49 (s, 2H), 6.52 (s, 2H), 5.43-5.23 (m, 2H), 5.13 (d, J=11.2 Hz, 2H), 4.92-4.87 (m, 4H), 4.50-4.43 (m, 4H), 4.45-4.31 (m, 2H), 3.68-3.63 (m, 2H), 3.57-3.43 (m, 2H), 2.40-2.48 (m, 4H), 2.03 (s, 6H), 1.25 (t, J=6.9 Hz, 6H).

Example 23: (E)-8-(4-aminopiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 23)

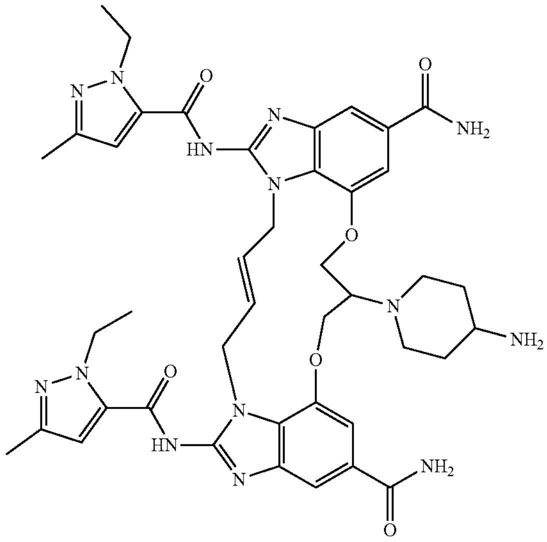 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(N)CC1)CO3]

The title compound as its dihydrochloride salt was prepared by following the procedure outlined for Example 11 using methyl 4-chloro-3-hydroxy-5-nitrobenzoate and tert-butyl (1-(1,3-dihydroxypropan-2-yl)piperidin-4-yl)carbamate followed by deprotection of the Boc group and conversion to its salt.

LCMS (ESI): m/z 847.30 $(M+H)^+$ $^1$H NMR (400 MHz, DMSO-$d_6$) δ 11.85 (s, 2H), 8.41-8.11 (m, 6H), 7.82 (d, J=9.4 Hz, 2H), 7.47 (s, 2H), 6.52 (s, 2H), 5.26 (s, 2H), 4.91 (s, 4H), 4.49 (q, J=7.1 Hz, 4H), 4.38 (d, J=7.7 Hz, 2H), 4.08 (m, 2H), 3.91-3.52 (m, 6H), 2.19 (m, 4H), 2.03 (s, 6H), 1.23 (m, 6H).

Example 24: (S,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl dihydrogen phosphate (Compound 24)

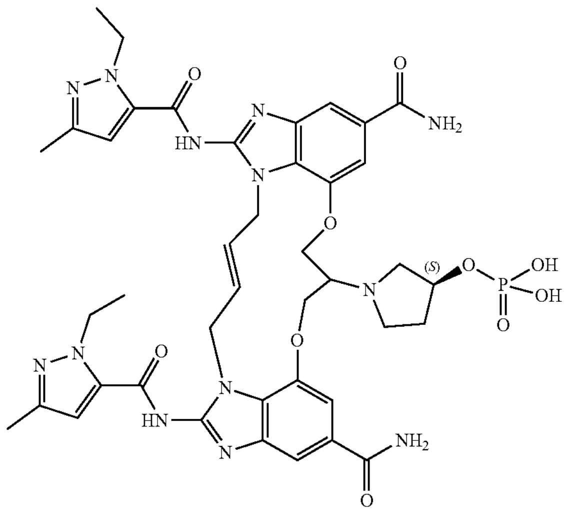

Step 1: Synthesis of (S,E)-di-tert-butyl (1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl) phosphate

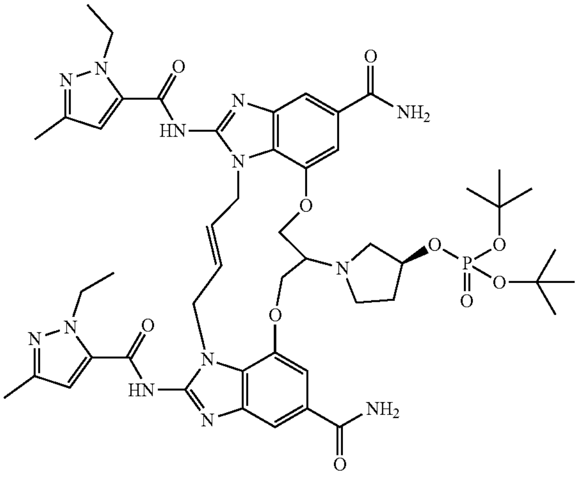 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CC[C@H](OP(=O)(OC(C)(C)C)OC(C)(C)C)C1)CO3]

To (S,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 11, 150 mg, 0.180 mmol) in 2 mL DMF were added 1H-tetrazole (315 mg, 4.50 mmol) and di-tert-butyl diisopropylphosphoramidite (998 mg, 3.60 mmol) at 25° C. The mixture was allowed to stir at 25° C. for 2 hr. Progress of the reaction was monitored by LCMS. Upon complete consumption of the starting material, $H_2O_2$ (30% aqueous solution 1.5 ml, 4.50 mmol) was added at room temperature and stirred for 30 min after which the reaction mixture was poured into 10 ml solution of water containing sodium bicarbonate and sodium thiosulphate. The product precipitated out which was then filtered and purified by preparative HPLC to afford the title compound (20 mg, 11% yield).

LCMS (ESI): m/z 1026.84 $(M+H)^+$

Step 2: Synthesis of (S,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl dihydrogen phosphate

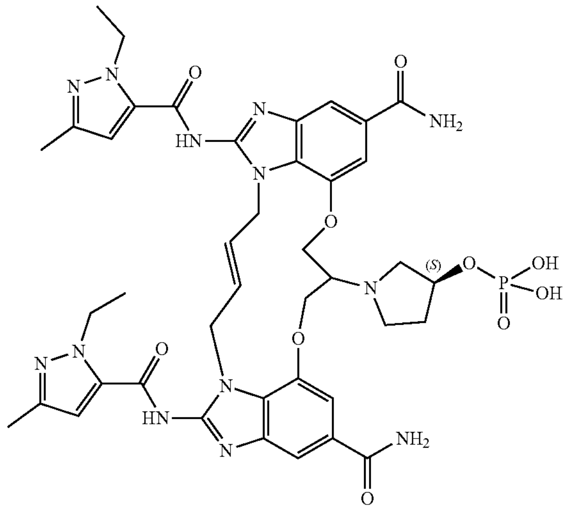

(S,E)-di-tert-butyl (1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidin-3-yl) phosphate (20 mg, 0.019 mmol) obtained from the previous step, was dissolved in 5 ml dichloromethane and 4 N HCl in dioxane (0.236 ml, 0.945 mmol) at room temperature and stirred for 2 h. The progress of the reaction was monitored by LCMS. After completion of the deprotection, the volatiles were concentrated under reduced pressure to get a solid which was triturated with diethyl ether to the hydrochloride salt of the title compound (15 mg, 80% yield).

LCMS (ESI): m/z 913.32 $(M+H)^+$ $^1$H NMR (400 MHz, DMSO-$d_6$) d 8.16 (s, 2H), 7.81 (d, J=5.8 Hz, 4H), 7.46 (s, 2H), 6.53 (s, 2H), 5.33 (d, J=10.2 Hz, 3H), 5.04-4.84 (m, 6H), 4.57-4.33 (m, 8H), 3.41-3.31 (m, 3H), 2.46-2.40 (m, 2H), 2.04 (s, 6H), 1.27-1.23 (m, 6H).

Example 25: (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraaza-cyclopentadeca[3,2,1-cd:8,9,10-c'd']diinden-8-yl)piperidin-4-yl dihydrogen phosphate (Compound 25)

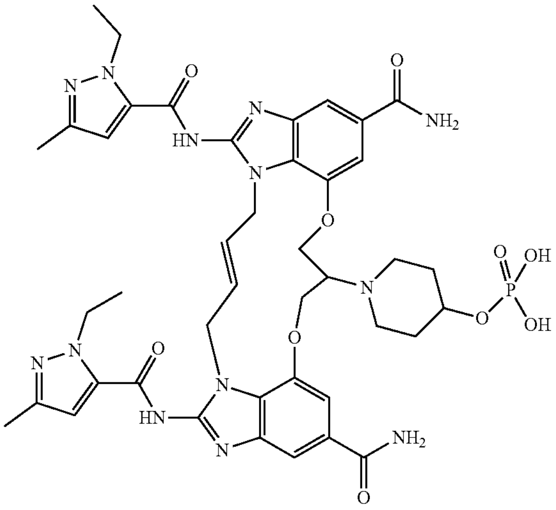 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(OP(=O)(O)O)CC1)CO3]

The title compound as its hydrochloride salt was prepared by following the procedure outlined for Example 24 using (E)-1,15-bis(1-ethyl-3-methyl-1H-pyrazole-5-carboxamido)-8-(4-hydroxypiperidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 22)

LCMS (ESI): m/z 928.32 $(M+H)^+$ $^1$H NMR (400 MHz, DMSO-$d_6$) δ 12.98 (s, 2H), 11.50 (s, 1H), 8.11 (s, 2H), 7.90 (d, J=26.8 Hz, 2H), 7.79 (d, J=4.3 Hz, 2H), 7.49 (s, 2H), 6.52 (s, 2H), 5.36-5.25 (m, 2H), 5.19-5.06 (m, 2H), 4.97-4.87 (m, 3H), 4.63-4.23 (m, 11H), 3.60 (s, 2H), 2.28-2.18 (m, 2H), 2.03 (s, 6H), 1.27-1.22 (m, 6H).

Example 26: (E)-8-(3-cyanopyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd'] diindene-4,12-dicarboxamide (Compound 26)

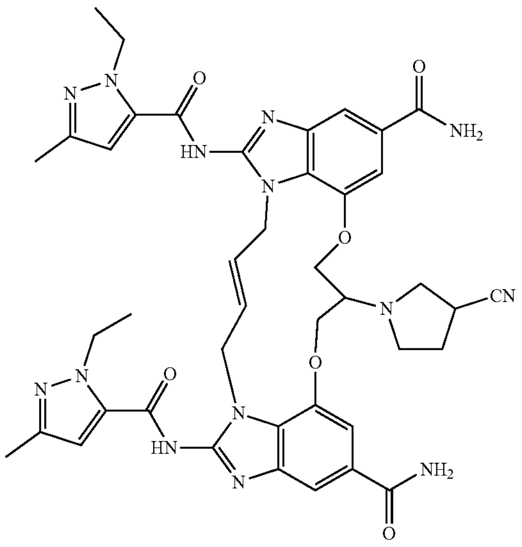 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C#N)C1)CO3]

Step 1: Synthesis of 1-(1,3-dichloropropan-2-yl) pyrrolidine-3-carbonitrile

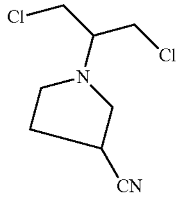 [SMILES: N#CC1CCN(C(CCl)CCl)C1]

A mixture of 1,3-dichloropropan-2-one (2.62 g, 20.60 mmol) and pyrrolidine-3-carbonitrile (1.8 g, 18.72 mmol) in 30 ml THF was stirred for 2 hr at room temp. after which sodium triacetoxyborohydride (5.16 g, 24.34 mmol) was added and reaction mixture was stirred at room temperature for 12 h. After the completion of the reaction, it was quenched by the addition of water and extracted with DCM. The organic layer was washed with brine, dried over sodium sulphate and concentrated under reduced pressure to get crude product which was purified by flash column chromatography to get the product.

LCMS (ESI): m/z 207.01 $(M+H)^+$ $^1$H NMR (400 MHz, Chloroform-d) δ 3.88-3.78 (m, 2H), 3.78-3.69 (m, 2H), 3.32-3.19 (m, 1H), 3.13-3.02 (m, 1H), 3.02-2.91 (m, 3H), 2.90-2.81 (m, 1H), 2.36-2.23 (m, 1H), 2.22-2.13 (m, 1H).

Step 2: Synthesis of dimethyl 5,5'-((2-(3-cyanopyrrolidin-1-yl)propane-1,3-diyl)bis(oxy))bis(4-chloro-3-nitrobenzoate)

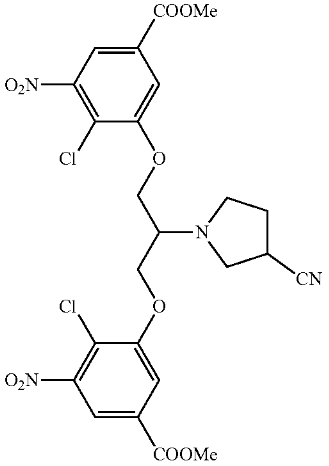 [SMILES: COC(=O)c1cc(OCC(COc2cc(C(=O)OC)cc([N+](=O)[O-])c2Cl)N2CCC(C#N)C2)c(Cl)c([N+](=O)[O-])c1]

Methyl 4-chloro-3-hydroxy-5-nitrobenzoate (2.24 g, 9.66 mmol) and 1-(1,3-dichloropropan-2-yl)pyrrolidine-3-carbonitrile (1.00 g, 4.83 mmol) was dissolved in 50 ml of acetonitrile. DIPEA (5.06 ml, 29.0 mmol) and KI (0.802 g, 4.83 mmol) were added and the reaction mixture stirred at 80° C. for 12 h. The reaction mass was then concentrated under reduced pressure and purified by column chromatography to get dimethyl 5,5'-((2-(3-cyanopyrrolidin-1-yl)propane-1,3-diyl)bis(oxy))bis(4-chloro-3-nitrobenzoate) (1.3 g, 45.1% yield).

LCMS (ESI): m/z 596.83 $(M+H)^+$ $^1$H NMR (400 MHz, Chloroform-$_d$) δ 8.10-8.06 (m, 2H), 7.85-7.80 (m, 2H), 4.55-4.44 (m, 4H), 4.00 (s, 6H), 3.70-3.65 (m, 1H), 3.37-3.28 (m, 1H), 3.25-3.19 (m, 1H), 3.14-3.03 (m, 3H), 2.40-2.19 (m, 2H).

Step 3: dimethyl 5,5'-((2-(3-cyanopyrrolidin-1-yl)propane-1,3-diyl)bis(oxy))bis(4-chloro-3-nitrobenzoate) obtained above was converted to (E)-8-(3-cyanopyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide hydrochloride salt (Compound 26) by following the procedure outlined in Step 4 to Step 8 of Example 11

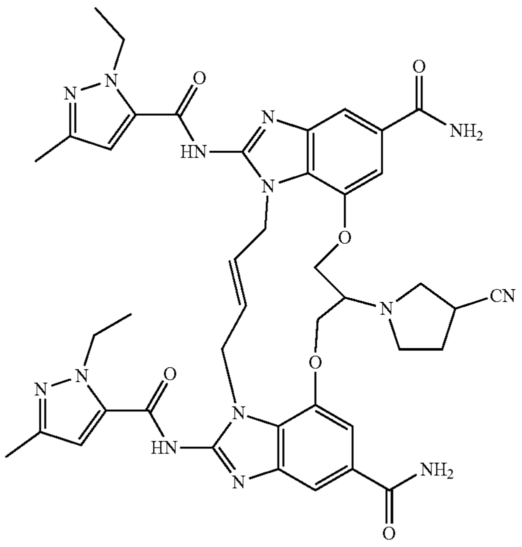 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C#N)C1)CO3]

LCMS (ESI): m/z 843.18 $(M+H)^+$ $^1$H NMR (400 MHz, DMSO-$d_6$) δ 8.10 (s, 2H), 7.85 (s, 2H), 7.80 (d, J=1.4 Hz, 2H), 7.49 (s, 2H), 6.54 (s, 2H), 5.11-4.73 (m, 6H), 4.56-4.42 (m, 6H), 4.35-4.21 (m, 8H), 2.48-2.44 (m, 2H), 2.04 (s, 6H), 1.26-1.23 (m, 6H).

Example 27: (E)-8-(3-aminopyrrolidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 27)

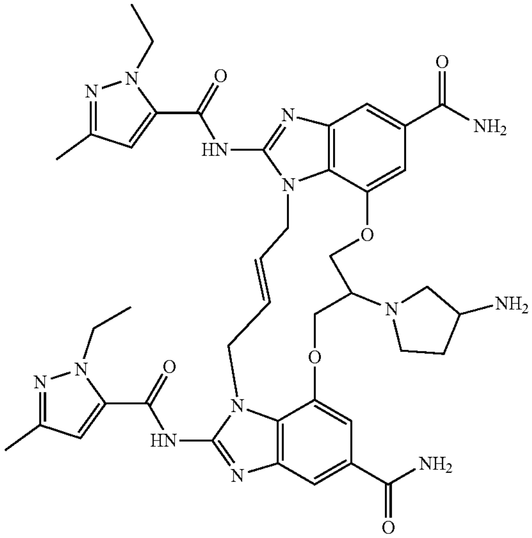 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(N)C1)CO3]

The title compound as its dihydrochloride salt was prepared by following the procedure outlined for Example 26 using methyl 4-chloro-3-hydroxy-5-nitrobenzoate and tert-butyl (1-(1,3-dichloropropan-2-yl)pyrrolidin-3-yl)carbamate followed by deprotection of the Boc group and conversion to its salt.

LCMS (ESI): m/z 833.30 $(M+H)^+$ $^1$H NMR (400 MHz, DMSO-$d_6$) δ 11.85 (s, 2H), 8.41-8.11 (m, 6H), 7.82 (m, 2H), 7.47 (s, 2H), 6.52 (s, 2H), 5.26 (s, 2H), 4.91 (s, 4H), 4.49 (q, J=7.1 Hz, 4H), 4.38 (d, J=7.7 Hz, 2H), 4.08 (m, 2H), 3.91-3.52 (m, 6H), 2.19 (m, 4H), 2.03 (s, 6H), 1.23 (q, J=8.8, 7.8 Hz, 6H).

Example 28: (R,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraaza-cyclopentadeca[3,2,1-cd:8,9,10-c'd']diinden-8-yl) pyrrolidin-3-yl dihydrogen phosphate (Compound 28)

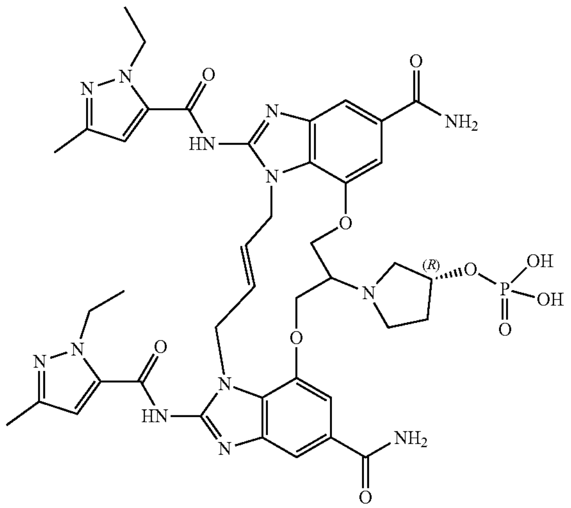

The title compound as its hydrochloride salt was prepared by following the procedure outlined for Example 24 using (R,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 12)

LCMS (ESI): m/z 913.19 $(M+H)^+$

1H NMR (400 MHz, DMSO-d6) δ 12.99 (s, 2H), 8.14 (m, 2H), 7.81 (d, J=6.7 Hz, 4H), 7.47 (s, 2H), 6.53 (s, 2H), 5.33 (d, J=10.8 Hz, 2H), 4.96 (m, 6H), 4.50 (q, J=7.0 Hz, 5H), 4.28-4.20 (m, 5H), 2.59-2.54 (m, 4H), 2.04 (s, 6H), 1.24 (d, J=1.6 Hz, 6H).

Example 29: (E)-8-(4-cyanopiperidin-1-yl)-1,15-bis (1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 29)

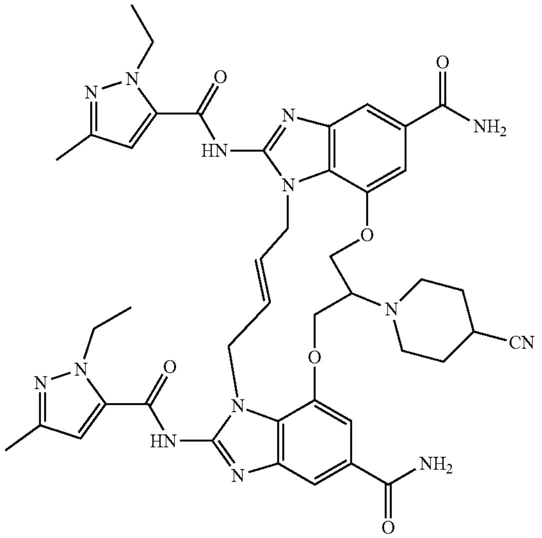 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C#N)CC1)CO3]

The title compound as its hydrochloride salt was prepared by following the procedure outlined for Example 26 using methyl 4-chloro-3-hydroxy-5-nitrobenzoate and 1-(1,3-dichloropropan-2-yl)piperidine-4-carbonitrile.

LCMS (ESI): m/z 857.05 $(M+H)^+$ $^1$H NMR (400 MHz, DMSO-$d_6$) δ 8.00 (s, 2H), 7.63 (d, J=28.0 Hz, 4H), 7.37 (s, 2H), 6.52 (s, 2H), 5.51 (s, 2H), 4.90 (m, 4H), 4.54 (m, 6H), 4.20 (s, 2H), 3.19 (s, 1H), 2.92 (m, 4H), 2.76 (m, 2H), 2.07 (s, 6H), 1.97 (s, 2H), 1.88-1.74 (m, 2H), 1.25 (d, J=8.3 Hz, 6H).

Example 30: (E)-8-(azetidin-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 30)

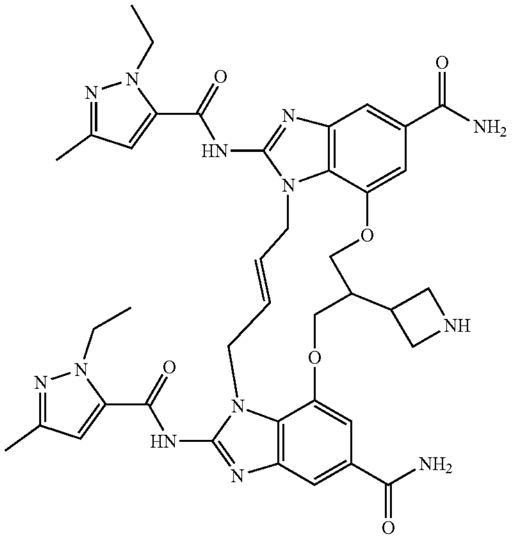 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(C1CNC1)CO3]

The title compound as its hydrochloride salt was prepared by following the procedure outlined for Example 11 using methyl 4-chloro-3-hydroxy-5-nitrobenzoate and tert-butyl 3-(1,3-dihydroxypropan-2-yl)azetidine-1-carboxylate followed by deprotection of the Boc group and conversion to its salt.

LC-MS (ESI): m/z 804.29 $(M+H)^+$ $^1H$ NMR (400 MHz, DMSO-$d_6$) δ 9.22 (s, 1H), 9.07 (s, 1H), 8.09 (s, 2H), 7.75 (d, J=1.2 Hz, 2H), 7.68 (s, 2H), 7.43 (s, 2H), 6.54 (s, 2H), 5.42 (s, 2H), 4.91 (s, 4H), 4.51 (q, J=7.1 Hz, 4H), 4.43 (m, 2H), 4.23-4.05 (m, 6H), 3.18-3.06 (m, 1H), 2.18 (d, J=7.1 Hz, 1H), 2.05 (s, 6H), 1.25 (t, J=6.9 Hz, 6H).

Example 31: (E)-1,15-bis(1-ethyl-3-methyl-1H-pyrazole-5-carboxamido)-8-(piperidin-4-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 31)

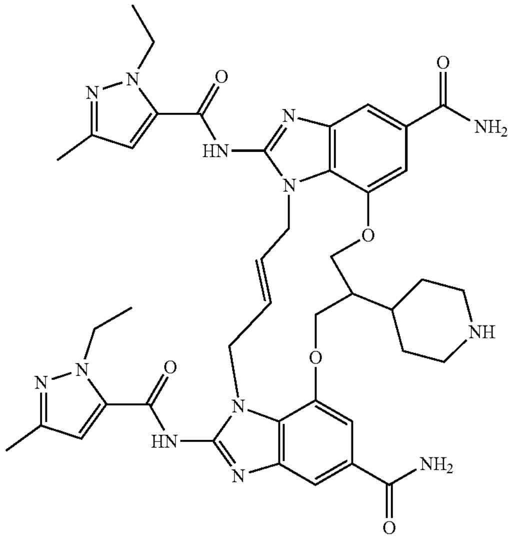 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(C1CCNCC1)CO3]

The title compound as its hydrochloride salt was prepared by following the procedure outlined for Example 11 using methyl 4-chloro-3-hydroxy-5-nitrobenzoate and tert-butyl 4-(1,3-dihydroxypropan-2-yl)piperidine-1-carboxylate followed by deprotection of the Boc group and conversion to its salt.

LCMS (ESI): m/z 832.17 $(M+H)^+$ $^1H$ NMR (400 MHz, DMSO-$d_6$) δ 8.84 (s, 1H), 8.71 (m, 1H), 8.07 (s, 2H), 7.73 (d, J=1.2 Hz, 2H), 7.65 (d, J=1.4 Hz, 3H), 7.42 (s, 2H), 6.54 (s, 2H), 5.44 (s, 2H), 4.92 (m, 4H), 4.51 (q, J=7.3 Hz, 6H), 4.23-4.12 (m, 2H), 3.37 (d, J=7.0 Hz, 2H), 2.96-2.86 (m, 2H), 2.25-2.12 (m, 2H), 2.06 (s, 8H), 1.81 (m, 2H), 1.25 (t, J=7.0 Hz, 6H).

Example 32: (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraaza-cyclopentadeca[3,2,1-cd:8,9,10-c'd']diinden-8-yl) pyrrolidine-3-carboxylic acid (Compound 32)

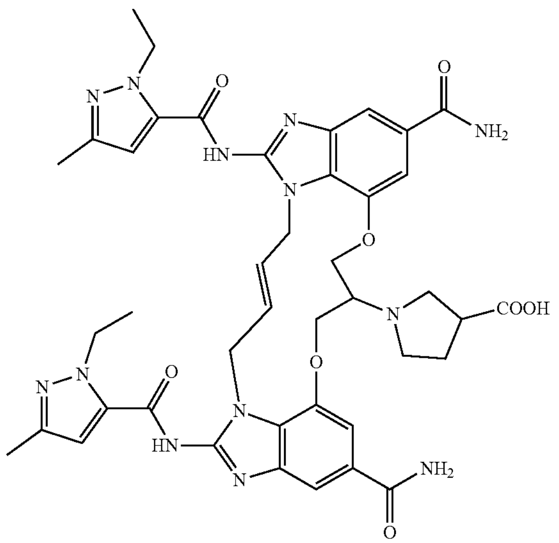 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)O)C1)CO3]

Step 1: Synthesis of methyl (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidine-3-carboxylate

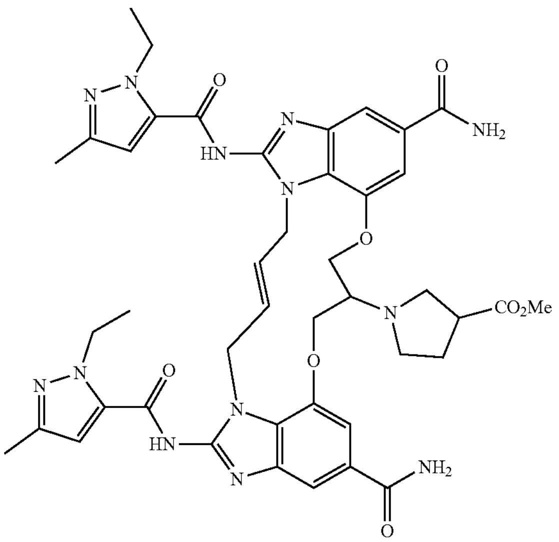 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)OC)C1)CO3]

(E)-8-(3-cyanopyrrolidin-1-yl)-1,15-bis(I-ethyl-3-methyl-1H-pyrazole-5-carboxamido)-8,9,16,19-tetrahydro-7H-6,10-dioxa-2,14,15a,19a tetraazacyclopentadeca[3,2,1-cd:8,9,10-c'd']diindene-4,12-dicarboxamide (50 mg, 0.06 mmol) [Compound 26] was dissolved in 5 mL MeOH and 4 N HCl in Dioxane (1.48 ml, 5.93 mmol) was added to it and stirred for 4 h at room temperature. The reaction was monitored by LCMS, and after conversion to the ester, the reaction mixture was concentrated under reduced pressure and washed with diethyl ether to obtain the title compound. (40 mg, 77% yield)

LCMS (ESI): m/z 876.18 $(M+H)^+$

Step 2: (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl) pyrrolidine-3-carboxylic acid (Compound 32)

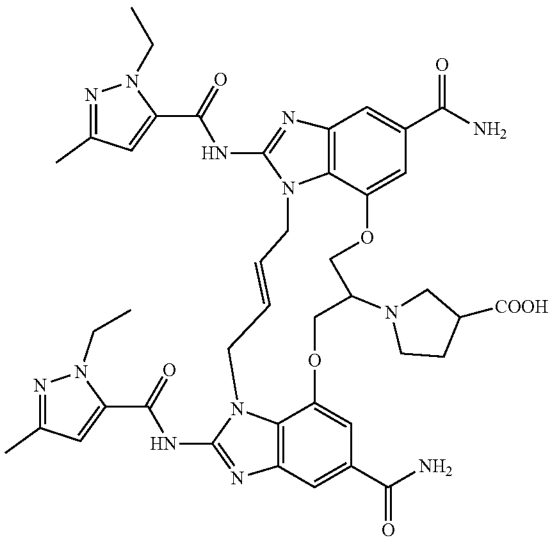 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)O)C1)CO3]

methyl (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diinden-8-yl)pyrrolidine-3-carboxylate hydrochloride (Step 1, 30 mg, 0.033 mmol) was dissolved in a 6 mL mixture of MeOH, THF and Water (1:1:1). Lithium hydroxide hydrate (6.90 mg, 0.164 mmol) was added and the reaction mixture stirred at RT for 15 h. The reaction was monitored by LCMS, and after complete hydrolysis the reaction mixture was conc. under reduced pressure and water was added. The pH of the mixture was adjusted to acidic by the addition of 2 N HCl, and the solid precipitated out was filtered and dried to get the crude product which was purified by prep HPLC to obtain the title product. (10 mg, 34% yield)

LCMS (ESI): m/z 862.18 $(M+H)^+$ $^1H$ NMR (400 MHz, DMSO-$d_6$) δ 12.99 (brs, 1H), 11.55 (brs, 1H), 11.24 (brs, 1H), 8.06 (brs, 2H), 7.80 (d, J=2.8 Hz, 4H), 7.49 (brs, 2H), 6.54 (s, 2H), 5.33 (s, 2H), 5.07-4.80 (m, 6H), 4.61-4.35 (m, 6H), 4.27-4.13 (m, 1H), 4.13-3.99 (m, 1H), 3.95-3.82 (m, 2H), 3.45-3.28 (m, 2H), 2.04 (s, 6H), 1.25 (t, J=7.6 Hz, 6H).

Example 33: (E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a,19a-tetraaza-cyclopentadeca[3,2,1-cd:8,9,10-c'd']diinden-8-yl) piperidine-4-carboxylic acid (Compound 33)

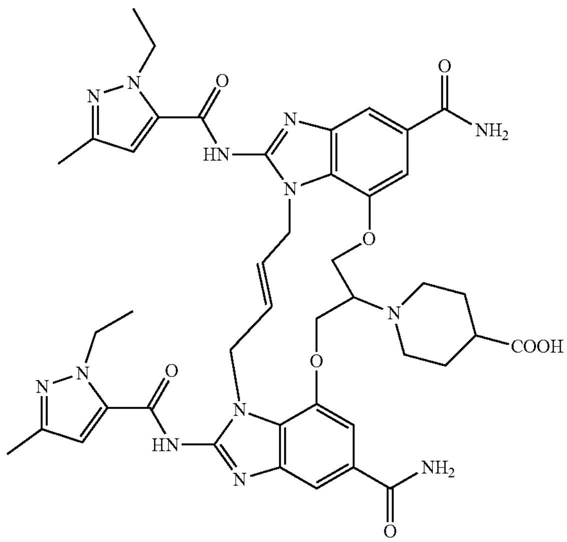 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(N1CCC(C(=O)O)CC1)CO3]

The title compound was prepared from (E)-8-(4-cyanopiperidin-1-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 29) by following the procedure outlined in Example 32.

LCMS (ESI): m/z 876.31 $(M+H)^+$ $^1$H NMR (400 MHz, DMSO-$d_6$) δ 7.90 (brs, 2H), 7.49 (d, J=1.2 Hz, 2H), 7.35 (s, 2H), 7.11 (brs, 2H), 6.38 (s, 2H), 5.33 (s, 2H), 5.00 (m, 2H), 4.83 (d, J=15.7 Hz, 2H), 4.53 (d, J=7.2 Hz, 6H), 4.05-3.99 (m, 4H), 3.00 (d, J=1.9 Hz, 2H), 2.06 (s, 6H), 1.85-1.74 (m, 2H), 1.64-1.56 (m, 2H), 1.22-1.15 (m, 6H).

Example 34: (E)-1,15-bis(1-ethyl-3-methyl-1H-pyrazole-5-carboxamido)-8-(1-methylazetidin-3-yl)-8,9,16,19-tetrahydro-7H-6,10-dioxa-2,14,15a,19a-tetraazacyclopentadeca[3,2,1-cd:8,9,10-c'd'] diindene-4,12-dicarboxamide (Compound 34)

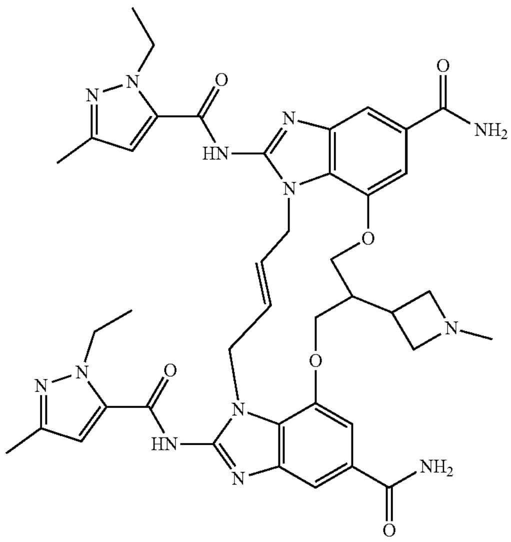

The title compound as its formate salt was prepared by following the reductive amination procedure outlined in Example 21 using (E)-8-(azetidin-3-yl)-1,15-bis(1-ethyl-3-methyl-1H-pyrazole-5-carboxamido)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 30) and purification of the crude product by prep HPLC.

LCMS (ESI): m/z 818.17 $(M+H)^+$ $^1$H NMR (400 MHz, DMSO-$d_6$) δ 12.90 (brs, 2H), 8.02 (brs, 2H), 7.73 (d, J=1.3 Hz, 2H), 7.56 (d, J=1.4 Hz, 2H), 7.40 (s, 2H), 6.53 (s, 2H), 5.41 (s, 2H), 4.89 (s, 4H), 4.51 (q, J=7.1 Hz, 4H), 4.32 (m, 2H), 4.14 (m, 2H), 3.60 (t, J=7.3 Hz, 2H), 3.21 (t, J=7.3 Hz, 2H), 2.33 (s, 3H), 2.06 (s, 6H), 1.27-1.23 (m, 6H).

Example 35: (R,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a,19a-tetraazacyclopentadeca[3,2,1-cd:8,9,10-c'd']diindene-4,12-dicarboxamide (Compound 35)

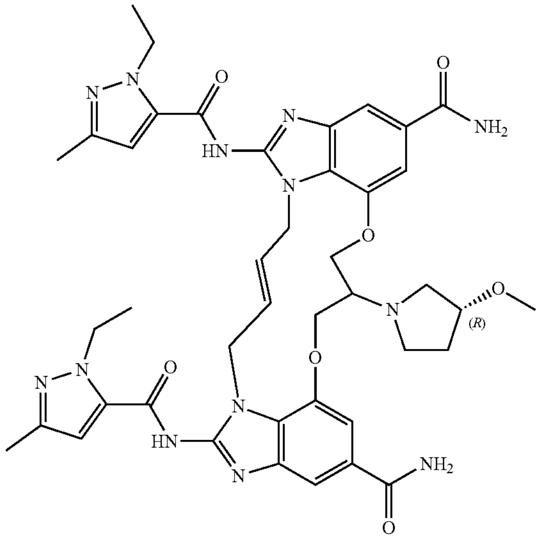

The title compound was prepared by following the procedure outlined for example 2, using diethyl 5,5'-((2-(((trifluoromethyl)sulfonyl)oxy)propane-1,3-diyl)bis(oxy))bis(4-chloro-3-nitrobenzoate) and (R)-3-methoxypyrrolidine in step 4.

LC-MS (ESI): m/z 848.18 $(M+H)^+$ $^1$H NMR (400 MHz, DMSO-$d_6$) δ 12.86 (s, 2H), 8.04 (s, 2H), 7.75 (s, 2H), 7.64 (s, 2H), 7.39 (s, 2H), 6.52 (s, 2H), 5.48 (s, 2H), 4.98-4.79 (m, 4H), 4.64 (d, J=10.6 Hz, 3H), 4.56 (d, J=7.8 Hz, 4H), 4.13 (s, 2H), 3.96 (s, 1H), 3.23 (s, 3H), 3.09 (m, 2H), 2.85 (m, 2H), 2.05 (s, 6H), 1.76 (s, 2H), 1.31 (m, 6H).

Example 36: (E)-1,15-bis(1-ethyl-3-methyl-1H-pyrazole-5-carboxamido)-8-(pyridin-2-yl)-8,9,16,19-tetrahydro-7H-6,10-dioxa-2,14,15a,19a-tetraazacyclopentadeca[3,2,1-cd:8,9,10-c'd']diindene-4,12-dicarboxamidexamide (Compound 36)

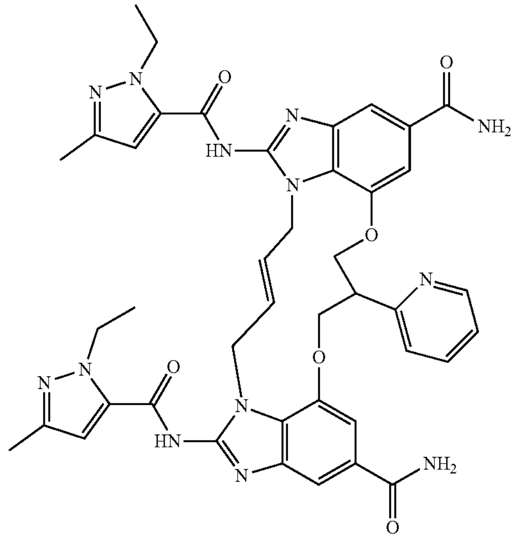 [SMILES: CCn1nc(C)cc1C(=O)Nc1nc2cc(C(N)=O)cc3c2n1C/C=C/Cn1c(NC(=O)c2cc(C)nn2CC)nc2cc(C(N)=O)cc(c21)OCC(c1ccccn1)CO3]

The title compound was prepared by following the procedure outlined for Example 1 using (E)-1,1'-(but-2-ene-1,4-diyl)bis(2-(1-ethyl-3-methyl-1H-pyrazole-5-carboxamido)-7-hydroxy-1H-benzo[d]imidazole-5-carboxamide) and 2-(pyridin-2-yl)propane-1,3-diyl bis(4-methylbenzenesulfonate).

LC-MS (ESI): m/z 826.18 $(M+H)^+$

1H NMR (400 MHz, DMSO-$d_6$) δ 13.00-12.70 (br s, 1H), 10.44 (s, 1H), 8.59 (m, 1H), 8.02 (s, 1H), 7.94-7.76 (m, 3H), 7.71-7.62 (m, 2H), 7.48 (d, J=1.3 Hz, 1H), 7.46-7.40 (m, 2H), 7.38 (s, 1H), 7.23 (s, 1H), 7.14 (d, J=1.5 Hz, 1H), 6.48 (s, 1H), 6.46 (s, 1H), 5.92 (s, 1H), 5.72 (t, J=3.2 Hz, 2H), 5.57 (s, 1H), 5.20 (s, 2H), 4.90-4.83 (m, 2H), 4.74 (s, 2H), 4.51-4.42 (m, 4H), 3.38 (d, J=5.7 Hz, 1H), 2.09 (s, 3H), 2.08 (s, 3H), 1.22 (m, 6H).

Biological Assay

Stimulation of Human STING Signalling in THP1 Cell Line

Compounds were tested for their STING activation potential using human THP1-Blue™ ISG SEAP based reporter cell line (Invivogen). Briefly, THP1-Blue ISG cells (100,000 cells/well) in 96 well plate were treated with varying concentrations of test and reference compounds and incubated at 37° C. with 5% $CO_2$ for 18-20 hours. The control untreated cells were also set up. Post incubation, the cell supernatant was tested for SEAP (Secreted Embryonic Alkaline Phosphatase) activity using the QuantiBlue™ substrate reagent (Invivogen). The formation of blue coloured product was quantified by measuring absorbance at wavelength of 620 nm using PheraStar/Tecan reader. The average of duplicate readouts for each data point was plotted in GraphPad prism 6 against the concentration of test or reference compound to calculate $EC_{50}$ value. The fold of SEAP induction or increase in luminescence at different data points was estimated against the un-stimulated cell control set.

Compounds 1, 2, 3, 5, 6, 11, 12, 19, 26 and 35 have shown $EC_{50}$ value ranging from 1 to 10 nM.

Compounds 4, 9, 13, 16, 17, 20, 22 and 36 have shown $EC_{50}$ value ranging from 11 to 100 nM.

Quantification of the Cytokine Secretion in Mouse or Human Whole Blood in Response to STING Agonists Compounds were tested for their ability to induce cytokine secretion, particularly IFNβ in the mouse or human whole blood. Mouse blood was collected from C57BL/6 mice utilizing heparin as an anticoagulant. Human blood was collected in sodium heparin containing vacutainers. Mouse or human blood was diluted in 1:3 ratio (four fold) with serum-free RPMI medium containing 2× Penicillin-Streptomycin solution. Diluted whole blood (150 μL) was seeded in U-bottom plates and added with 50 μl test compound prepared in RPMI medium and mixed twice with a pipette followed by incubation the plate at 37° C. for 4 h (mice) and 5 h (human). Test compounds were added in final concentrations of 3 μM. After the incubation period, the samples were centrifuged at 2500 rpm for 5 min, and supernatant was collected and transferred to a V bottom plate and stored immediately at −80° C. Samples were processed for quantification of IFNβ by ELISA utilizing commercially available kits measuring either mouse IFNβ (VeriKine Mouse IFN Beta ELISA, PBL assay science, Catalog No 42400-2) or human IFNβ (VeriKine Human IFN Beta ELISA, PBL assay science, Catalog No. 41410-2), respectively. IFNβ levels were expressed in pg/mL.

In both mouse and human whole blood assay, compounds 1, 2 and 3 have shown IFNβ secretion ranging from 250-900 pg/mL.

Quantification of the Cytokine Secretion in Serum Samples from the CT-26 Tumor Bearing BALB/c Mice CT-26 tumor-bearing animals were administered with test compounds at the dose of 0.5 mg/kg, in a dose-volume of 5 ml/kg. Serum samples were collected at designated time points (3.5 h) and frozen at −80° C. till further estimation. Mouse serum samples were diluted appropriately with dilution buffer before estimation of IFNβ utilizing commercially available kits (VeriKine Mouse IFN Beta ELISA, PBL assay science, Catalog No 42400-2). Raw data values were corrected with the dilution factor and finally expressed in pg/mL.

Compounds 1 and 2 have shown IFNβ secretion 4344 and 28305 pg/mL, respectively.

Effect of Compounds on Tumor Volume in CT26 Allograft BALB/c Mice Model by Intravenous (i.v.) Administration Healthy, female BALB/c mice in the age group of 5-8 weeks issued from Research Animal Facility (RAF). These mice were housed in individually ventilated cages (IVC) in the experimental animal room and were acclimatized not less than 5 days prior to cell inoculation. All the experimental activities were carried out inside the biosafety cabinet to ensure sterility. Under aseptic conditions, Allograft tumor model was generated by inoculating BALB/c mice with 0.1 million CT26 single cell suspension, using 1 mL disposable syringe fitted with a 26G ½" sterile needle. Each mouse was inoculated with 100 μL of CT26 cell suspension in DMEM media, subcutaneously in right flank region. Mice were randomized into different groups, post cell inoculation, with approximately equal mean and equal variation (S.E.M.) of tumor volumes in various treatment groups including vehicle control group.

Tumor size was measured with Vernier caliper when the tumor became palpable. Tumor volume (T. V.) was calculated by using the formula:

$$\text{Tumor volume (mm}^3) = (L \times W^2)/2$$

Where, L—Length of tumor, W—Width of tumor

Mice were selected and randomized, on the basis of tumor volume, into required no. of groups with approximately equal mean and equal variation on day 1 of treatment, post-tumor cell inoculation. All study groups were treated via intravenous route on day 1, 4 and 8 dosing schedule, through lateral tail vein at a dose volume of 5 mL/kg.

Tumor sizes were measured with Vernier caliper twice weekly and body weights of mice were recorded daily.

Percent tumor growth inhibition (% TGI) was calculated using the formula:

$$\%\ TGI = [1(Tf - Ti)/(Cf - Ci)] \times 100$$

Where, Tf and Ti, are the final and initial test tumor volumes, and Cf and Ci are the final and initial control mean tumor volumes, respectively.

Percent Tumor Regression (% TR) was calculated using the formula:

$$\%\ TR = [(\text{Initial } T.V. - \text{Final } T.V.)/(\text{Initial } T.V.)] \times 100$$

Where, T.V.=Tumor Volume

All the animals have shown >80% tumor regression on day 21 in CT-26 ectopic allograft BALB/c mice model when compounds 1, 2, and 3 are dosed at 0.75 mpk, 0.375 mpk and 1.5 mpk, respectively.

We claim:

1. A compound of Formula (Ia), its stereoisomer, or its pharmaceutically acceptable salt, (Ia)

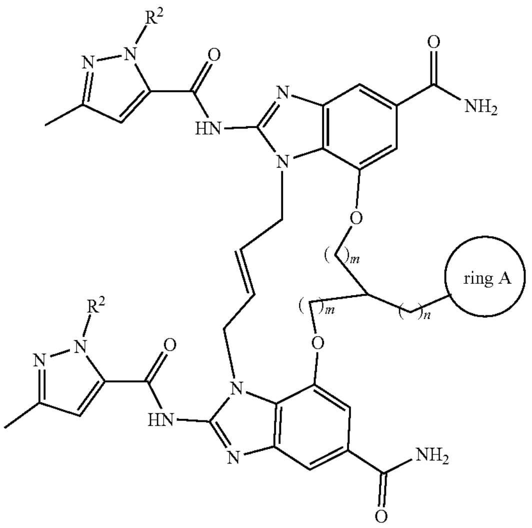

wherein, $R^2$ is independently selected from hydrogen, optionally substituted $C_1$-$C_6$ alkyl, and optionally substituted $C_3$-$C_5$ monocyclic cycloalkyl;

ring A is independently selected from optionally substituted heterocyclyl, and optionally substituted heteroaryl;

m is selected from 0, or 1;

n is selected from 0, 1, or 2;

when 'alkyl' is substituted, it is substituted with 1 to 4 substituents independently selected from halogen, alkyl, perhaloalkyl, cycloalkyl, heterocyclyl, —N($R^4$)$_2$, and —O$R^4$;

when 'carbocycle' or 'cycloalkyl' is substituted, it is substituted with 1 to 4 substituents independently selected from halogen, alkyl, perhaloalkyl, —N($R^4$)$_2$, and —O$R^4$;

when 'heterocycle' or 'heterocyclyl' is substituted, it is substituted with 1 to 4 substituents independently selected from oxo (═O), halogen, cyano, alkyl, perhaloalkyl, —O$R^4$, —C(═O)OH, —OP(O)(O$R^4$)$_2$, —P(O)(O$R^4$)$_2$, —P(O)(O$R^4$)$R^{4a}$, —SO$_2R^{4a}$, —SO$_2$NH$_2$, —C(═O)N(H)$R^4$, —C(═O)N(alkyl)$R^4$, —N(H)C(═O)$R^{4a}$, —N(H)$R^4$, and —N(alkyl)$R^4$;

when the 'heteroaryl' group is substituted, it is substituted with 1 to 4 substituents selected from halogen, cyano, alkyl, perhaloalkyl, —O-alkyl, —O-perhaloalkyl, —N(alkyl)alkyl, —N(H)$R^4$, —SO$_2$-alkyl, —N(alkyl)C(═O)alkyl, —N(H)C(═O)alkyl, —C(═O)N(alkyl)alkyl, —C(═O)N(H)alkyl, —C(═O)NH$_2$, —SO$_2$N(alkyl)alkyl, —SO$_2$N(H)alkyl, —SO$_2$NH$_2$, —C(═O)OH, —OP(O)(O$R^4$)$_2$, —P(O)(O$R^4$)$_2$, and —P(O)(O$R^4$)$R^{4a}$;

each $R^4$ is independently selected from hydrogen, alkyl, and cycloalkyl; and each $R^{4a}$ is independently selected from alkyl, and cycloalkyl.

2. The compound of Formula (Ia), its stereoisomer, or its pharmaceutically acceptable salt, as claimed in claim 1, wherein, ring A is optionally substituted heterocyclyl or optionally substituted heteroaryl.

3. The compound of Formula (Ia), its stereoisomer, or its pharmaceutically acceptable salt, as claimed in claim 1, wherein, ring A is

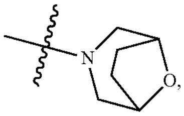 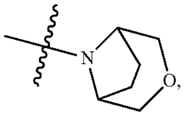 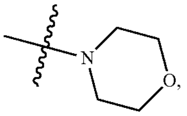

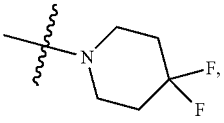 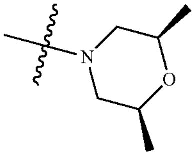 ,

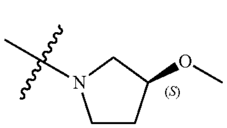 , 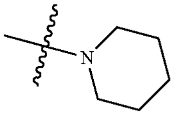 ,

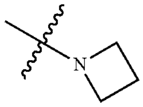 , 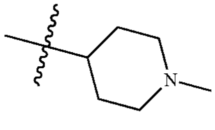 ,

-continued

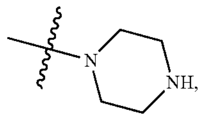 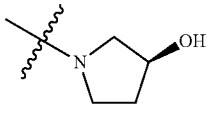 ,

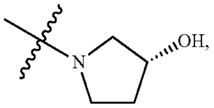 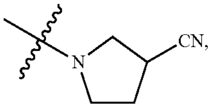

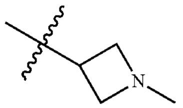 , 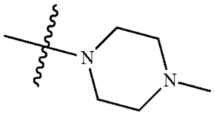 ,

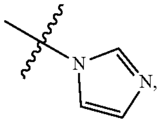 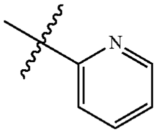 ,

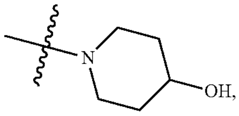 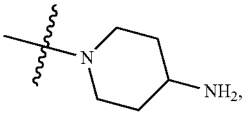

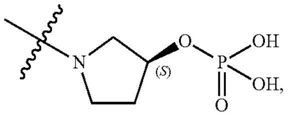

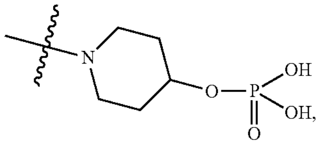

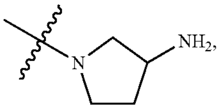 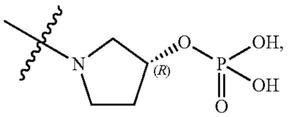

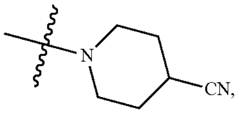 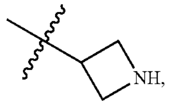

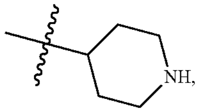 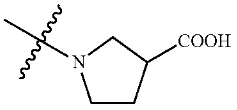 ,

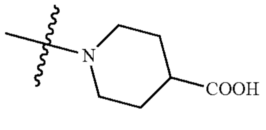 and 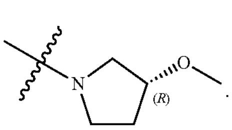 .

4. The compound of Formula (Ia), its stereoisomer, or its pharmaceutically acceptable salt, as claimed in claim 1, wherein, $R^2$ is ethyl.

5. The compound of Formula (Ia), its stereoisomer, or its pharmaceutically acceptable salt, as claimed in claim 1, wherein, n is 0.

6. The compound of Formula (Ia), its stereoisomer, or its pharmaceutically acceptable salt, as claimed in claim 1, wherein, $R^2$ is $C_1$-$C_6$ alkyl; n is 0, 1, or 2; and ring A is optionally substituted heterocyclyl or optionally substituted heteroaryl.

7. The compound of Formula (Ia), its stereoisomer, or its pharmaceutically acceptable salt, as claimed in claim 1, wherein, the compound is selected from:

(E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 1);

(E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 2);

(E)-1,15-bis(1-ethyl-3-methyl-1H-pyrazole-5-carboxamido)-8-morpholino-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 3);

(E)-8-(4,4-difluoropiperidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 4);

(E)-8-((2S,6R)-2,6-dimethylmorpholino)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 5);

(S,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 6);

(E)-1,15-bis(1-ethyl-3-methyl-1H-pyrazole-5-carboxamido)-8-(piperidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 7);

(E)-8-(azetidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 8);

(E)-1,15-bis(1-ethyl-3-methyl-1H-pyrazole-5-carboxamido)-8-(1-methylpiperidin-4-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 9);

(E)-1,15-bis(1-ethyl-3-methyl-1H-pyrazole-5-carboxamido)-8-(piperazin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 10);

(S,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 11);

(R,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 12);

(E)-1,15-bis(1-ethyl-3-methyl-1H-pyrazole-5-carboxamido)-8-(2-morpholinoethyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 13);

(E)-1,15-bis(1-ethyl-3-methyl-1H-pyrazole-5-carboxamido)-8-((1-methylazetidin-3-yl)methyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 14);

(E)-1,15-bis(1-ethyl-3-methyl-1H-pyrazole-5-carboxamido)-8-((1-methylpiperidin-4-yl)methyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 15);

(E)-1,15-bis(1-ethyl-3-methyl-1H-pyrazole-5-carboxamido)-8-(morpholinomethyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 16);

(E)-15-(1-ethyl-3-methyl-1H-pyrazole-5-carboxamido)-1-(1-(2-fluoroethyl)-3-methyl-1H-pyrazole-5-carboxamido)-8-morpholino-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 17);

(E)-1,15-bis(1-ethyl-3-methyl-1H-pyrazole-5-carboxamido)-8-((4-methylpiperazin-1-yl)methyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 18);

(E)-1,15-bis(1-ethyl-3-methyl-1H-pyrazole-5-carboxamido)-8-(1H-imidazol-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 19);

(E)-1,15-bis(1-ethyl-3-methyl-1H-pyrazole-5-carboxamido)-8-(4-hydroxypiperidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 22);

(E)-8-(4-aminopiperidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 23);

(S,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diinden-8-yl) pyrrolidin-3-yl dihydrogen phosphate (Compound 24);

(E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diinden-8-yl) piperidin-4-yl dihydrogen phosphate (Compound 25);

(E)-8-(3-cyanopyrrolidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 26);

(E)-8-(3-aminopyrrolidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 27);

(R,E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diinden-8-yl) pyrrolidin-3-yl dihydrogen phosphate (Compound 28);

(E)-8-(4-cyanopiperidin-1-yl)-1,15-bis(1-ethyl-3-methyl-1H-pyrazole-5-carboxamido)-8,9,16,19-tetrahydro- 7H-6,10-dioxa-2,14,15a, 19a-tetraazacyclopentadeca[3,2,1-cd:8,9,10-c'd']diindene-4,12-dicarboxamide (Compound 29);

(E)-8-(azetidin-3-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 30);

(E)-1,15-bis(1-ethyl-3-methyl-1H-pyrazole-5-carboxamido)-8-(piperidin-4-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 31);

(E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diinden-8-yl) pyrrolidine-3-carboxylic acid (Compound 32);

(E)-1-(4,12-dicarbamoyl-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diinden-8-yl) piperidine-4-carboxylic acid (Compound 33);

(E)-1,15-bis(1-ethyl-3-methyl-1H-pyrazole-5-carboxamido)-8-(1-methylazetidin-3-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 34);

(R,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 35); and (E)-1,15-bis(1-ethyl-3-methyl-1H-pyrazole-5-carboxamido)-8-(pyridin-2-yl)-8,9,16,19-tetrahydro-7H-6,10-dioxa-2,14,15a, 19a-tetraazacyclopentadeca[3,2,1-cd:8,9,10-c'd']diindene-4,12-dicarboxamidexamide (Compound 36).

8. The compound of Formula (Ia), its stereoisomer, or its pharmaceutically acceptable salt, as claimed in claim 1, wherein, the compound is selected from:

(E)-8-(8-oxa-3-azabicyclo[3.2.1]octan-3-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 1);

(E)-8-(3-oxa-8-azabicyclo[3.2.1]octan-8-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 2);

(E)-1,15-bis(1-ethyl-3-methyl-1H-pyrazole-5-carboxamido)-8-morpholino-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 3);

(E)-8-(4,4-difluoropiperidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 4);

(E)-8-((2S,6R)-2,6-dimethylmorpholino)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 5);

(S,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 6);

(E)-1,15-bis(1-ethyl-3-methyl-1H-pyrazole-5-carboxamido)-8-(1-methylpiperidin-4-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 9);

(S,E)-1,15-bis(1-ethyl-3-methyl-1H-pyrazole-5-carboxamido)-8-(3-hydroxypyrrolidin-1-yl)-8,9,16,19-tetrahydro-7H-6, 10-dioxa-2,14,15a, 19a-tetraazacyclopentadeca[3,2,1-cd:8,9,10-c'd']diindene-4,12-dicarboxamide (Compound 11);

(R,E)-1,15-bis(1-ethyl-3-methyl-1H-pyrazole-5-carboxamido)-8-(3-hydroxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 12);

(E)-1,15-bis(1-ethyl-3-methyl-1H-pyrazole-5-carboxamido)-8-(2-morpholinoethyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 13);

(E)-1,15-bis(1-ethyl-3-methyl-1H-pyrazole-5-carboxamido)-8-(morpholinomethyl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 16);

(E)-15-(1-ethyl-3-methyl-1H-pyrazole-5-carboxamido)-1-(1-(2-fluoroethyl)-3-methyl-1H-pyrazole-5-carboxamido)-8-morpholino-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 17);

(E)-1,15-bis(1-ethyl-3-methyl-1H-pyrazole-5-carboxamido)-8-(1H-imidazol-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 19);

(E)-1,15-bis(1-ethyl-3-methyl-1H-pyrazole-5-carboxamido)-8-(4-hydroxypiperidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 22);

(E)-8-(3-cyanopyrrolidin-1-yl)-1,15-bis(1-ethyl-3-methyl-1H-pyrazole-5-carboxamido)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 26);

(R,E)-1,15-bis(1-ethyl-3-methyl-1H-pyrazole-5-carboxamido)-8-(3-methoxypyrrolidin-1-yl)-8,9,16,19-tetrahydro-7H-6,10-dioxa-2,14,15a, 19a-tetraazacyclopentadeca[3,2,1-cd:8,9,10-c'd']diindene-4,12-dicarboxamide (Compound 35); and (E)-1,15-bis(1-ethyl-3-methyl-1H-pyrazole-5-carboxamido)-8-(pyridin-2-yl)-8,9,16,19-tetrahydro-7H-6,10-dioxa-2,14,15a, 19a-tetraazacyclopentadeca[3,2,1-cd:8,9,10-c'd']diindene-4,12-dicarboxamidexamide (Compound 36).

9. A pharmaceutical composition comprising the compound of Formula (Ia), or its pharmaceutically acceptable salt as claimed in claim 1 and at least one or more pharmaceutically acceptable excipient.

10. A composition comprising a compound of Formula (Ia), or its pharmaceutically acceptable salt as claimed in claim 1 and an antigen or antigen composition.

* * * * *